US006627736B1

United States Patent
(12) United States Patent
Tumer

(10) Patent No.: US 6,627,736 B1
(45) Date of Patent: Sep. 30, 2003

(54) PAP MUTANTS THAT EXHIBIT ANTI-VIRAL AND/OR ANTI-FUNGAL ACTIVITY IN PLANTS

(75) Inventor: Nilgun E. Tumer, Belle Mead, NJ (US)

(73) Assignee: Rutgers, The State University, New Brunswick, NJ (US)

(*) Notice: Subject to any disclaimer, the term of this patent is extended or adjusted under 35 U.S.C. 154(b) by 91 days.

(21) Appl. No.: 09/639,456

(22) Filed: Aug. 15, 2000

Related U.S. Application Data

(60) Division of application No. 09/005,273, filed on Jan. 9, 1998, now Pat. No. 6,137,030, which is a continuation of application No. PCT/US96/11546, filed on Jul. 11, 1996, which is a continuation-in-part of application No. 08/500,611, filed on Jul. 11, 1995, now Pat. No. 5,756,322, which is a continuation-in-part of application No. 08/500,694, filed on Jul. 11, 1995, now Pat. No. 5,880,329.

(51) Int. Cl.[7] .......................... A01H 5/00; C12N 15/82; C07K 1/00; C07K 14/00; A61K 35/78

(52) U.S. Cl. ....................... 530/370; 435/440; 435/468; 435/254.2

(58) Field of Search ................................ 530/370, 350; 435/4, 6, 7.2, 7.4, 7.6, 254.2, 254.21, 252.3, 440, 468

(56) References Cited

U.S. PATENT DOCUMENTS 5,304,730 A 4/1994 Lawson et al.

FOREIGN PATENT DOCUMENTS

FR 2699553 A1 6/1994

OTHER PUBLICATIONS

Dore et al, "Mutation dissociating the inhibitory activity of the pokeweek antiviral protein on eukaryote translation and *escherichia coli* growth", 1993, vol. 21 No. 18, pp. 4200–4205.*

Abel et al., Science 232:738–43 (1986).
Cuozzo et al., Bio/Technology 6:549–57 (1988).
Hemenway et al., EMBO J. 7:1273–80 (1988).
Stark et al., Bio/Technology 7:1257–62 (1989).
Lawson et al., Bio/Technology 8:127–34 (1990).
Kawchuk et al., Mol. Plant–Microbe Interactions 3(5):301–07 (1990).
Lodge et al., Proc. Natl. Acad. Sci. USA 90:7089–93 (1993).
Irvin et al., Pharmac. Ther. 55:279–302 (1992).
Endo et al., Biophys. Res. Comm., 150:1032–36 (1988).
Hartley et al., FEBS Lett. 290:65–68 (1991).
Beachy et al., Ann. Rev. Phytopathol. 28:451–74 (1990).
Golemboski et al., Proc. Natl. Acad. Sci. USA 87:6311–15 (1990).
Hayashi et al., J. Bioenerg. Biomem. 22:451–71 (1990).
Dore et al., Nuc. Acids Res. 21(18):4200–05 (1993).
Monzingo et al., J. Mol. Biol. 233:705–15 (1993).
Chen et al., Plant Pathol. 40:612–20 (1991).

* cited by examiner

*Primary Examiner*—Elizabeth F. McElwain
(74) *Attorney, Agent, or Firm*—Lerner, David, Littenberg, Krumholz & Mentlik, LLP

(57) ABSTRACT

Disclosed are PAP mutants having reduced phytotoxicity compared to wild-type PAP, and which confer broad spectrum resistance to viruses and/or fungi in plants. One group of PAP mutants is characterized by at least one amino acid substitution in the N-terminus of mature PAP, such as the Glycine 75 residue or the Glutamic acid 97 residue; two groups of additional PAP mutants are characterized by truncations in the N-terminal region of mature PAP and truncations or amino acid substitutions in the C-terminal region of mature PAP, respectively; and a further group are enzymatically inactive which still exhibit anti-fungal properties. Also disclosed are DNA molecules encoding the PAP mutants, mutant PAP DNA constructs, and transgenic seed and plants containing the DNAs. Further disclosed are methods for identifying PAP mutants having reduced phytotoxicity, as well as isolated and purified PAP mutants identified by the method.

51 Claims, No Drawings

PAP MUTANTS THAT EXHIBIT ANTI-VIRAL AND/OR ANTI-FUNGAL ACTIVITY IN PLANTS

CROSS-REFERENCE TO RELATED APPLICATIONS

This application is a divisional of U.S. application Ser. No. 09/005,273, filed Jan. 9, 1998, now U.S. Pat. No. 6,137,030, which is a continuation of PCT/US96/11546, filed Jul. 11, 1996, which is a continuation-in-part of U.S. application Ser. No. 08/500,611, filed Jul. 11, 1995, now U.S. Pat. No. 5,756,322, and application Ser. No. 08/500,694, filed Jul. 11, 1995, now U.S. Pat. No. 5,880,329.

FIELD OF THE INVENTION

This invention relates generally to agricultural biotechnology, and more specifically to methods and genetic materials for conferring resistance to fungi and/or viruses in plants.

BACKGROUND OF THE INVENTION

The subject of plant protection against pathogens remains the area of utmost importance in agriculture. Many commercially valuable agricultural crops are prone to infection by plant viruses and fungi capable of inflicting significant damage to a crop in a given season, and drastically reducing its economic value. The reduction in economic value to the farmer in turn results in a higher cost of goods to ultimate purchasers. Several published studies have been directed to the expression of plant virus capsid proteins in a plant in an effort to confer resistance to viruses. See, e.g., Abel et al., Science 232:738–743 (1986); Cuozzo et al., Bio/Technology 6:549–557 (1988); Hemenway et al., EMBO J. 7:1273–1280 (1988); Stark et al., Bio/Technology 7:1257–1262 (1989); and Lawson et al., Bio/Technology 8:127–134 (1990). However, the transgenic plants exhibited resistance only to the homologous virus and related viruses, but not to unrelated viruses. Kawchuk et al., Mol. Plant-Microbe Interactions 3(5):301–307 (1990), disclose the expression of wild-type potato leaf roll virus (PLRV) coat protein gene in potato plants. Even though the infected plants exhibited resistance to PLRV, all of the transgenic plants that were inoculated with PLRV became infected with the virus and thus disadvantageously allowed for the continued transmission of the virus such that high levels of resistance could not be expected. See U.S. Pat. No. 5,304,730.

Lodge et al., Proc. Natl. Acad. Sci. USA 90:7089–7093 (1993), report the *Agrobacterium tumefaciens*-mediated transformation of tobacco with a cDNA encoding wild-type pokeweed antiviral protein (PAP) and the resistance of the transgenic tobacco plants to unrelated viruses. PAP, a Type I ribosome-inhibiting protein (RIP) found in the cell walls of *Phytolacca americana* (pokeweed), is a single polypeptide chain that catalytically removes a specific adenine residue from a highly conserved stem-loop structure in the 28S rRNA of eukaryotic ribosomes, and interferes with elongation factor-2 binding and blocking cellular protein synthesis. See, e.g., Irvin et al., Pharmac. Ther. 55:279–302 (1992); Endo et al., Biophys. Res. Comm., 150:1032–36 (1988); and Hartley et al., FEBS Lett. 290:65–68 (1991). The observations by Lodge were in sharp contrast to previous studies, supra, which reported that transgenic plants expressing a viral gene were resistant to that virus and closely related viruses only. See also Beachy et al., Ann. Rev. Phytopathol. 28:451–74 (1990); and Golemboski et al., Proc. Natl. Acad. Sci. USA 87:6311–15 (1990). Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile. RIPs have proven unpredictable in other respects such as target specificity. Unlike PAP which (as demonstrated in Lodge), ricin isolated from castor bean seed is 1000 times more active on mammalian ribosomes than plant ribosomes. See, e.g., Harley et al., Proc. Natl. Acad. Sci. USA 79:5935–5938 (1982). Barley endosperm RIP also shows very little activity against plant ribosomes. See, e.g., Endo et al., Biochem. Biophys. Acta 994:224–226 (1988) and Taylor et al., Plant J. 5:827–835 (1984).

Fungal pathogens contribute significantly to the most severe pathogen outbreaks in plants. Plants have developed a natural defense system, including morphological modifications in their cell walls, and synthesis of various anti-pathogenic compounds. See, e.g., Boller et al., Plant Physiol 74:442–444 (1984); Bowles, Annu. Rev. Biochem. 59:873–907 (1990); Joosten et al., Plant Physiol. 89:945–951 (1989); Legrand et al., Proc. Natl. Acad. Sci. USA 84:6750–6754 (1987); and Roby et al., Plant Cell 2:999–1007 (1990). Several pathogenesis-related (PR) proteins have been shown to have anti-fungal properties and are induced following pathogen infection. These are different forms of hydrolytic enzymes, such as chitinases and β-1,3-glucanases that inhibit fungal growth in vitro by destroying fungal cell walls. See, e.g., Boller et al., supra; Grenier et al., Plant Physiol. 103:1277–123 (1993); Leah et al., J. Biol. Chem. 266:1464–1573 (1991); Mauch et al., Plant Physiol. 87:325–333 (1988); and Sela-Buurlage Buurlage et al., Plant Physiol. 101:857–863 (1993).

Several attempts have been made to enhance the pathogen resistance of plants via recombinant methodologies using genes encoding pathogenesis-related proteins (such as chitinases and β-1,3-glucanases) with distinct lytic activities against fungal cell walls. See, e.g., Broglie et al., Science 254:1194–1197 (1991); Vierheilig et al., Mol. Plant-Microbe Interact. 6:261–264 (1993); and Zhu et al., Bio/Technology 12:807–812 (1994). Recently, two other classes of genes have been shown to have potential in conferring disease resistance in plants. Wu et al., Plant Cell 7:1357–1368 (1995), report that transgenic potato expressing the *Aspergillus niger* glucose oxidase gene exhibited increased resistance to *Erwinia carotovora* and *Phytophthora infestans*. The hypothesis is that the glucose oxidase-catalyzed oxidation of glucose produces hydrogen peroxide, which when accumulates in plant tissues, leads to the accumulation of active oxygen species, which in turn, triggers production of various anti-pathogen and anti-fungal mechanisms such as phytoalexins (see Apostol et al., Plant Physiol. 90:109–116 (1989) and Degousee, Plant Physiol. 104:945–952 (1994)), pathogenesis-related proteins (Klessig et al., Plant Mol. Biol. 26:1439–1458 (1994)), strengthening of the plant cell wall (Brisson et al., Plant Cell 6:1703–1712 (1994)), induction of systemic acquired resistance by salicylic acid (Chen et al., Science 162:1883–1886 (1993)), and hypersensitive defense response (Levine et al., Cell 79:583–593 (1994)).

In addition to the studies on virus resistance in plants, RIPs have been studied in conjunction with fungal resistance. For example, Logeman et al., Bio/Technology 10:305–308 (1992), report that a RIP isolated from barley endosperm provided protection against fungal infection to transgenic tobacco plants. The combination of barley endosperm RIP and barley class-II chitinase has provided synergistic enhancement of resistance to *Rhizoctonia solani* in tobacco, both in vitro and in vivo. See, e.g., Lea et al., supra; Mauch et al., supra; Zhu et al., supra; and Jach et al., The Plant Journal 8:97–109 (1995). PAP, however, has not shown antifungal activity in vitro. See Chen et al., Plant Pathol. 40:612–620 (1991), which reports that PAP has no effect on the growth of the fungi *Phytophthora infestans, Colletotrichum coccodes, fusarium solani, fusarium sulphureum, Phoma foreata* and *Rhizoctonia solani* in vitro.

Hence, a need remains for a means by which to confer broad spectrum virus and/or fungus resistance to plants without causing cell death or sterility, and which requires a minimum number of transgenes.

BRIEF SUMMARY OF THE INVENTION

The present invention is directed to PAP mutants having reduced phytotoxicity, and which exhibit PAP biological activity in plants. By "PAP biological activity," it is meant PAP anti-viral activity and/or PAP anti-fungal activity. One preferred group of PAP mutants is characterized by at least one amino acid substitution in the N-terminus of mature PAP, such as a substitution for the Glycine 75 residue or the Glutamic acid 97 residue. Another group of PAP mutants is characterized by a truncation of as many as 38 amino acids at the N-terminus of mature PAP. Yet another preferred group of PAP mutants is characterized by mutations such as truncations in the C-terminal region of mature PAP. More preferred are PAP mutants truncated at their C-terminus by at least about 26 to about 76 mature PAP amino acids (not counting the 29-amino acid C-terminal extension of wild-type PAP). A further group of PAP mutants are enzymatically inactive and do not exhibit PAP anti-viral activity in vitro or in planta; yet, they exhibit PAP anti-fungal activity in plants. The PAP mutants of the present invention may also include the 22-amino acid N-terminal signal sequence and/or the C-terminal extension of wild-type PAP.

The present invention also provides DNA molecules encoding the PAP mutants, which may or may not also encode the 22-amino acid N-terminal signal sequence of mature PAP and/or the 29-amino acid C-terminal extension of wild-type PAP. The DNAs can be operably linked to a promoter functional in procaryotic cells (e.g., *E. coli*), or eukaryotic cells such as plants, and then stably transformed into a vector functional in said cells. Hosts, e.g., procaryotic or eukaryotic cells (e.g., yeast or plants), stably transformed with a mutant PAP-encoding DNA are also provided, as well as protoplasts stably transformed with the DNAs. Transgenic plants and seed containing the DNAs are also provided. Expression of the DNAs in the transgenic plants confers broad spectrum virus and/or fungus resistance upon the plants without being as phytotoxic to the plant as wild-type PAP. Plants included within the scope of the present invention are monocots, such as cereal crops, and dicot plants.

The present invention further provides a method for identifying a PAP mutant having reduced phytotoxicity and which exhibits PAP biological activity in plants. The method involves the steps of providing a transformed eukaryotic cell such as yeast containing a mature PAP-encoding DNA molecule operably linked to an inducible promoter functional in the eukaryotic cell. The PAP-encoding DNA is mutagenized prior to transformation, or the transformed cell is mutagenized (i.e., the mutagenesis is performed after the cell is transformed with the PAP construct). The thus-transformed cells are cultured in a suitable medium, and after a predetermined time, an inducer is added to the medium to cause expression of the DNA molecule. A determination is then made as to whether the survival of cultured cells is due to the expression of a mutant PAP. Such mutant PAPs which exhibit a substantial lack of toxicity to the host would be considered as PAP mutants which exhibit reduced phytotoxicity. The thus-identified PAP mutants which also exhibit broad spectrum virus and/or fungus resistance, as determined by in vitro (e.g., by exogenous application of the virus or fungus), or in vivo (e.g., by expression in transgenic plants); would also be considered as PAP mutants which retain PAP biological activity in plants. The present invention further provides isolated and purified PAP mutants identified by the aforesaid method.

DETAILED DESCRIPTION OF THE INVENTION

Transgenic plants expressing DNAs encoding the PAP mutants of the present invention exhibit reduced phytotoxicity compared to transgenic plants that produce mature, wild-type PAP, ("PAP"), or variant PAP, i.e. PAP-v, but also exhibit anti-viral and/or anti-fungal activities. By the term "reduced phytotoxicity," it is meant that a transgenic plant which expresses a mutant PAP-encoding DNA exhibits a normal and fertile phenotype and does not exhibit the stunted, mottled phenotype characteristic of transgenic plants that produce mature PAP (as disclosed in Lodge for example). By "wild-type PAP," it is meant the PAP amino acid sequence 1-262, the 22-amino acid N-terminal signal peptide ("the N-terminal signal sequence of wild-type PAP"), and the 29 amino acid C-terminal extension (amino acids enumerated 263-291), all illustrated in Table I below as SEQ ID NO:2. The corresponding nucleotide sequence is set forth as SEQ ID NO:1. Thus, by the terms "wild-type, mature PAP," or "mature PAP", it is meant the PAP amino acid sequence 1-262 shown in Table I.

TABLE I

```
5'CTATGAAGTCGGGTCAAAGCATATACAGGCTATGCATTGTTAGAAACATTGATGCCTCTGATCCC
GATAAACAATACAAATTAGACAATAAGATGACATACAAGTACCTAAACTGTGTATGGGGGAGTGA
AACCTCAGCTGCTAAAAAAACGTTGTAAGAAAAAAAGAAAGTTGTGAGTTAACTACAGGGCGAAA
GTATTGGAACT
                        A
AGCTAGTAGGAAGGGAAG ATG AAG TCG ATG CTT GTG GTG ACA ATA TCA ATA
                 Met Lys Ser Met Leu Val Val Thr Ile Ser Ile
                                        (67)
TGG CTC ATT CTT GCA CCA ACT TCA ACT TGG GCT GTG AAT ACA ATC ATC TAC
Trp Leu Ile Leu Ala Pro Thr Ser Thr Trp Ala Val Asn Thr Ile Ile Tyr
                                         (1)
                 (100)                          G
AAT GTT GGA AGT ACC ACC ATT AGC AAA TAC GCC ACT TTT CTG AAT GAT CTT
Asn Val Gly Ser Thr Thr Ile Ser Lys Tyr Ala Thr Phe Leu Asn Asp Leu
           (10)                                 (20)
CGT AAT GAA GCG AAA GAT CCA AGT TTA AAA TGC TAT GGA ATA CCA ATG CTG
```

TABLE I-continued

```
Arg Asn Glu Ala Lys Asp Pro Ser Leu Lys Cys Tyr Gly Ile Pro Met Leu
                    (30)                                     (40)
                             C
CCC AAT ACA AAT ACA AAT CCA AAG TAC GTG TTG GTT GAG CTC CAA GGT TCA
Pro Asn Thr Asn Thr Asn Pro Lys Tyr Val Leu Val Glu Leu Gln Gly Ser
                                (50)
AAT AAA AAA ACC ATC ACA CTA ATG CTG AGA CGA AAC AAT TTG TAT GTG ATG
Asn Lys Lys Thr Ile Thr Leu Met Leu Arg Arg Asn Asn Leu Tyr Val Met
    (60)                                      (70)
GGT TAT TCT GAT CCC TTT GAA ACC AAT AAA TGT CGT TAC CAT ATC TTT AAT
Gly Tyr Ser Asp Pro Phe Glu Thr Asn Lys Cys Arg Tyr His Ile Phe Asn
                  (80)                                 (90)
GAT ATC TCA GGT ACT GAA CGC CAA GAT GTA GAG ACT ACT CTT TGC CCA AAT
Asp Ile Ser Gly Thr Glu Arg Gln Asp Val Glu Thr Thr Leu Cys Pro Asn
                             (100)
GCC AAT TCT CGT GTT AGT AAA AAC ATA AAC TTT GAT AGT CGA TAT CCA ACA
Ala Asn Ser Arg Val Ser Lys Asn Ile Asn Phe Asp Ser Arg Tyr Pro Thr
    (110)                                 (120)
TTG GAA TCA AAA GCG GGA GTA AAA TCA AGA AGT CAG GTC CAA CTG GGA ATT
Leu Glu Ser Lys Ala Gly Val Lys Ser Arg Ser Gln Val Gln Leu Gly Ile
               (130)                                  (140)
CAA ATA CTC GAC AGT AAT ATT GGA AAG ATT TCT GGA GTG ATG TCA TTC ACT
Gln Ile Leu Asp Ser Asn Ile Gly Lys Ile Ser Gly Val Met Ser Phe Thr
                          (150)
GAG AAA ACC GAA GCC GAA TTC CTA TTG GTA GCC ATA CAA ATG GTA TCA GAG
Glu Lys Thr Glu Ala Glu Phe Leu Leu Val Ala Ile Gln Met Val Ser Glu
(160)                                (170)
GCA GCA AGA TTC AAG TAC ATA GAG AAT CAG GTG AAA ACT AAT TTT AAC AGA
Ala Ala Arg Phe Lys Tyr Ile Glu Asn Gln Val Lys Thr Asn Phe Asn Arg
           (180)                                  (190)
GCA TTC AAC CCT AAT CCC AAA GTA CTT AAT TTG CAA GAG ACA TGG GGT AAG
Ala Phe Asn Pro Asn Pro Lys Val Leu Asn Leu Gln Glu Thr Trp Gly Lys
                       (200)                              (210)
ATT TCA ACA GCA ATT CAT GAT GCC AAG AAT GGA GTT TTA CCC AAA CCT CTC
Ile Ser Thr Ala Ile His Asp Ala Lys Asn Gly Val Leu Pro Lys Pro Leu
                                 (220)
GAG CTA GTG GAT GCC AGT GGT GCC AAG TGG ATA GTG TTG AGA GTG GAT GAA
Glu Leu Val Asp Ala Ser Gly Ala Lys Trp Ile Val Leu Arg Val Asp Glu
       (230)                                  (240)
ATC AAG CCT GAT GTA GCA CTC TTA AAC TAC GTT GGT GGG AGC TGT CAG ACA
Ile Lys Pro Asp Val Ala Leu Leu Asn Tyr Val Gly GIy Ser Cys Gln Thr
                   (250)                                 (260)
ACT TAT AAC CAA AAT GCC ATG TTT CCT CAA CTT ATA ATG TCT ACT TAT TAT
Thr Tyr Asn Gln Asn Ala Met Phe Pro Gln Leu Ile Met Ser Thr Tyr Tyr
(262)                        (270)
AAT TAC ATG GTT AAT CTT GGT GAT CTA TTT GAA GGA TTC TGATCATAAACA
Asn Tyr Met Val Asn Leu Gly Asp Leu Phe Glu Gly Phe
   (280)                                  (290)
TAATAAGGAGTATATATATATTACTCCAACTATATTATAAAGCTTAAATAAGAGGCCGTGTTAATT
AGTACTTGTTGCTTTTGCTTTATGGTGTTGTTTATTATGCCTTGTATGCTTGTAATATTATCTAGAG
AACAAGATGTACTGTGTAATAGTCTTGTTTGAAATAAAACTTCCAATTATGATGCAAAAAAAAAA
AAAAA3'
```

Table I further shows PAP-v amino acids and corresponding nucleotides in proper alignment with wild-type PAP. Basically, the amino acid sequence of PAP-v differs from that of wild-type PAP in terms of a Leu20Arg (i.e., an arginine residue at position 20 of mature PAP as opposed to a leucine residue) and a Tyr49His substitution. The third change in the PAP-v nucleotide sequence (TCG→TCA codon for the first occurring Ser in the signal sequence) has no effect on the amino acid sequence. Table I also shows 5' and 3' non-coding, flanking sequences. Upon expression in eukaryotic cells, the N-terminal 22-amino acid sequence of wild-type PAP is co-translationally cleaved, yielding a polypeptide having a molecular weight of about 32 kD, which is then further processed by the cleavage of the C-terminal 29-amino acids ("the C-terminal extension of wild-type PAP" or "PAP (263-292)"), yielding mature, wild-type PAP (hereinafter "PAP (1-262)") (i.e., that which is isolated from *Phytolacca americana* leaves), having a molecular weight of about 29 kD. See Irvin et al., Pharmac. Ther. 55:279–302 (1992); Dore et al., Nuc. Acids Res. 21(18):4200–4205 (1993); Monzingo et al., J. Mol. Biol. 233:705–15 (1993); Turner et al., Proc. Natl. Acad. Sci. USA 92:8448–8452 (1995).

By the phrase "PAP anti-viral activity," it is meant that the expression of a mutant PAP of the present invention in a transgenic plant confers broad spectrum virus resistance, i.e., resistance to or the capability of suppressing infection by a number of unrelated viruses, including but not limited to RNA viruses e.g., potexviruses such as (PVX, potato virus X), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See also Lodge, Tomlinson et al., J. Gen. Virol. 22:225–232 (1974); and Chen et al., Plant Pathol. 40:612–620 (1991).

By the phrase "PAP anti-fungal activity", it is meant that the mutant PAPs of the present invention confer broad spectrum fungal resistance to plants. The mutant PAPs of the present invention provide increased resistance to diseases caused by plant fungi, including those caused by Pythium (one of the causes of seed rot, seedling damping off and root rot), Phytophthora (the cause of late blight of potato and of root rots, and blights of many other plants), Bremia, Peronospora, Plasmopara, Pseudoperonospora and Sclerospora (causing downy mildews), *Erysiphe graminis* (causing powdery mildew of cereals and grasses), Verticillium (causing vascular wilts of vegetables, flowers, crop plants and trees), Rhizoctonia (causing damping off disease of many plants and brown patch disease of turfgrasses), Fusarium (causing root rot of bean, dry rot of potatoes), Cochliobolus (causing root and foot rot, and also blight of cereals and grasses), Giberella (causing seedling blight and foot or stalk rot of corn and small grains), Gaeumannomyces (causing the take-all and whiteheads disease of cereals), Schlerotinia (causing crown rots and blights of flowers and vegetables and dollar spot disease of turfgrasses), Puccinia (causing the stem rust of wheat and other small grains), Ustilago (causing corn smut), Magnaporthae (causing summer patch of turfgrasses), and Schlerotium (causing southern blight of turfgrasses). Other important fungal diseases include those caused by Cercospora, Septoria, Mycosphoerella, Glomerella, Colletotrichum, Helminthosporium, Alterneria, Botrytis, Cladosporium, and Aspergillus.

Applicant also believes that the mutant PAPs of the present invention confer increased resistance to insects, bacteria and nematodes in plants. Important bacterial diseases include those caused by Pseudomonas, Xanthomonas, Erwinia, Clavibacter and Streptomyces.

The PAP mutants of the present invention differ from wild-type PAP substantially as follows: (1) those which exhibit altered compartmentalization in vivo; (2) C-terminal mutants, including but not limited to deletion or frameshift mutants; (3) N-terminal mutants; and (4) active-site mutants. The first category of PAP mutants may have altered compartmentalization properties in vivo; that is, they may not be localized in the same subcellular compartment as wild-type PAP. While not intending to be bound to any particular theory of operation, Applicant believes that these PAP mutants are unable to undergo co-translational processing (to remove the 22 amino acid signal peptide) and/or post-translational processing (to remove the 29-amino acid C-terminal fragment) in yeast, which results in substantially diminished or negligible cytotoxicity. These mutants are also non-phytotoxic. What is particularly surprising or unexpected about the function of these mutant PAPs in vivo is that the mutations are located within the sequence encoding the mature PAP (1-262), and not within the N-terminal signal peptide or the 29-amino acid C-terminal extension. In addition, the mutant PAPs are enzymatically active in inhibiting translation in vitro, indicating that phytotoxicity is not solely a function of enzymatic activity. Preferred PAP mutants include a conservative point mutation such that wild-type PAP amino acid residue 75 glycine (Gly75) is changed to valine, alanine, isoleucine or leucine, or (2) a conservative or non-conservative point mutation at wild-type PAP amino acid residue 97 Glutamic acid (Glu97). More preferred PAP mutants are PAP (1-262, Gly75Val) and PAP (1-262, Glu97Lys), the respective DNAs of which can be prepared simply by changing the wild-type GGT codon for glycine75 to GTT (valine), and the GAA codon for glutamic acid 97 to AAA (lysine). Other PAP mutants having altered compartmentalization properties can be identified by the selection method described below. Dore et al., supra, disclose an Arg67Gly PAP mutant (numbered in Dore as Arg 68Gly due to the presence of an N-terminal methionine residue), but which is toxic to eukaryotic cells and non-toxic to procaryotic cells such as *E. coli*. This mutant is not included within the scope of the present invention.

The second category of PAP mutants of the present invention have deletions or amino acid substitutions in the C-terminal region of PAP. Applicant has unexpectedly discovered that these mutants are also non-toxic in vivo (i.e., non-phytotoxic) even though they inhibit translation in vitro. Preferred mutants have deletions of from about 26 to about 76 amino acids of mature PAP, and more preferred are the PAP mutants PAP (1-236)-PAP (1-184), inclusive. Thus, truncations beginning at about amino acid residue 237 of wild-type mature PAP, e.g., PAP (1-236), PAP (1-235), PAP (1-234), PAP (1-233), PAP (1-232), PAP (1-231), PAP (1-230), PAP (1-229), PAP (1-228), PAP (1-227), PAP (1-226), PAP (1-225), PAP (1-224), PAP (1-223), PAP (1-222), PAP (1-221), PAP (1-220), PAP (1-219), PAP (1-218), PAP (1-217), PAP (1-216), PAP (1-215), PAP (1-214), PAP (1-213), PAP (1-212), PAP (1-211), PAP (1-210), PAP (1-209), PAP (1-208), PAP (1-207), PAP (1-206), PAP (1-205), PAP (1-204), PAP (1-203), PAP (1-202), PAP (1-201), PAP (1-200), PAP (1-199), PAP (1-198), PAP (1-197), PAP (1-196), PAP (1-195), PAP (1-194), PAP (1-193), PAP (1-192), PAP (1-191), PAP (1-190), PAP (1-189), PAP (1-188), PAP (1-187), PAP (1-186), PAP (1-185), and PAP (1-184) are encompassed by the present invention. More preferred mutants include PAP (1-184Glu), PAP (1-188Lys), PAP (1-206Glu), PAP (1-209) and PAP (1-236Lys). Deletions shorter than about 26 (i.e., between 1 and 25 amino acids, inclusive) or longer than 76 mature PAP amino acids are included in the scope of the present invention provided that they are non-toxic to plant cells, which can be determined by the selection method described in detail below, and they confer fungus and/or virus resistance in planta. The latter properties can be determined in vitro, e.g., by inoculating plant parts, e.g. leaves, with the PAP mutant in the presence of a virus or fungus, or by separate in vivo assays wherein a transgenic plant transformed with a mutant PAP-encoding DNA is inoculated with a fungus or virus. A preferred C-terminal substitution mutant is PAP (1-262, Leu202Phe). Again, while not intending to be bound by any particular theory of operation, Applicant believes that the sequence of PAP amino acids 244Glu-259Cys (shown in Table I), which is homologous to the consensus sequence for the prokaryotic membrane lipoprotein lipid attachment site (Hayashi et al., J. Bioenerg. Biomem. 22:451–471 (1990)), and which is absent from each of the PAP mutants disclosed above, is involved in binding of PAP to phospholipids on endoplasmic reticulum (ER) membranes which facilitates the translocation of PAP into the cytosol of the cell where it inhibits protein synthesis. Disarming this function, e.g., by deletion or by frameshift mutation, results in PAP mutants having the instantly disclosed properties.

Dore also discloses the PAP mutant Phe195Tyr, Lys211Arg (which numbering is +1 out-of-phase with the numbering used herein due to the N-terminal Met residue required for expression in *E. coli*), which is toxic to eukaryotic cells (such as plants) but non-toxic to procaryotes such as *E. coli*. Accordingly, this PAP mutant disclosed in the Dore publication is not included within the scope of the present invention.

The third category of PAP mutants is characterized by truncations of from 1 to at least about 38 N-terminal amino acid residues of mature PAP. These mutants include PAP (2-262), PAP (3-262), PAP (4-262), PAP (5-262), PAP (6-262), PAP (7-262), PAP (8-262), PAP (9-262), PAP (10-262), PAP (11-262), PAP (12-262), PAP (13-262), PAP (14-262), PAP (15-262), PAP (16-262), PAP (17-262), PAP (18-262), PAP (19-262), PAP (20-262), PAP (21-262), PAP (22-262), PAP (23-262), PAP (24-262), PAP (25-262), PAP (26-262), PAP (27-262), PAP (28-262), PAP (29-262), PAP (30-262), PAP (31-262), PAP (32-262), PAP (33-262), PAP (34-262), PAP (35-262), PAP (36-262), PAP (37-262), PAP (38-262) and PAP (39-262). Truncations of greater than 38 N-terminal amino acid residues of mature PAP are included within the scope of the present invention to the extent that they exhibit PAP biological activity and reduced phytotoxicity in vivo. These properties may be determined in accordance with the procedures set forth in the working examples, below.

The fourth category of PAP mutants contain active-site mutations which render the PAP molecule enzymatically inactive (as measured by their lack of ability to inhibit translation in vitro and/or in eukaryotic ribosomes). Applicant has surprisingly and unexpectedly found that these mutants exhibit broad spectrum anti-fungal activity when expressed in plants, even though they exhibit negligible PAP anti-viral activity. The putative active site of PAP includes amino acid residues Tyr72, Tyr123, Glu176, Arg179 and Trp208. Accordingly, PAP active site mutants, e.g., which contain a conservative or even non-conservative substitution in the PAP active site or wherein at least one active site amino acid is deleted or replaced by another amino acid, wherein the PAP is rendered enzymatically inactive but retains anti-fungal activity, are encompassed within the present invention. PAP mutants can be tested for enzymatic and anti-fungal activities using the assay procedures described in the working examples, below. A preferred PAP active site mutant is PAP (1-262, Glu176Val).

In regard to the disclosed PAP mutants, the phrase "which differs from wild-type PAP substantially in that . . . " means that except for the amino acid changes (described above), that are necessary to confer reduced phytotoxicity and anti-viral and/or anti-fungal activity, the amino acid sequences of the mutant PAPs are substantially identical to that of mature PAP. By the term "substantially identical," it is meant that the PAP mutants of the present invention can be further modified by way of additional substitutions, additions or deletions provided that the resultant PAP mutant retains reduced phytotoxicity and PAP biological activity as defined herein. For example, the N-terminus of the mutant PAP may be changed to a methionine residue, either by substitution or addition, to allow for expression of a DNA encoding the mutant PAP in various host cells particularly *E. coli*. The PAP mutants of the present invention may further include the N-terminal 22-amino acid signal peptide of wild-type PAP and/or the 29-amino acid C-terminal extension, both of which are shown in Table I above.

DNAs encoding the mutant PAPs of the present invention can be prepared by manipulation of known PAP genes. See Ausubel et al. (eds.), Vol. 1, Chap. 8 in *Current Protocols in Molecular Biology*, Wiley, N.Y. (1990). The DNAs may also be prepared via PCR techniques. See *PCR Protocols*, Innis et al. (eds.), Academic Press, San Diego, Calif. (1990). The mutant PAP-encoding DNA (e.g., a cDNA) is preferably inserted into a plant transformation vector in the form of an expression cassette containing all of the necessary elements for transformation of plant cells. The expression cassette typically contains, in proper reading frame, a promoter functional in plant cells, a 5' non-translated leader sequence, the mutant PAP DNA, and a 3' non-translated region functional in plants to cause the addition of polyadenylated nucleotides to the 3' end of the RNA sequence. Promoters functional in plant cells may be obtained from a variety of sources such as plants or plant DNA viruses. The selection of a promoter used in expression cassettes will determine the spatial and temporal expression pattern of the construction in the transgenic plant. Selected promoters may have constitutive activity and these include the CaMV 35S promoter, the actin promoter (McElroy et al., Plant Cell 2:163–171 (1990); McElroy et al., Mol. Gen. Genet. 231:150–160 (1991); Chibbar et al., Plant Cell Rep. 12:506–509 (1993), and the ubiquitin promoter (Binet et al., Plant Science 79:87–94 (1991), Christensen et al., Plant Mol. Biol. 12:619–632 (1989); Taylor et al., Plant Cell Rep. 12:491495 (1993)). Alternatively, they may be wound-induced (Xu et al., Plant Mol. Biol 22:573–588 (1993), Logemann et al., Plant Cell 1:151–158 (1989), Rohrmeier and Lehle, Plant Mol. Bio. 22:783–792 (1993), Firek et al., Plant Mol. Biol. 22:129–142 (1993), Warener et al., Plant J. 3:191–201 (1993)) and thus drive the expression of the mutant PAP gene at the sites of wounding or pathogen infection. Other useful promoters are expressed in specific cell types (such as leaf epidermal cells, meosphyll cells, root cortex cells) or in specific tissues or organs (roots, leaves or flowers, for example). Patent Application WO 93/07278, for example, describes the isolation of the maize trpA gene which is preferentially expressed in pith cells. Hudspeth and Grula, Plant Mol. Biol. 12:579–589 (1989), have described a promoter derived from the maize gene encoding phosphoenolpyruvate carboxylase (PEPC) with directs expression in a leaf-specific manner. Alternatively, the selected promoter may drive expression of the gene under a light-induced or other temporally-regulated promoter. A further alternative is that the selected promoter be chemically regulated. The DNAs may also encode the N-terminal signal sequence and/or the C-terminal extension of wild-type PAP.

A variety of transcriptional cleavage and polyadenylation sites are available for use in expression cassettes. These are responsible for correct processing (formation) of the 3' end of mRNAs. Appropriate transcriptional cleavage and polyadenylation sites which are known to function in plants include the CaMV 35S cleavage and polyadenylation sites, the tml cleavage and polyadenylations sites, the nopaline synthase cleavage and polyadenylation sites, the pea rbcS E9 cleavage and polyadenylation sites. These can be used in both monocotyledons and dicotyledons.

Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop 1:1183–1200 (1987)). In the same experimental system, the intron from the maize bronze-l gene had a similar effect in enhancing expression (Callis et al., supra.). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic mottle Virus (MCMV), and Alfalfa Mosaic Virus (AMV) have been shown to be effective in enhancing expression (e.g. Gallie et al., Nucl. Acids Res. 15:8693–8711 (1987); Skuzeski et al., Plant Mol. Biol. 15:65–79 (1990)).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformations include the nptII gene which confers resistance to kanamycin (Messing and Vierra, Gene 19:259–268 (1982); Bevan et al., Nature 304:184–187 (1983)), the bar gene which confers resistance to the herbicide phosphinothricin (White et al., Nucl. Acids Res. 18:1062 (1990); Spencer et al., Theor. Appl. Genet. 79:625–631 (1990)), the hph gene which confers resistance to the antibiotic hygromycin (Blochinger & Diggelmann, Mol. Cell Biol. 4:2929–2931 (1984)), and the dhfr gene, which confers resistance to methotrexate. Vectors suitable for Agrobacterium transformation typically carry at least one T-DNA border sequence. These include vectors such as pBIN19 (Bevan, Nucl. Acids Res. (1984) and pCIB200 (EP 0 332 104).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. For example, pCIB3064 is a pUC-derived vector suitable for the direct gene transfer technique in combination with selection by the herbicide basta (or phosphinothricin). It is described in WO 93/07278 and Koziel et al. (Biotechnology 11:194–200 (1993)).

An expression cassette containing the mutant PAP gene DNA containing the various elements described above may be inserted into a plant transformation vector by standard recombinant DNA methods. Alternatively, some or all of the elements of the expression cassette may be present in the vector, and any remaining elements may be added to the vector as necessary.

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described in Paszkowski et al., EMBO J 3:2717–2722 (1984), Potrykis et al., Mol. Gen. Genet. 199:169–177 (1985), Reich et al., Biotechnology 4:1001–1004 (1986), and Klein et al., Nature 327:70–73 (1987). In each case the transformed cells are regenerated to whole plants using standard techniques.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend on the complement of vir genes carried by the host Agrobacterium strain either on a co-resident plasmid or chromosomally (e.g. strain CIB542 for pCIB200 (Uknes et al. Plant Cell 5:159–169 (1993)). The transfer of the recombinant binary vector, to Agrobacterium is accomplished by a triparental mating procedure using *E. coli* carrying the recombinant binary vector, a helper *E. coli* strain which carries a plasmid such as pRK2013 which is able to mobilize the recombinant binary vector to the target Agrobacterium strain. Alternatively, the recombinant binary vector can be transferred to Agrobacterium by DNA transformation (Hofgen & Willmitzer, Nucl. Acids Res. 16:9877 (1988)).

Transformation of the target plant species by recombinant Agrobacterium usually involves co-cultivation of the Agrobacterium with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantages of avoiding complex vector construction and generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093–1096 (1986)).

Published European Patent Applications EP 0 292 435 and EP 0 392 225, and PCT application WO 93/07278 describe techniques for the preparation of callus and protoplasts of maize, transformation of protoplasts using PEG or electroporation, and the regeneration of maize plants from transformed protoplasts. Gordeon-Kamm et al., Plant Cell 2:603–618 (1990), and Fromm et al., Biotechnology 11:194–200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange et al., Plant Cell Rep. 7:739–384 (1988); Shimamoto et al., Nature 338:274–277 (1989); Datta et al., Biotechnology 8:736–740 (1990)). Both types are also routinely transformable using particle bombardment (Christou et al., Biotechnology 9:957–962 (1991)).

Patent Application EP 0 332 581 described techniques for the generation, transformation and regeneration of Pooideae protoplasts. Furthermore wheat transformation has been described by Vasil et al. (Biotechnology 10:667–674 (1992)) using particle bombardment into cells of type C long-term regenerable callus, and also by Vasil et al. (Biotechnology 11:1553–1558 (1993)) and Weeks et al. (Plant Physiol.

102:1077–1084 (1993)) using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); and U.S. Pat. Nos. 4,849,355 and 4,663,292.

The thus-transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See, e.g., Newell et al., Plant Cell Rep. 10:30–34 (1991) (disclosing potato transformation by stem culture).

The mutant PAP encoding DNAs of the present invention confer broad spectrum fungus and virus resistance to any plant capable of expressing the DNAs, including monocots (e.g., cereal crops) and dicots. Specific examples include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax and coffee.

PAP mutants other than those specifically described above can be identified by a selection system in eukaryotic cells. In a preferred embodiment, a PAP-encoding DNA molecule, operably linked to an inducible promoter functional in the eukaryotic cell, is randomly mutagenized in accordance with standard techniques. The cell is then transformed with the mutagenized PAP construct. The thus-transformed cell is then cultured in a suitable medium for a predetermined amount of time, e.g., sufficient to cause some growth of the cells, at which time an inducer is added to the medium to cause expression of the mutagenized DNA molecule. If the cultured cell survives the induction of the expression of the mutagenized PAP DNA molecule, which indicates that the mutagenesis resulted in the expression of a non-toxic PAP mutant, the PAP mutant can be then assayed in vitro or in vivo to determine whether it retains PAP biological activity. Preferred in vitro assays include eukaryotic translation systems such as reticulocyte lysate systems wherein the extent of the inhibition of protein synthesis in the system caused by the PAP mutant is determined. Preferred host cells are yeast cells such as *Saccharomyces cerevisiae*, as described in greater detail in Example 1, below. This method can also be conducted with a plurality of randomly mutagenized PAP-encoding DNA molecules. The PAP mutants identified as having reduced phytotoxicity and which retain PAP anti-viral and/or anti-fungal activity, as determined by subsequent assays, can then be isolated, purified and sequenced in accordance with standard techniques.

In another embodiment, the mutagenesis is performed after the transformation of the eukaryotic cell. The disadvantage with mutagenizing the DNA after transformation is that the chromosomal DNA of the host can also be mutagenized. To determine whether the mutations of the surviving cells are chromosomal or plasmid-borne in nature, this embodiment requires the step of replacing the transforming PAP-encoding DNA with wild-type PAP-encoding DNA under the control of an inducible promoter, and growing the cells in the presence of the inducer. Mutants which retain the ability to grow are chromosomal mutants, whereas mutants which fail to grow are plasmid-borne (i.e., PAP) mutants.

The invention will be further described by reference to the following detailed examples. These examples are provided for purposes of illustration only, and are not intended to be limiting unless otherwise specified.

EXAMPLE 1

Construction of yeast expression vectors and analysis of PAP expression in yeast. The full length cDNAs corresponding to PAP and PAP-v disclosed in Lodge, and shown in Table I, were cloned into yeast expression vectors, under the control of the galactose inducible promoter, GAL1. *S. cerevisiae* was chosen as the expression system because yeast has the advantage of supplying eukaryotic cell-specific post-translational modifications. Since yeast ribosomes are sensitive to PAP, a regulated promoter was used to drive the expression of PAP. The cDNAs encoding PAP and PAP-v were cloned into the yeast expression vector pAC55, containing the selectable marker, URA3, as BglII/SmaI fragments under the control of the galactose inducible promoter pGal1. The vectors containing PAP (NT123) and PAP-v (NT124) were transformed into the yeast strain W303 (Mat a, ade2-1 trp1-1 ura3-1 leu2-3,112 his3-11, 15can1-100 ) (Bossie et al., Mol. Biol. C 3:875–93 (1992)), according to the procedure described in Ito et al., J. Bacteriol. 153:163–68 (1983), and transformants were selected on uracil minus medium with glucose at 30° C.

Yeast cells containing either NT123 (wild-type PAP) or NT124 (PAP-v) were grown in uracil minus medium with 2% raffinose at 30° C. for 48 h to a density of $5\times10^7$ cells/ml. PAP protein expression was induced by the addition of 2% galactose to half of the culture, while the other half of the culture was used as an uninduced control. The cells were allowed to grow for an additional 4 h and then collected by centrifugation at 10,000 g for 5 min. The cells were resuspended in RIPA buffer 9150 mM NaCl, 1% NP-40, 0.5% sodium deoxycholate, 0.1% SDS, 50 mM Tris-HCl, pH8) with protease inhibitors (0.1 $\mu$g/ml each of antipain, aprotinin, chymostatin, leupeptin, pepstatin) and lysed using glass beads (0.5 mm). Extracts were loaded on a 10% SDS-PAGE gel in accordance with the procedures described in Tomlinson, J. Gen. Virol., supra. Immunoblot analysis was performed by the enhanced chemiluminescence (ECL) method (Amersham), using antibodies against purified PAP.

Both PAP and PAP-v were expressed in yeast after galactose induction. Based on comparison with PAP protein standards, yeast cells containing the PAP plasmid (NT123) expressed both the mature form of PAP and a larger form, while cells containing the PAP-v (NT124) expressed predominantly the larger form and very low levels of the mature form. PAP was not detected in the culture medium. While not intending to be bound by any particular theory of operation, Applicant believes that these results suggest the following: (1) PAP is expressed as a precursor and processed to the mature form in yeast; and (2) PAP undergoes further processing in addition to the co-translational cleavage of the amino acid N-terminal signal peptide (Lodge) because the size of the mature PAP and the PAP expressed in yeast was found to be smaller than the expected size after the removal of the signal sequence.

In vitro translation and processing of PAP and PAP-v. To examine the processing of PAP in vitro, both constructs described in Example 1A were transcribed and translated in vitro using the T7 coupled reticulocyte lysate translation system in the presence of 35S-methionine with or without canine microsomal membranes (Promega). PAP and PAP-v cDNAs were cloned into the pGem3Z vector (Promega) downstream of the T7 promoter. An equal amount of DNA (1 μg) from each construct was transcribed and translated in vitro in the presence $^{35}$S-methionine, using the T7 coupled reticulocyte lysate translation system (Promega) with or without canine pancreatic microsomal membranes (Promega). Translation products were incubated with 0.2 mg/ml proteinase K in the presence of 5 mM EDTA and 125 mM sucrose for 90 min. Proteinase K was inactivated by addition of 4 mM PMSF and incubation at room temperature for 2 hours. Translation products were then treated with Endo-H (endo-N-acetylglucosaminidase) (1 mU/10 μl) in the presence of 0.1% SDS and 0.1M sodium citrate pH 5.5, at 37° C. for 12 hours. Equal amounts of protein (3.5 μl) were analyzed on 10% SDS-PAGE in accordance with the procedure described in Laemmli et al., Nature (London) 227:680–685 (1970).

PAP and PAP-v encode precursor proteins of 33 and 34 kD, respectively, and both precursors are processed to a 32 kD form after incubation with membranes. The processed proteins are still larger than the mature form (29 kD), indicating that the PAP precursor undergoes further post-translational processing. PAP does not contain any N-linked glycosylation sites and the size of the in vitro translated proteins did not change after treatment with Endo-H, which removes carbohydrate. These results indicated that the PAP precursors contain an N-terminal signal sequence which is co-translationally processed, and another sequence, which is post-translationally removed. Further evidence for C-terminal processing was obtained from X-ray structure analysis, which showed that mature PAP is 29 amino acids shorter at its C-terminus than the sequence predicted from the cDNA. See Monzingo et al., J. Mol. Biol. 233:705–715 (1993).

Growth of transformed yeast: In the presence of 2% raffinose, a non-repressing, non-inducing carbon source relative to GAL gene expression, the growth of yeast transformants containing NT123 or NT124 was indistinguishable from the transformants containing the vector alone. Growth of transformed yeast containing NT123 was arrested upon addition of the inducer, galactose, to the medium. Cells containing NT123 or NT124 did not grow on plates containing galactose. In the liquid medium, however, the extent of inhibition was greater with NT123 than NT124, possibly due to lower levels of mature PAP produced in yeast containing NT124. PAP expression was detected within 2 h of galactose addition to the medium. Maximal levels were reached in 6 to 8 h. Immunoblot analysis using antibodies against PAP, detected a maximal PAP level of 1 μg/mg yeast protein in NT123 transformants and 250 ng/mg yeast protein in NT124 transformants. These results were consistent with production of active PAP in yeast.

Mutagenesis of PAP plasmids. To isolate PAP mutants nontoxic to yeast, the expression plasmids containing PAP (NT123) or PAP-v (NT124) were mutagenized using hydroxylamine, transformed into yeast and cells were plated on medium containing glucose and replica plated to galactose containing plates. About 10 μg of the purified plasmid DNA were added to 500 μl of freshly prepared hydroxylamine solution (0.35 g hydroxylamine-HCl and 0.09 g NaOH in 5 ml of water) and incubated at 37° C. for 20 h. To stop the mutagenesis, 10 μl of 5M NaCl, 50 μl of 1 mg/ml BSA and 1 ml of 100% ethanol were added and the mutagenized DNA was precipitated by incubation at −70° C. for 10 minutes. The DNA was resuspended in TE and precipitated again. The DNA was then transformed into yeast and plated on uracil minus medium containing 2% glucose and replica plated on medium containing 2% galactose. The colonies that grew on galactose were analyzed for PAP expression by ELISA described in Lodge and by immunoblot analysis to identify the mutants which expressed hydroxylamine generated mutant PAP.

Growth of mutant yeast: Growth of mutants derived from NT123 on galactose containing medium was indistinguishable from growth on raffinose containing medium. Similar results were obtained with mutants derived from NT124. Analysis of protein accumulation in yeast indicated that the expression of wild type PAP, but not the hydroxylamine generated mutant PAP, resulted in decreased protein accumulation in yeast (data not shown).

After mutagenesis, the colonies growing on uracil deficient galactose plates were analyzed for PAP expression by ELISA using PAP antibodies and the positives were further analyzed by immunoblot analysis. Of a total of 28 mutants from NT123 mutagenesis, six different isolates expressed proteins which cross-reacted with PAP antibodies. Out of 44 mutants isolated from NT124 mutagenesis, 24 different isolates produced proteins which cross-reacted with PAP antibodies. Four mutants (HMNT123-1, 124-6, 124-7, and 124-1) produced proteins which were larger than the mature form of PAP (29 kD), suggesting that the processing of PAP to the mature form is blocked in these mutants. Two mutants (HMNT123-2 and 123-3) produced proteins that co-migrated with the mature form of PAP, while several others (HMNT123-4, 123-5, 123-6, 124-2 and 124-3), produced smaller proteins. The protein expression levels in the mutants ranged from 0.005 to 0.08% of total soluble protein.

Nucleotide sequence analysis of PAP mutants: The positions of the amino acid alterations in the PAP mutants were identified by sequence analysis of the plasmids rescued from yeast. Plasmids were isolated from the mutants, transformed into *E. coli* according to the procedure set forth in Rose et al., supra, and sequenced using the Sequenase 2.0 DNA sequencing kit (ISB). See Robzyk et al., Nucl. Acids Res. 20, 3790 (1992). Sequence analysis of HMNT123-2 revealed that it contains a single point mutation, changing the glutamic acid at position 176 to valine(E176V) at the putative active site (Table II). HMNT123-2 produced a protein of the same size as the wild type PAP. Glutamic acid at position 176 (E176) is highly conserved among all RIPs sequenced to date and it is proposed to be at the active site cleft of PAP. See Stevens et al., Experientia 37:257–259 (1981). HMNT123-6, HMNT124-2 and HMNT124-3 all had a point mutation near the C-terminus which introduced a stop codon instead of a tryptophan at position 237 (W237) (Table II). As a result of this mutation, 26 amino acids were deleted from the C-terminus of the mutant PAP, and a truncated protein was produced. HMNT123-5 contained a frameshift mutation, which deleted two nucleotides (GA) at about the codon for Glu 184 (GAG), whereby the reading frame was altered and the Asn190 codon became TAA, because the reading frame shifted to the −1 position, resulting in expression of a truncated protein. A point mutation in HMNT124-1 changed the glutamic acid at position 97 to lysine (E97K) (Table I). HMNT123-1 also contained a single point mutation, at position 75, changing glycine to valine (G75V). Both of these mutants expressed a larger protein than purified mature PAP, suggesting that processing of PAP is inhibited in these mutants.

To confirm that the observed mutant phenotypes were due to the mutations identified in the PAP sequence, and not due to a chromosomal mutation, each mutant PAP plasmid was isolated and retransformed into the host strain, W303, and URA+transformants were selected. These transformants grew at wild type rates on galactose containing medium, indicating that the ability of the transformants to survive induction of PAP expression is plasmid-linked.

TABLE II

Mutations which abolish the toxicity of PAP to eukaryotic cells

| | |
|---|---|
| HMNT123-1 | Gly-75 (GGT) --> Val (GTT) |
| HMNT123-2 | Glu-176 (GAG) --> Val (GTG) |
| HMNT123-4 | Trp-208 (TGG) --> Stop (TAG) |
| HMNT123-5 | Glu-184 (GAG) --> Glu (GAA) |
| HMNT123-6 | Trp-237 (TGG) --> Stop (TAG) |
| HMNT124-1 | Glu-97 (GAA) --> Lys (AAA) |
| HMNT124-2 | Trp-237 (TGG) --> Stop (TAG) |
| HMNT124-3 | Trp-237 (TGG) --> Stop (TAG) |
| HMNT124-13 | Leu-202 (CTT) --> Phe (TTT) |

Enzymatic activity of PAP mutants: An in vitro translation assay was used to compare the enzymatic activity of PAP mutants. Brome mosaic virus (BMV) RNA was translated in the rabbit reticulocyte lysate system (Promega) in the presence of extracts from yeast containing different amounts of PAP, as described in Lodge. PAP levels in yeast were quantitated by ELISA (Lodge). The inhibition curves were linear in the range of 0.1 to 1 ng PAP/ml. Table III shows the results of the protein synthesis inhibition assay carried out in the presence of 0.2 ng/ml PAP from yeast. The amount of total protein and PAP were adjusted to 87 ng/ml and 0.2 ng/ml, respectively in each extract by adding either wild type yeast extract or RIPA buffer. In previous experiments, when in vitro translation was performed in the presence of 0.2 ng/ml BSA, no inhibition of translation was observed. When 0.2 ng/ml protein from nontransformed yeast (WT) were added, a slight inhibition of translation was observed. Translation was inhibited in the presence of 0.2 ng/ml of: (1) purified PAP added to wild type yeast extract (WT+PAP); (2) protein extracts from yeast containing NT123 or NT124; and (3) protein extracts from yeast containing the hydoxylamine generated mutants HMNT123-3, HMNT124-1, HMNT124-3 and HMNT124-13. In contrast, protein extracted from HMNT123-2 did not inhibit protein synthesis in the reticulocyte lysate system. Similar results were obtained when in vitro translation experiments were performed using 0.1 ng/ml PAP.

TABLE III

Inhibition of protein synthesis by PAP mutants

| Protein added to translation medium | Protein synthesis (cpm incorporated) |
|---|---|
| No RNA | 2,246 +/- 204 |
| BSA | 244,956 |
| WT | 176,723 ± 713 |
| PAP+WT | 146,660 ± 2474 |
| NT123 | 110007 ± 445 |
| HMNT123-2 | 213 952 ± 767 |
| HMNT123-3 | 134,202 ± 5522 |

TABLE III-continued

Inhibition of protein synthesis by PAP mutants

| Protein added to translation medium | Protein synthesis (cpm incorporated) |
|---|---|
| HMNT124 | 84,959 ± 661 |
| HMNT124-1 | 119529 ± 2094 |
| HMNT124-3 | 132,955 ± 3739 |
| HMNT124-13 | 145,899 ± 4457 |

EXAMPLE 2

Expression of PAP Mutants in Transgenic Tobacco

Mutant PAPs were engineered for constitutive expression in plants to determine if they would be non-toxic to plants, and if they could retain PAP antiviral properties.

In order to insert the PAP genes into the plant expression vectors, the plasmid DNA encoding the mutant PAPs was isolated from yeast, transformed into *E. coli* as described in the Example 1. The plasmid DNA encoding the mutant PAPs was isolated from *E. coli* digested with HindIII, the HindIII site was filled in with klenow DNA polymerase and the plasmid was digested with SacI to isolate the 772 bp SacI/HindIII fragment encoding the mutant PAP. The SacI/HindIII fragments encoding the mutant PAPs were cloned into pMON8443 (Lodge) after digestion with SacI and SmaI to remove the wild type PAP cDNA inserts. The SacI/HindIII fragment from HMNT123-2 was cloned into SacI/SmaI digested pMON8443 to generate NT144 and the SacI/HindIII fragment from HMNT124-3 was cloned into SacI/SmaI digested pMON8443 to generate NT145. NT146 and NT147 were generated by replacing the 772 bp SacI/HindIII fragment of the wild type PAP cDNA insert in pMON8443 with the 772 bp SacI/HindIII fragment of HMNT123-2 and HMNT124-3, respectively.

Plasmids NT144, NT145, NT146 and NT147 were mobilized into the ABI strain of *Agrobacterium tumefaciens* for transformation into tobacco and potato (Lodge). For transformation of *N. tabacum*, young leaves from one month-old tobacco plants were covered with water for 20–30 min. The water was drained off and the leaves were covered with 10% chlorox and 0.04% Tween 20 for 15 minutes and then rinsed three times with water. Leaf disks were cut with an autoclaved single hole punch and placed upside down on MS104 medium (4.4g/l MS salts, 30 g/l sucrose, B5 vitamins, 0.1 mg/l NAA and 1.0 mb/l BA) for 1 day for preculture. The precultured disks were placed in a 50 ml tube and inoculated with an overnight culture of Agrobacterium that was diluted 1:5. The tube was inverted several times. The disks were then taken out and blotted on sterile filter paper and placed upside down on MS104 feeder plates with a filter disk to co-culture for 2 days. Leaf disks were then transferred to MS104 media with selection (100 μg/ml kanamycin and 300 μg/ml cefataxime) and placed in an incubator. Calli and shoots appeared in about three weeks. Shoots were transferred to plantcons with MSO media (4.4 g/l MS salts, 30 g/l sucrose and B5 vitamins) with selection. Roots formed in two weeks, rooted shoots were then transferred to soil and kept in a high humidity environment. The regenerated plants were then screened by ELISA for the presence of neomycin phosphotransferase (NPTII) to identify the expressors.

Transformation frequencies of *N. tabacum* cv Samsun typically range between 10 to 12% (number of transgenic plants obtained per leaf disk). As previously reported the transformation frequency of *N. tabacum* was significantly reduced when vectors containing the wild type PAP (pMON8443) or the variant PAP (pMON8442) were used in transformation (Lodge). In contrast, as shown below in Table IV, no decrease in transformation frequency was observed when vectors containing the nontoxic mutant PAPs were used in the transformation.

TABLE IV

| Plasmid | Frequency of transformation |
|---|---|
| NT144 | 13% |
| NT145 | 11% |
| NT147 | 12% |

As previously reported, the transgenic plants expressing wild type PAP or the variant PAP showed growth reduction, chlorosis and mottling on their leaves (Lodge). In contrast, the transgenic plants expressing the mutant PAPs were phenotypically normal. They grew at the same rate as the wild type plants and showed no chlorosis or mottling on their leaves, indicating that the expression of the mutant PAPs is not toxic to transgenic plants. The mutant PAPs were also expressed in *E. coli* and their expression did not affect the growth rate of *E. coli* cells, indicating that they are not toxic to *E. coli.*

EXAMPLE 3

Antiviral Activity of Mutant PAP Expressed in Transgenic Tobacco

Transgenic tobacco (*N. tabacum* cv Samsun) plants were assayed by ELISA (Lodge) to determine the level of expression of the mutant PAPs. In Table V, the level of expression of the mutant PAP is compared with the level of expression of the variant PAP (pMON8442) (Lodge) expressed in transgenic plants.

TABLE V

Level of PAP expression in transgenic tobacco

| Plant number | Level of expression |
|---|---|
| NT144-12 | 1.5 μg/mg |
| NT144-13 | 0.9 μg/mg |
| NT145-13 | 4.4 ng/mg |
| pMON8442(26139-11) | 9.6 ng/mg |

As shown in Table V, the transgenic plant containing the C-terminal deletion mutant (NT145-13) expressed similar levels of mutant PAP as the plant expressing the PAP variant (pMON8442) (Lodge). In contrast, transgenic plants containing the active site mutant (NT144) expressed significantly higher levels of the mutant PAP.

To test if the PAP mutants (the NT144 and NT145 constructs) had antiviral activity in vitro, wild type tobacco plants were inoculated with potato virus X (PVX) in the presence of protein extracts from plants expressing the mutant PAP, the PAP-v (pMON8442) and nontransformed (wild type) tobacco. PAP levels in the transgenic plants were quantitated by ELISA. The level of PAP expression in line 145-13 was 4.4 ng/mg and the level of PAP expression in line 144-12 was 1.5 μg/mg. Plants were inoculated with extracts from transgenic plants containing 5 ng PAP per leaf and 1.1 mg total protein. Protein extract was prepared from nontransformed tobacco leaves (WT). Fifty μl of 1 g/ml PVX was inoculated onto tobacco leaves in the presence of different amounts of total protein from nontransformed tobacco, ranging from 6.7 μg to 1.1 mg. Twenty tobacco plants were inoculated with 50 μl of 1 μg/ml PVX in the presence of 6.7 μg–1.1 mg of total protein from nontransformed plants. As shown in Table VI, all WT plants became infected with PVX and showed local lesions, systemic symptoms and virus accumulation in the leaves above the inoculated leaves (systemic leaves). These results demonstrate that protein extracts from nontransformed tobacco plants do not have any effect on PVX infection. When protein extract from nontransformed tobacco plants was used in the presence of 5 and 10 ng purified PAP (WT+PAP), lower numbers of PVX lesions were observed on inoculated leaves, indicating that tobacco plants were protected from PVX infection in the presence of purified PAP. However, although fewer lesions were obtained on the inoculated leaves of these plants, they showed systemic symptoms and similar levels of PVX antigen as the plants inoculated with PVX in the presence of extracts from nontransformed tobacco plants (WT).

TABLE VI

Effects of PAP mutants on PVX infection of tobacco leaves[1].

| Plant Extract[a] level (ng/mg)[c] | PAP ng/(leaf) | mean no. of lesions[b] | PVX antigen |
|---|---|---|---|
| WT[d] | 0 | 66.6 ± 10.1 | 4.4 ± 1.4 |
| WT + PAP[e] | 5 | 9.0 ± 2.0 | 3.1 ± 1.9 |
| | 10 | 1.5 ± 2.0 | 2.8 ± 2.6 |
| 26139 | 5 | 1.8 ± 2.9 | NA |
| 145-13 | 5 | 12.5 ± 7.4 | 0.2 ± 0.3 |
| 144-12 | 5 | 57.8 ± 7.4 | 3.2 ± 2.5 |
| | 10 | 56.1 ± 4.9 | 2.5 ± 1.4 |
| | 20 | 55.5 ± 13.8 | 4.3 ± 1.4 |
| | 50 | 53.3 ± 14.9 | 2.8 ± 0.3 |
| | 100 | 68.0 ± 11.7 | 3.0 ± 0.9 |

[a]Plant extract was prepared from either non-transformed or transformed tobacco leaves with plant expression vector (pMON8442, NT145, and NT144).
[b]The number of lesions were counted at 9 days post-inoculation.
[c]Three leaf discs in a tube were taken from 1st, 2nd and 3rd systemic leaves at 12 days post inoculation and then homogenized in ELISA buffer. The average levels of PVX antigen were quantified by ELISA. The amount of total proteins in each extract were quantified by BCA reagent (Pierce).
[d]Protein extract was made from non-transformed tobacco leaves.
[e]PAP (Calbiochem) was added to a protein extract from non-transformed tobacco leaves.
[1]Twenty plants for wild-type(wt), ten plants for wt + PAP and five plants for each transgenic protein extract were used. Two leaves from each plant were inoculated with 50 μl of PVX (1 μg/ml) in the presence of different amount of PAP or PAP mutants.

When PVX was inoculated in the presence of 5 ng protein from the transgenic plant (26139) expressing the variant PAP (pMON8442), significantly lower numbers of lesions were observed on the inoculated leaves and these plants escaped systemic infection. Similarly, when PVX was inoculated in the presence of 5 ng protein from transgenic plant (145-13) expressing the C-terminal deletion mutant, significantly fewer lesions were obtained. These plants did not show systemic symptoms and the PVX antigen levels were significantly reduced on the inoculated leaves. In contrast, when PVX was inoculated in the presence of 5 to 100 ng protein from transgenic plant expressing the active site mutant (144-12), the numbers of lesions observed on the inoculated leaves was similar to the numbers of lesions observed on plants inoculated in the presence of protein from nontransformed tobacco plants (WT). Systemic symptoms were observed on these plants and PVX antigen levels in the systemic leaves were comparable to the antigen levels in plants inoculated with PVX in the presence of extracts from nontransformed tobacco plants. These results demonstrate that the C-terminal deletion mutant which is enzymatically active in vitro retains its antiviral activity in vitro. In contrast, the active site mutant which is enzymatically inactive in vitro, does not retain its antiviral activity in vitro, suggesting that the enzymatic activity of PAP is critical for antiviral activity in vitro.

EXAMPLE 4

Expression of PAP Mutants in Transgenic Potato

Potato stems were cut into 3 mm pieces and placed in sterile water. Agrobacterium containing NT144, Nt145, NT146 and NT147 was grown overnight. Cells were spun down and resuspended in 10 ml of water. Agrobacterium was diluted again 1:10 in water. Water was removed from potato stem explants and the diluted Agrobacterium was added. The stem explants were incubated with Agrobacterium for 15 min. The bacteria were removed and the explants were placed on 1/10 MSO plates that had been covered with sterile Whatman #1 filters. MSO contains 4.4 g MS salts, 30 g sucrose and 1 ml B5 vitamin (500×) in a 1 liter volume, pH 5.7. After a two day co-culture period in the dark, the explants were placed on PC media, containing MSO plus 0.5 mg/l zeatin riboside (ZR), 5 mg/l $AgNO_3$ and 0.1 mg/l NAA (naphthaleneacetic acid) 100 mg kanamycin and 300 mg cefataxime per liter, for four weeks. After 4 weeks, the explants were placed on PS media which contains MSO plus 5 mg/l ZR, 0.3 mg/l giberellic acid, 100 mg kanamycin and 300 mg cefataxime per liter. Shoots began to appear in four to eight weeks. Shoots were then removed and placed in plantcons containing PM media (4.4 g MS salts, 30 g sucrose, 0.17 g $NaH_2PO_4H_2O$, 1 ml thiamine HCl and 0.1 g inositol in a 1 liter volume, pH 6.0 and 0.2% gelrite agar). Plants were then placed in soil, hardened off and analyzed by NPTII ELISA to identify the transgenic plants. Transgenic potato plants were then analyzed by ELISA for PAP expression. Transgenic potato plants expressing NT144, NT145 and NT146 were identified by ELISA. The transformation frequencies were not affected when constructs containing mutant PAPs were used and the transgenic plants expressing mutant PAPs were phenotypically normal, indicating that the expression of the mutant PAPs is not toxic to potato.

EXAMPLE 5

Expression of PAP Mutants in Transgenic Turfgrass

Mutant PAPs were engineered for constitutive expression in monocots. Creeping bentgrass (*Agrostis palustris*, Huds.), which is a turfgrass used in golf courses, fairways, tees and lawns, was used as the monocot species for transformation. In order to construct an expression vector for monocots, NT168 was created by cloning the promoter and the first intron of the maize ubiquitin gene (Toki et al., Plant Physiol. 100:1503–1507 (1992)) into pMON969. pMON969 was digested with HindIII and BglII to remove the CaMV 35S promoter region. The plasmid pAHC20, containing the ubiquitin promoter and the first intron (Toki) was digested with HindIII and BamHI to isolate the 2016 bp HindIII/BamHI fragment which was ligated to HindIII/BglII fragment of pMON969 to generate NT168. The cDNA fragments encoding the mutant PAPs were isolated by digesting NT144 and NT145 with BglII and BamHI and cloned into the BamHI site of NT168. The monocot expression vectors containing the mutant PAP cDNAs were then used in transformation along with pSL12011, which contains the selectable marker, the bar gene (Hartmann et al., Biotechnology 12:919–923 (1994). Turfgrass transformation was carried out using two different methods, biolistic transformation using the particle gun and by protoplast transformation as described below.

Embryogenic callus cultures were initiated from surface sterilized seeds of 7 creeping bentgrass cultivars: ‘Cobra’, ‘Emerald’, ‘PennLinks’, ‘Providence’, ‘Putter’, ‘Southshore’, and ‘SR1020’ and used in biolistic transformation, as described in Hartmann. Callus initiation media were MS basal medium and MS vitamins, supplemented with 100 mg $L^{-1}$ myo-inositol, 3% sucrose, and either 150 mg $1^{-1}$ asparagine and 2 mg $L^{-1}$ 2,4-D for MSA2D, Or 500 mg $L^{-1}$ casein hydrolysate, 6.6 mg $L^{-1}$ dicamba, and 0.5 mg $L^{-1}$ 6-BA for MMS. Media were solidified with 0.2% Phytagel® (Sigma). After 4 to 6 weeks in the dark at 25° C., embryogenic callus lines were selected and transferred to fresh medium. Suspensions were established from embryogenic callus cultures by adding 1 to 2 g callus to 250 ml flasks with 50 ml liquid media, incubate in the dark at 25° C. with shaking at 120 rpm and subcultured twice a week.

Plates were prepared for particle bombardment by placing 1 ml of suspension cells on 5.5 cm filter disks in plates containing MSA2D media with the addition of 0.4 M mannitol. Plates were prepared 20 h prior to bombardment and kept in the dark. Gold particles were prepared by heating at 95° C. in 100% ethanol for 30 min, centrifuged briefly and resuspended in fresh ethanol. The particles were sonicated for 10–30 min in a water bath, washed 3 times in sterile, distilled water, and resuspended in water. DNA samples consisting of 50 μl (5 mg) gold suspensions, 10 μg target DNA, 50 μl 2.5M $CaCl_2$, and 20 μl 0.1 M spermidine, were vortexed, centrifuged, and resuspended in ethanol. The ethanol wash was repeated for a total of 3 times. The final pellet was resuspended in 30 μl ethanol, and 5 μl of DNA solution were used per shot. Bombardment was carried out using the Bio-Rad PDS-1000, He Biolistic Delivery System at 1100 psi. Calli from the bombardment experiments were plated out on MSA2D medium containing 2 or 4 mg/l of bialaphos for selection 34 days after bombardment and continued for 8 wks without transfer. After 8 wks on plate selection, calli were transferred to MS media without hormones for regeneration. Regenerates appeared within 2–8 wks. Shoots were transferred to Plantcons containing MS medium and roots appeared within 24 wks.

For protoplast transformation, protoplast isolation was performed four days after subculture. Cells were incubated with filter-sterilized enzyme solution containing 1% (w/v) Cellulase Onozuka RA (Yakult Pharmaceutical Co. LTD), 0.1% Pectolyase Y-23 (Seishin Pharmaceutical Co. LTD), and 0.1% MES (2-[N-morpholino]ethane-sulfonic acid) (Sigma) in culture media (MSA2D or MMS with 5% mannitol) for 4 hours at 28° C. with shaking at 50 rpm. About 1 g fresh weight of suspension cultures was treated with 10 ml of enzyme solution. Protoplasts were filtered through Miracloth and washed twice with culture medium containing 5% mannitol. Mannitol was used as an osmotic stabilizing agent. Protoplasts were cultured using a feeder layer system). The washed, filtered protoplasts were pipetted onto a black nitrocellulose membrane placed over a feeder layer of suspension cells which had been spread on 5% mannitol culture medium. One week later, the membranes with protoplasts were transferred to a fresh feeder layer on 3% mannitol culture plates. Protoplasts were removed from the feeder layer 2 weeks after isolation. Plating efficiency was determined by dividing the number of visible colonies 3 weeks after isolation by the total number of protoplasts plated. Plants were regenerated by placing protoplast derived calli on MS medium without hormone or with 1 mg $L^{-1}$ 6-BA orkinetin. After 4 to 5 weeks shoots were transferred to Plantcon® 4 with MS medium containing no hormone for rooting. Protoplasts were transformed using either PEG or electroporation at 170 volts $cm^{-1}$ using a Gene-Pulster (Bio-Rad). In PEG experiments, freshly isolated protoplasts were resuspended at a density of $1\times10^7$ protoplasts per ml in 5% mannitol containing 15 mM $MgCl_2$ and 0.1% MES. Approximately 0.3 ml protoplasts were incubated with 20 to 40 μg plasmid DNA and 13% PEG for 10 to 15 min., diluted stepwise and resuspended in culture medium with 5% mannitol (pH 5.8) after centrifugation. In electroporation experiments, protoplasts were resuspended at a density of $5\times10^6$ protoplasts per ml in cold filter sterilized electroporation buffer containing 5.2 g $L^{-1}$ KCl, 0.835 g $L^{-1}$ $CaCl_2$, 0.976 g $L^{-1}$ MES and 5% mannitol at pH5.8. About 0.8 ml protoplasts were mixed with 20 μg DNA by inversion, electroporated at 170 volts $cm^{-1}$ and placed on ice for 15 min., then diluted to a total of 3 ml with culture medium containing 5% mannitol. Selection with 4 mg $L^{-1}$ of bialaphos was initiated 16 days after protoplast isolation and transformation. Resistant colonies were selected on MS medium without hormone, with 6-BA or kinetin as described above. Shoots were transferred to Plantcons® for rooting. A commercial formulation of bialaphos under the trade name Herbiace® (Meiji Seika Kaishya, LTD.) was used in greenhouse herbicide tests. Herbicide rates for Herbiace® were established using control plants, and were based on the commercial rate of 0.75 lb AI/acre (1× the field rate). The herbicide was applied to all the tillers above ground with an artist's paint brush at the rat of 120 ml per flat. Dimension of the flat is 0.1431 $m^2$ and it holds 96 or 24 plants.

EXAMPLE 6

Expression of the Mutants in Transgenic Tobacco Plants and Resistance to Viral Infection A. Expression of PAP Mutants in Transgenic Tobacco To determine if enzymatic activity of PAP is required for its antiviral activity, the cDNA encoding the active-site mutant NT123-2 was cloned into the plant expression vector pMON8443 after removing the wild type PAP insert, to generate NT144, as described in Example 2. Similarly, the cDNA encoding the C-terminal deletion mutant, NT124-3 was cloned into pMON8443 to generate NT145 and NT147, as described in Example 2. Expression of the mutant PAPs was driven by the enhanced CaMV3SS promoter. NT144, NT145 and NT147 were mobilized into *Agrobacterium tumefaciens* for transformation into tobacco. Transformation frequencies of *Nicotiana tabacum* cv Samsun typically range between 10 to 12% based on the number of transgenic plants obtained per leaf disk (Lodge). The transformation frequency was 13% using NT144 and 11% using NT145. The transgenic plants expressing the active-site mutant or the C-terminal deletion mutant were phenotypically normal. They grew at the same rate as wild type plants and did not show chlorosis or mottling in their leaves, indicating that the expression of the mutant PAPs was not toxic to transgenic tobacco. These results are in contrast to the previously reported results (Lodge) in which the transformation frequencies of *N. tabacum* were reduced to 0.7% when using a vector containing PAP (pMON8443), and to 3.7% when using a vector containing PAP-v (pMON8442), both of which are enzymatically active (Lodge). Lodge did not recover any transgenic plants expressing high levels of PAP, and the transgenic plants expressing high levels of PAP-v showed growth reduction, chlorosis, and mottling in their leaves.

Regenerated transgenic plants were first analyzed for expression of neomycin phosphotransferase (NPTII) by ELISA. The NPTII positive plants were then analyzed for PAP expression by ELISA and immunoblot analysis. Eleven different transgenic plants expressed detectable levels of the active-site mutant by ELISA. Plants expressing the active-site mutant PAP produced a 29 kDa protein which comigrated with mature PAP, indicating that the active-site mutant PAP is fully processed to the mature form in transgenic plants (data not shown). Transgenic plants expressed significantly higher levels of the active-site mutant than the plants expressing PAP or PAP-v. No bands corresponding to PAP were detected in wild type tobacco or in transgenic tobacco expressing β-glucuronidase. The C-terminal deletion mutant was expressed at significantly lower levels than the active-site mutant.

B. Antiviral Activity of the Active-site Mutant in Transgenic Tobacco

In order to determine if transgenic lines expressing the active-site mutant PAP are resistant to virus infection, progeny of transformed plant lines were inoculated with PVX. Self-fertilized progeny were screened for the presence of PAP by ELISA. PAP levels in the progeny of the transgenic lines varied depending on the age of plants and growth conditions. The degree of variability in PAP levels was similar to that previously reported for transgenic lines expressing PAP or PAP-v (Lodge). Ten progeny from each transgenic line expressing the active-site mutant PAP (144-1 and 144-7), PAP-v (26139-19), PAP (33617-11) and 10 nontransformed tobacco plants were inoculated with 1 μg/ml PVX. Symptom development on both inoculated and systemic leaves was monitored visually each day up to 21 days post-inoculation. In addition, disks from the inoculated leaves and from the first, second and third systemic leaves of each plant were sampled at 12 days post-inoculation in order to quantitate virus replication and spread.

As shown in Table VII, transgenic plants expressing PAP-v or the wild type PAP did not develop any lesions on the inoculated leaves at nine days post-inoculation. In contrast transgenic plants expressing the active-site mutant had as many lesions on their inoculated leaves as the control plants. ELISA analysis of systemic leaves showed that 90% of wild type tobacco plants were systemically infected by PVX at 12 days post-inoculation, while only 30 and 40% of the transgenic plants expressing PAP and PAP-v, respectively, showed systemic PVX infection. In contrast, 100% of the plants expressing the active-site mutant were infected with PVX (Table VII). Similar results were obtained when plants were scored again at 21 days post inoculation.

TABLE VII

| Plant Line | PAP expressed | Level of PAP (ng/mg)[a] | Number of lesions[b] | % of plants showing systemic infection[c] |
|---|---|---|---|---|
| WT | | 0 | 77 +/− 12 | 90 |
| 26139-19 | PAP-v | 5.6 +/− 2.6 | 0** | 30** |
| 33617-11 | PAP | 0.6 +/− 0.02 | 0** | 40* |
| 144-1 | E176V | 43.8 +/− 4.8 | 78 +/− 16 | 100 |
| 144-7 | E176V | 46.2 +/− 5.6 | 72 +/− 11 | 100 |

[a]PAP levels were quantitated by ELISA after taking four leaf disks from twenty plants per line. Mean values +/− SD are shown.
[b]Ten plants from each line were inoculated with 50 μl of 1 μg/ml PVX on two leaves per plant. The number of lesions were counted 9 days post inoculation. Mean values +/− SD are shown.
[c]Three leaf disks were taken from 1st, 2nd and 3rd systemically infected leaves at 12 days post inoculation and viral antigen levels were quantitated by ELISA. The amount of total protein in each extract was quantitated using the BCA kit (Pierce).
**Significantly different from wild type at 1% level
*Significantly different from wild type at 5% level To determine if transgenic plants expressing higher levels of the active-site mutant are also susceptible to PVX infection, homozygous progeny (R2 generation) of transgenic link 144-12, which expressed the highest levels of the active-site mutant PAP were inoculated with 0.5 μg/ml PVX. As shown in Table VIII below, transgenic lines producing high levels of the active-site mutant had the same numbers of lesions as the wild type tobacco plants in their inoculated leaves, while progeny of transgenic plants which expressed PAP-v or PAP had significantly lower numbers of lesions. ELISA analysis of the systemic leaves demonstrated that by 21 days post inoculation, 90% of wild type tobacco plants and 100% of the transgenic plants expressing the active site mutant were infected with PVX. In contrast, plants expressing PAP or PAP-v had fewer lesions on the inoculated leaves and lower percentages of these plants became systemically infected with PVX.

In additional experiments, progeny of seven different transgenic lines expressing the active-site mutant were analyzed for their susceptibility to PVX infection; none of these lines showed resistance to PVX (data not shown).

TABLE VIII

Susceptibility of transgenic tobacco plants expressing the C-terminal deletion mutant (W237Stop) to PVX infection

| Plant Line | PAP expressed | Level of PAP (ng/mg)[a] | Number of lesions[b] | % of plants showing systemic infection[c] 12 dpi | 21 dpi |
|---|---|---|---|---|---|
| WT | | 0 | 24 +/− 15 | 90 | 90 |
| 26139-19 | PAP-v | 9.6 | 1 +/− 2** | 10** | 30** |
| 33617-11 | PAP | 1.6 | 11 +/− 4** | 10* | 40* |
| 144-12 | E176V | 1500 | 23 +/− 13 | 100 | 100 |
| 147-19 | W237Stop | 4.5 | 12 +/− 10** | 20** | 60 |
| 145-13 | W237Stop | 4.4 | 6 +/− 4** | 30** | 60 |

[a]PAP levels were quantitated by ELISA in the primary transgenic plants.
[b]Eight to ten plants from the homozygous progeny (R generation) of each transgenic line were inoculated with 50 μl of 0.5 μg/ml PVX on two leaves per plant. The number of lesions were counted 12 days post inoculation. Mean values +/− SD are shown.
[c]Two leaf disks were taken from first and second systemically infected leaf from each plant at 12 days post-inoculation and two leaf disks were taken from third and fourth systemically infected leaf at 21 days post-inoculation. Viral antigen levels were quantitated by ELISA. The amount of total protein in each extract was quantitated using the BCA kit (Pierce).
**Significantly different from wild type at 1% level
*Significantly different from wild type at 5% level C. Antiviral Activity of C-terminal Deletion Mutant in Transgenic Tobacco In order to determine if transgenic lines expressing the C-terminal deletion mutant are resistant to virus infection, homozygous progeny (R2 generation) from transgenic lines 145-13 and 147-19 expressing the C-terminal deletion mutant (W237Stop) were inoculated with 0.5 μg/ml PVX and the numbers of lesions were counted at 12 days post-inoculation. As shown in Table VIII above, plants from transgenic lines 145-13 and 147-19 had significantly lower numbers of lesions on their inoculated leaves compared to the wild-type plants. At 12 days post inoculation, only 20 and 30% of the plants from the transgenic lines 147-19 and 145-13, respectively, showed systemic symptoms and contained PVX antigen by ELISA, while 90% of the control plants were infected with PVX. By 21 days post-inoculation, there was an increase in the percentage of plants from lines 147-19 And 145-13 that showed systemic symptoms. As observed in previous tests, progeny of transgenic lines expressing PAP-v and PAP were protected from PVX infection. Infected plants expressing the C-terminal deletion mutant (W237Stop), PAP or PAP-v showed milder symptoms compared to the infected wild-type plants or transgenic plants expressing the active-site mutant (E176V). ELISA analysis was used to quantitate viral antigen levels in transgenic plants and wild-type plants at 21 days post-inoculation. PVX antigen levels were lower in plants from lines 147-19, 145-13, and 33617-11 compared to the antigen levels wild type plants. The percentages of infected plants did not change when they were scored again at 4 weeks post inoculation.

In additional experiments, a total of six different transgenic lines expressing the C-terminal deletion mutant were analyzed for their susceptibility to PVX infection and four of these lines showed resistance to PVX infection (data not shown).

EXAMPLE 7

Analysis of Fungal Resistance in Transgenic Plants Expressing PAP and PAP Mutants Seedlings of transgenic tobacco lines expressing PAP, PAP mutants and wild-type tobacco seedlings were used. Four weeks after germination seedlings were transferred into growth chamber and were grown in the sterile soil at 25° C., 80% relative humidity, and 16-hour photoperiod. Recombinant constructs with chimeric PAP genes were introduced into *Agrobacterium tumefaciens* via triparental mating. Agrobacterium containing the modified PAP genes were used to transform *Nicotiana tabacum* cv. Samsun. Kanamycin resistant $R_2$ transgenic plants were self-pollinated, and $R_3$ seedlings were used in the experiments. Transgenic plants from lines 33617 (expressing wild type PAP), NT144 (expressing active-site mutant PAP), NT145, and NT147 (both expressing C-terminal deletion mutant PAP) were used.

Four week-old transgenic and control seedlings were transplanted into sterile soil and inoculated with soil-borne fungal pathogen *Rhizoctonia solani*. Development of disease symptoms was observed for two weeks and the seedling mortality rates were calculated. Plants that survived the fungal infection were transplanted into individual pots and samples of tissue were taken for further analysis.

Following inoculation with *R. solani*, control tobacco seedlings were very quickly overcome by fungal pathogen. The disease progressed rapidly, affecting more than 30% of control seedlings in six days post-inoculation. In contrast, the transgenic lines susceptibility to infection was significantly lower. Six days post-inoculation, only 9.5% of the seedlings from the lines with wild-type PAP, about 20% of seedlings from the C-terminal truncated PAP line, and 23% of the seedlings from the active-site mutant line were affected. The number of seedlings that survived at different time points is shown in Table IX below. All transgenic lines exhibited a delay in appearance of disease symptoms and a lower mortality rate.

TABLE IX

| Progression of disease in transgenic tobacco PAP lines infected with *Rhizoctonia solani.* | | | | |
|---|---|---|---|---|
| | Number of seedlings survived post-inoculation | | | |
| Tobacco line | 0 days (%) | 6 days (%) | 10 days (%) | 14 days (%) |
| wild type | 40 (100) | 27 (67.5) | 25 (62.5) | 25 (62.5) |
| 33617-11 | 42 (100) | 38 (90.5) | 35 (83.3) | 34 (81.0) |
| 145-15-3 | 37 (100) | 29 (78.4) | 26 (70.3) | 23 (62.2) |
| 147-19-25 | 39 (100) | 32 (82.1) | 29 (74.4) | 28 (71.8) |
| 144-12-3 | 39 (100) | 30 (76.9) | 29 (74.4) | 29 (74.4) |

In a separate experiment, with a different strain of *Rhizoctonia solani*, the disease progressed very rapidly, essentially killing the majority of seedlings in five days. Seedling survival after two weeks of growth in the infected soil is shown in Table X below. Noticeably, control plants, although not dead at the scoring time point, were extremely stunted, and exhibited very severe disease symptoms. In contrast, seedlings in transgenic lines with truncated PAP showed much less tissue damage.

TABLE X

| Survival of transgenic tobacco lines with different PAP genes in *Rhizoctonia solani* resistance test | | | |
|---|---|---|---|
| Tobacco line (Samsun) | Number of seedlings planted | Number of seedlings survived 14 days postinoculation | % seedlings survived 14 days postinoculation |
| control (n) | 20 | 2 | 10 |
| control (N) | 20 | 0 | 0 |
| 33617-11 | 20 | 8 | 40 |
| 144-12 | 20 | 5 | 25 |
| 145-15 | 20 | 1 | 5 |
| 147-19 | 20 | 5 | 25 |

Analysis of Surviving Plants

Analysis of the total cellular protein from transgenic lines was performed by separating protein samples on 10% SDS-PAGE using a Mini-PROTEAN II electrophoresis cell (Bio-Rad) and proteins were transferred onto nitrocellulose membrane using Bio-Rad Trans-Blot semi-dry electrophoretic transfer apparatus according to manufacturer's instructions. Western blot analysis was performed using PAP IgG or PR1a monoclonal antibodies. Detection was by enhanced chemiluminescence using DuPont Renaissance kit.

Western blot analysis of cellular extracts from transgenic plants showed that the PAP gene is expressed in all plants that survived the fungal infection. The amount of PAP produced differed among individual plants. In addition, apoplastic fluid was isolated from the same plants and extracellular proteins were analyzed by staining the native gel with silver nitrate. Expression of pathogenesis-related proteins (PR) was detected in plants expressing pokeweed antiviral protein gene. Western blot analysis also showed elevated levels of PR1a in surviving plants.

Significant reduction of fungal disease symptoms in transgenic tobacco lines expressing pokeweed antiviral protein was observed. As shown in Tables IX and X, transgenic lines with PAP exhibited greater percentage of seedling survival after infection by *R. solani*. In addition, the disease progression, represented by the rate of seedling mortality, was also slower in transgenic PAP lines. Transgenic line 33617, which expressed the wild type PAP, as well as transgenic tobacco lines that contained mutant forms of PAP, NT144-12 (which expresses the active site mutant PAP), NT145-15 and NT147-19 (which expressed a truncated form of PAP, lacking 25 C-terminal amino acids) showed resistance to fungal infection.

Expression of the mutant PAP genes in tobacco proved to have absolutely no detectable phenotypic effect but surprisingly led to the constitutive expression of several pathogenesis-related proteins. Some of the genes induced are known for their anti-fungal activity. In the light of this observation, and while not intending to be limited to any particular theory of operation, Applicant believes that the resistance to *Rhizoctonia solani* infection by tobacco lines expressing mutant PAP genes of the present invention may be explained by the action of the host defense genes, and that resistance to fungus infection in plants expressing PAP may be conferred by dual action of PAP transgene and a number of host genes, constitutively expressed in transgenic tobacco. Applicant further believes that the induction of these plant defense genes further serves to protect transgenic plants against other pathogens such as bacterial pathogens.

EXAMPLE 8

Isolation of New PAP Mutants by Chromosomal Mutagenesis and Selection in Yeast

A. Isolation of PAP Mutants

Chromosomal mutagenesis and selection were used to isolate yeast mutants which permit cells to grow in the presence of PAP. Constitutive expression of PAP in *S. cerevisiae* is normally lethal. Therefore, the PAP gene was placed under the control of the galactose inducible GAL1 promoter. This enables cells carrying the plasmid with the PAP gene to grow normally on glucose when PAP expression is repressed, but kills cells grown on galactose when PAP is expressed. We have taken advantage of having an inducible PAP expression system and the toxicity of PAP to normal yeast cells, to isolate mutants which can grow in the presence of PAP. Yeast cells carrying a plasmid with the wild-type PAP gene (NT123) were grown to early log phase, pH 7.0, at a density of $1\times10^8$ cells/ml. Three 1 ml aliquots were removed and used for the mutagenesis. Mutagenesis was performed using either 5 $\mu$l or 25 $\mu$l of ethyl methanesulfonate (EMS). An unmutagenized aliquot was kept as the control to examine the frequency of spontaneous mutants. Following the addition of EMS, the cells were incubated at 30° C. for 1 hour, with gentle shaking. The mutagenesis was terminated by the addition of 5% sodium thiosulfate. The cells were then plated on uracil deficient plates with 2% glucose and incubated at 30° C. Based on the number of colonies which arose on the plates from the mutagenized cells versus the unmutagenized control, 35% and 98% of the cells were killed with 5 $\mu$l and 25 $\mu$l of EMS, respectively. These colonies were replica plated to uracil deficient media with 2% galactose and screened for clonies capable of growing in the presence of PAP. Approximately 13,500 colonies were screened, and 9 colonies were obtained which were able to grow on galactose.

The mutants were tested to see if the mutations were chromosomal or plasmid linked. Plasmid segregation was performed on the mutants by growing the cells for approximately 50 generations in non-selective media (YEPD), plating them out on YEPD, followed by replica plating the colonies which, having lost the plasmid, can no longer grow on uracil deficient media. The plasmid segregated cells were transformed with fresh NT123 plasmid and examined for their ability to grow on uracil deficient media with 2% galactose. Mutants which retained the ability to grow on galactose are chromosomal mutants, while mutants which failed to grow on galactose carry plasmid borne mutations.

The plasmid borne mutants were further characterized by performing immunoblot analysis on whole cell extracts from the cells expressing these plasmids. This analysis revealed that 2 of the 7 plasmid mutants were expressing a truncated form of PAP. The other 5 mutants were not expressing any PAP protein. The 2 mutants which were expressing truncated PAP were examined by sequence analysis to determine the sites of the mutations. One mutant, NT185, had a point mutation at the C-terminus, changing Lys210 (AAG) to a stop codon (TAG), resulting in a deletion of approximately 3.5 kDa. The other mutant, NT187 had a change in the N-terminus, changing Try16 (TAC) to a stop codon (TAA) and then was able to restart at Met39, resulting in a 24.8 kDa protein.

B. Construction of *E. Coli* Expression Vector

To express the N-terminal deleted mature PAP in *E. coli* cells, NT187 plasmid DNA was digested with BstYI and HindIII restriction enzymes and the fragment around 830 bp was purified using the Gene Clean kit (Bio 101). The purified fragment was ligated to the *E. coli* expression vector, pQE31 (QIAGEN Inc.), which was digested with BamHI and HindIII and then treated with alkaline phosphatase. The resulting plasmid, NT190, contains the N-terminal deletion mutant PAP in the *E. coli* expression vector pQE31.

C. Expression of PAP Mutants in *E. Coli.*

NT190 was isolated from *E. coli* DH5α cells and transformed into the expression host, *E. coli* M15 (pREP4). M15 cells containing NT190 were cultured on 50 ml of LB medium containing 2% glucose, 100 μg/ml ampicillin, and 50 μg/ml kanamycin at 37° C. overnight with vigorous shaking. The following day, a large culture (500 ml of LB medium, containing 2% glucose, 100 μg/ml ampicillin, and 50 μg/ml kanamycin) was inoculated and grown at 37° C. with vigorous shaking until $A_{600}$ reached 0.9. IPTG was added to a final concentration of 2 mM, and the culture was incubated at 37° C. for 5 hours. Cells were harvested by centrifugation at 4,000×g for 10 min and stored at −70° C.

D. Purification of N-Terminal Deleted PAP

One gram of *E. coli* cells was thawed and resuspended in 5 ml of buffer A (6M guanidinium hydrochloride, 0.1M sodium phosphate, and 0.01 M Tris-HCl, pH 8.0) and stirred for 1 hr at room temperature. *E. coli* lysate was centrifuged at 10,000×g for 15 min at 4° C. and supernatant was collected. Two ml of a 50% slurry of Ni-agarose resin (QIAGEN Inc.), previously equilibrated in buffer A, were added. After stirring at room temperature for 45 min, the resin was carefully loaded into a poly-prep chromatography column (Bio-Rad). The column was washed with 20 column volumes of buffer A, and 10 column volumes of buffer B (8M urea, 0.1 M sodium phosphate, and 0.01 M Tris-HCl, pH 8.0). Proteins which did not bind the resin were washed with 20 column volumes of buffer C (8M urea, 0.1M sodium phosphate, and 0.01M Tri-HCl, pH 6.3). Finally, the bound protein was eluted with 50 ml of buffer C containing 250 mM imidazole and analyzed by SDS-PAGE and western blot analysis.

E. Antiviral Activity of N-Terminal Deleted PAP

To determine if N-terminal deleted PAP had anti-viral activity, wild-type tobacco plants were inoculated with 1 μg/ml PVX in the presence or absence of N-terminal deletion mutant purified from *E. coli*. PAP concentration was determined by ELISA and by SDS-PAGE. Fifteen ng/μl and 1.5 ng/μl mutant PAP were applied to tobacco leaves in the presence or absence of 1 μg/ml PVX. As shown in Table XI, tobacco plants inoculated with PVX in the presence of 1.5 or 15 ng/μl N-terminal deleted PAP showed fewer lesions on their inoculated leaves compared to plants inoculated with PVX in the absence of mutant PAP. Furthermore, as shown in Table XII, none of the plants inoculated with PVX in the presence of 15 ng/μl mutant PAP, and only 13% of plants inoculated with PVX in the presence of 1.5 ng/μl mutant PAP showed systemic PVX symptoms, while 100% of the plants inoculated with PVX in the presence of buffer alone showed systemic PVX symptoms. These results indicate that exogenously applied N-terminal deleted PAP protects tobacco against PVX infection and is thus anti-viral.

TABLE XI

Susceptibility of tobacco plants to PVX in the presence of exogenously applied N-terminal deleted PAP

| Protein applied[a] (ng/μl) | PVX (μg/ml) | Mean # of lesions[b] |
|---|---|---|
| none | 1 | 20 +/− 16 |
| PAP (1.5) | 1 | 2 +/− 2 |
| PAP (15) | 1 | 2 +/− 2 |

[a]Two leaves from each plant were inoculated with 50 μl of PVX (1 μg/ml) in the presence of 1.5 or 15 ng/μl N-terminal deleted PAP. Twelve plants were inoculated with PVX in the presence of buffer alone ("none") and 8 plants were inoculated with PVX in the presence of 50 μl of 1.5 or 15 ng/μl of mutant PAP.

[b]The number of lesions were counted at 7 days post-inoculation. Mean values +/− SD are shown.

TABLE XII

Percentage of plants showing systemic symptoms in the presence of exogenously applied N-terminally deleted PAP

| Protein applied[a] | PVX (μg/ml) | % plants showing systemic (ng/μl) symptoms[b] |
|---|---|---|
| none | 1 | 100 |
| PAP (1.5) | 1 | 13 |
| PAP (15) | 1 | 0 |

[a]Two leaves from each plant were inoculated with 50 μl of PVX (1 μg/ml) in the presence of 1.5 or 15 ng/μl N-terminal deleted PAP. Twelve plants were inoculated with PVX in the presence of buffer alone ("none") and 8 plants were inoculated with PVX in the presence of 50 μl of 1.5 or 15 ng/μl of mutant PAP.

[b]Systemic symptoms were scored 11 days post inoculation.

Applicant's patent application Ser. Nos. 08/500,611 and 500,694, filed Jul. 11, 1995 and PCT Application No. PCT/US96/11546, now U.S. Pat. Nos. 5,756,322 and 5,880,329 are herein incorporated by reference in their entireties.

All publications and patent applications mentioned in this specification are indicative of the level of skill of those skilled in the art to which this invention pertains. All these publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appending claims.

What is claimed is:

1. A pokeweed antiviral protein (PAP) mutant having reduced phytotoxicity compared to mature, wild-type PAP or PAP-v (Leu20Arg, Tyr49His), said PAP mutant containing intact catalytic active site amino acid residues (Glu176, Arg179) but differing from wild-type PAP substantially in that it is truncated at its N-terminus from 1 to about 38 amino acid residues, wherein the PAP mutant exhibits anti-viral or anti-fungal activity in plants.

2. The PAP mutant of claim 1, which is selected from the group of PAP mutants consisting of PAP (2-262), PAP (3-262), PAP (4-262), PAP (5-262), PAP (6-262), PAP (7-262), PAP (8-262), PAP (9-262), PAP (10-262), PAP (11-262), PAP (12-262), PAP (13-262), PAP (14-262), PAP (15-262), PAP (16-262), PAP (17-262), PAP (18-262), PAP (19-262), PAP (20-262), PAP (21-262), PAP (22-262), PAP (23-262), PAP (24-262), PAP (25-262), PAP (26-262), PAP (27-262), PAP (28-262), PAP (29-262), PAP (30-262), PAP (31-262), PAP (32-262), PAP (33-262), PAP (34-262), PAP (35-262), PAP (36-262), PAP (37-262), PAP (38-262) and PAP (39-262).

3. The PAP mutant of claim 1, further comprising the N-terminal signal sequence of wild-type PAP.

4. The PAP mutant of claim 1, further comprising the C-terminal extension of wild-type PAP.

5. A method of identifying a PAP mutant having reduced phytotoxicity, comprising:

(a) providing a eukaryotic cell stably transformed with a mutagenized PAP-encoding DNA molecule operably linked to an inducible promoter functional in eukaryotic cells, or with a non-mutagenized PAP-encoding DNA molecule followed by the step of mutagenizing the thus-transformed cell;

(b) culturing said transformed cell in suitable medium;

(c) adding an inducer to the medium to cause expression of the DNA molecule; and (d) determining whether said cultured cell survives the induction of expression of said PAP-encoding DNA molecule so that the biological activity of the PAP encoded by the mutagenized DNA molecule can then be determined.

6. The method of claim 5, wherein said providing comprises transforming a plurality of eukaryotic cells with randomly mutagenized PAP-encoding DNA molecules, and said step of determining comprises determining which transformed cells survive the induction of expression of said DNA molecules so that the biological activity of each of the PAPs encoded by the DNA molecule can then be determined.

7. The method of claim 5, further comprising assaying the PAP encoded by the DNA molecule to determine whether it retains PAP anti-fungal or anti-viral activity.

8. The method of claim 7, wherein said assaying comprises translating viral nucleic acid in an eukaryotic translation system in the presence of predetermined amounts of the PAP encoded by the DNA molecule.

9. The method of claim 8, wherein said translation system comprises a reticulocyte lysate system.

10. The method of claim 9, wherein said translation system comprises a rabbit reticulocyte lysate system.

11. The method of claim 5, wherein said eukaryotic cell is a yeast cell.

12. The method of claim 11, wherein said yeast is *Saccharomyces cerevisiae.*

13. An isolated and purified PAP mutant identified by the process of claim 5.

14. The PAP mutant of claim 1, which is PAP(2 262).

15. The PAP mutant of claim 1, which is PAP(3-262).

16. The PAP mutant of claim 1, which is PAP(4-262).

17. The PAP mutant of claim 1, which is PAP(5-262).

18. The PAP mutant of claim 1, which is PAP(6-262).

19. The PAP mutant of claim 1, which is PAP(7-262).

20. The PAP mutant of claim 1, which is PAP(8-262).

21. The PAP mutant of claim 1, which is PAP(9-262).

22. The PAP mutant of claim 1, which is PAP(10-262).

23. The PAP mutant of claim 1, which is PAP(11-262).

24. The PAP mutant of claim 1, which is PAP(12-262).

25. The PAP mutant of claim 1, which is PAP(13-262).

26. The PAP mutant of claim 1, which is PAP(14-262).

27. The PAP mutant of claim 1, which is PAP(15-262).

28. The PAP mutant of claim 1, which is PAP(16-262).

29. The PAP mutant of claim 1, which is PAP(17-262).

30. The PAP mutant of claim 1, which is PAP(18-262).

31. The PAP mutant of claim 1, which is PAP(19-262).

32. The PAP mutant of claim 1, which is PAP(20-262).

33. The PAP mutant of claim 1, which is PAP(21-262).

34. The PAP mutant of claim 1, which is PAP(22-262).

35. The PAP mutant of claim 1, which is PAP(23-262).

36. The PAP mutant of claim 1, which is PAP(24-262).

37. The PAP mutant of claim 1, which is PAP(25-262).

38. The PAP mutant of claim 1, which is PAP(26-262).

39. The PAP mutant of claim 1, which is PAP(27-262).

40. The PAP mutant of claim 1, which is PAP(28-262).

41. The PAP mutant of claim 1, which is PAP(29-262).

42. The PAP mutant of claim 1, which is PAP(30-262).

43. The PAP mutant of claim 1, which is PAP(31-262).

44. The PAP mutant of claim 1, which is PAP(32-262).

45. The PAP mutant of claim 1, which is PAP(33-262).

46. The PAP mutant of claim 1, which is PAP(34-262).

47. The PAP mutant of claim 1, which is PAP(35-262).

48. The PAP mutant of claim 1, which is PAP(36-262).

49. The PAP mutant of claim 1, which is PAP(37-262).

50. The PAP mutant of claim 1, which is PAP(38-262).

51. The PAP mutant of claim 1, which is PAP(39-262).

* * * * *

UNITED STATES PATENT AND TRADEMARK OFFICE

CERTIFICATE OF CORRECTION

PATENT NO. : 6,627,736 B1
APPLICATION NO. : 09/639456
DATED : September 30, 2003
INVENTOR(S) : Nilgun E. Tumer It is certified that error appears in the above-identified patent and that said Letters Patent is hereby corrected as shown below:

Delete the Specification, Columns 1 through 32 and replace with the new Specification, see attached.

Signed and Sealed this

Tenth Day of October, 2006

JON W. DUDAS
*Director of the United States Patent and Trademark Office*

(12) United States Patent
Tumer

(10) Patent No.: US 6,627,736 B1
(45) Date of Patent: Sep. 30, 2003

(54) PAP MUTANTS THAT EXHIBIT ANTI-VIRAL AND/OR ANTI-FUNGAL ACTIVITY IN PLANTS

(75) Inventor: Nilgun E. Tumer, Belle Mead, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 91 days.

(21) Appl. No.: 09/639,456

(22) Filed: Aug. 15, 2000

Related U.S. Application Data

(60) Division of application No. 09/005,273, filed on Jan. 9, 1998, now Pat. No. 6,137,030, which is a continuation of application No. PCT/US96/11546, filed on Jul. 11, 1996, which is a continuation-in-part of application No. 08/500,611, filed on Jul. 11, 1995, now Pat. No. 5,756,322, which is a continuation-in-part of application No. 08/500,694, filed on Jul. 11, 1995, now Pat. No. 5,880,329.

(51) Int. Cl.[7] .......................... A01H 5/00; C12N 15/82; C07K 1/00; C07K 14/00; A61K 35/78

(52) U.S. Cl. ....................... 530/370; 435/440; 435/468; 435/254.2

(58) Field of Search ................................ 530/370, 350; 435/4, 6, 7.2, 7.4, 7.6, 254.2, 254.21, 252.3, 440, 468

(56) References Cited

U.S. PATENT DOCUMENTS 5,304,730 A 4/1994 Lawson et al.

FOREIGN PATENT DOCUMENTS

FR 2699553 A1 6/1994

OTHER PUBLICATIONS

Dore et al, "Mutation dissociating the inhibitory activity of the pokeweek antiviral protein on eukaryote translation and *escherichia coli* growth", 1993, vol. 21 No. 18, pp. 4200–4205.*

Abel et al., Science 232:738–43 (1986).
Cuozzo et al., Bio/Technology 6:549–57 (1988).
Hemenway et al., EMBO J. 7:1273–80 (1988).
Stark et al., Bio/Technology 7:1257–62 (1989).
Lawson et al., Bio/Technology 8:127–34 (1990).
Kawchuk et al., Mol. Plant–Microbe Interactions 3(5):301–07 (1990).
Lodge et al., Proc. Natl. Acad. Sci. USA 90:7089–93 (1993).
Irvin et al., Pharmac. Ther. 55:279–302 (1992).
Endo et al., Biophys. Res. Comm., 150:1032–36 (1988).
Hartley et al., FEBS Lett. 290:65–68 (1991).
Beachy et al., Ann. Rev. Phytopathol. 28:451–74 (1990).
Golemboski et al., Proc. Natl. Acad. Sci. USA 87:6311–15 (1990).
Hayashi et al., J. Bioenerg. Biomem. 22:451–71 (1990).
Dore et al., Nuc. Acids Res. 21(18):4200–05 (1993).
Monzingo et al., J. Mol. Biol. 233:705–15 (1993).
Chen et al., Plant Pathol. 40:612–20 (1991).

* cited by examiner

*Primary Examiner*—Elizabeth F. McElwain
(74) *Attorney, Agent, or Firm*—Lerner, David, Littenberg, Krumholz & Mentlik, LLP

(57) ABSTRACT

Disclosed are PAP mutants having reduced phytotoxicity compared to wild-type PAP, and which confer broad spectrum resistance to viruses and/or fungi in plants. One group of PAP mutants is characterized by at least one amino acid substitution in the N-terminus of mature PAP, such as the Glycine 75 residue or the Glutamic acid 97 residue; two groups of additional PAP mutants are characterized by truncations in the N-terminal region of mature PAP and truncations or amino acid substitutions in the C-terminal region of mature PAP, respectively; and a further group are enzymatically inactive which still exhibit anti-fungal properties. Also disclosed are DNA molecules encoding the PAP mutants, mutant PAP DNA constructs, and transgenic seed and plants containing the DNAs. Further disclosed are methods for identifying PAP mutants having reduced phytotoxicity, as well as isolated and purified PAP mutants identified by the method.

51 Claims, No Drawings

PAP MUTANTS THAT EXHIBIT ANTI-VIRAL AND/OR ANTI-FUNGAL ACTIVITY IN PLANTS

CROSS-REFERENCE TO RELATED APPLICATIONS

This application is a divisional of U.S. application Ser. No. 09/005,273, filed Jan. 9, 1998, now U.S. Pat. No. 6,137,030, which is a continuation of PCT/US96/11546, filed Jul. 11, 1996, which is a continuation-in-part of U.S. application Ser. No. 08/500,611, filed Jul. 11, 1995, now U.S. Pat. No. 5,756,322, and application Ser. No. 08/500, 694, filed Jul. 11, 1995, now U.S. Pat. No. 5,880,329.

FIELD OF THE INVENTION

This invention relates generally to agricultural biotechnology, and more specifically to methods and genetic materials for conferring resistance to fungi and/or viruses in plants.

BACKGROUND OF THE INVENTION

The subject of plant protection against pathogens remains the area of utmost importance in agriculture. Many commercially valuable agricultural crops are prone to infection by plant viruses and fungi capable of inflicting significant damage to a crop in a given season, and drastically reducing its economic value. The reduction in economic value to the farmer in turn results in a higher cost of goods to ultimate purchasers. Several published studies have been directed to the expression of plant virus capsid proteins in a plant in an effort to confer resistance to viruses. See, e.g., Abel et al., Science 232:738–743 (1986); Cuozzo et al., Bio/Technology 6:549–557 (1988); Hemenway et al., EMBO J. 7:1273–1280 (1988); Stark et al., Bio/Technology 7:1257–1262 (1989); and Lawson et al., Bio/Technology 8:127–134 (1990). However, the transgenic plants exhibited resistance only to the homologous virus and related viruses, but not to unrelated viruses. Kawchuk et al., Mol. Plant-Microbe Interactions 3(5):301–307 (1990), disclose the expression of wild-type potato leaf roll virus (PLRV) coat protein gene in potato plants. Even though the infected plants exhibited resistance to PLRV, all of the transgenic plants that were inoculated with PLRV became infected with the virus and thus disadvantageously allowed for the continued transmission of the virus such that high levels of resistance could not be expected. See U.S. Pat. No. 5,304,730.

Lodge et al., Proc. Natl. Acad. Sci. USA 90:7089–7093 (1993), report the *Agrobacterium tumefaciens*-mediated transformation of tobacco with a cDNA encoding wild-type pokeweed antiviral protein (PAP) and the resistance of the transgenic tobacco plants to unrelated viruses. PAP, a Type I ribosome-inhibiting protein (RIP) found in the cell walls of *Phytolacca americana* (pokeweed), is a single polypeptide chain that catalytically removes a specific adenine residue from a highly conserved stem-loop structure in the 28S rRNA of eukaryotic ribosomes, and interferes with elongation factor-2 binding and blocking cellular protein synthesis. See, e.g., Irvin et al., Pharmac. Ther. 55:279–302 (1992); Endo et al., Biophys. Res. Comm., 150:1032–36 (1988); and Hartley et al., FEBS Lett. 290:65–68 (1991). The observations by Lodge were in sharp contrast to previous studies, supra, which reported that transgenic plants expressing a viral gene were resistant to that virus and closely related viruses only. See also Beachy et al., Ann. Rev. Phytopathol. 28:451–74 (1990); and Golemboski et al., Proc. Natl. Acad. Sci. USA 87:6311–15 (1990). Lodge also reports, however, that the PAP-expressing tobacco plants (i.e., above 10 ng/mg protein) tended to have a stunted, mottled phenotype, and that other transgenic tobacco plants that accumulated the highest levels of PAP were sterile. RIPs have proven unpredictable in other respects such as target specificity. Unlike PAP which (as demonstrated in Lodge), ricin isolated from castor bean seed is 1000 times more active on mammalian ribosomes than plant ribosomes. See, e.g., Harley et al., Proc. Natl. Acad. Sci. USA 79:5935–5938 (1982). Barley endosperm RIP also shows very little activity against plant ribosomes. See, e.g., Endo et al., Biochem. Biophys. Acta 994:224–226 (1988) and Taylor et al., Plant J. 5:827–835 (1984).

Fungal pathogens contribute significantly to the most severe pathogen outbreaks in plants. Plants have developed a natural defense system, including morphological modifications in their cell walls, and synthesis of various anti-pathogenic compounds. See, e.g., Boller et al., Plant Physiol 74:442–444 (1984); Bowles, Annu. Rev. Biochem. 59:873–907 (1990); Joosten et al., Plant Physiol. 89:945–951 (1989); Legrand et al., Proc. Natl. Acad. Sci. USA 84:6750–6754 (1987); and Roby et al., Plant Cell 2:999–1007 (1990). Several pathogenesis-related (PR) proteins have been shown to have anti-fungal properties and are induced following pathogen infection. These are different forms of hydrolytic enzymes, such as chitinases and β-1,3-glucanases that inhibit fungal growth in vitro by destroying fungal cell walls. See, e.g., Boller et al., supra; Grenier et al., Plant Physiol. 103:1277–123 (1993); Leah et al., J. Biol. Chem. 266:1464–1573 (1991); Mauch et al., Plant Physiol. 87:325–333 (1988); and Sela-Buurlage Buurlage et al., Plant Physiol. 101:857–863 (1993).

Several attempts have been made to enhance the pathogen resistance of plants via recombinant methodologies using genes encoding pathogenesis-related proteins (such as chitinases and β-1,3-glucanases) with distinct lytic activities against fungal cell walls. See, e.g., Broglie et al., Science 254:1194–1197 (1991); Vierheilig et al., Mol. Plant-Microbe Interact. 6:261–264 (1993); and Zhu et al., Bio/Technology 12:807–812 (1994). Recently, two other classes of genes have been shown to have potential in conferring disease resistance in plants. Wu et al., Plant Cell 7:1357–1368 (1995), report that transgenic potato expressing the *Aspergillus niger* glucose oxidase gene exhibited increased resistance to *Erwinia carotovora* and *Phytophthora infestans*. The hypothesis is that the glucose oxidase-catalyzed oxidation of glucose produces hydrogen peroxide, which when accumulates in plant tissues, leads to the accumulation of active oxygen species, which in turn, triggers production of various anti-pathogen and anti-fungal mechanisms such as phytoalexins (see Apostol et al., Plant Physiol. 90:109–116 (1989) and Degousee, Plant Physiol. 104:945–952 (1994)), pathogenesis-related proteins (Klessig et al., Plant Mol. Biol. 26:1439–1458 (1994)), strengthening of the plant cell wall (Brisson et al., Plant Cell 6:1703–1712 (1994)), induction of systemic acquired resistance by salicylic acid (Chen et al., Science 162:1883–1886 (1993)), and hypersensitive defense response (Levine et al., Cell 79:583–593 (1994)).

In addition to the studies on virus resistance in plants, RIPs have been studied in conjunction with fungal resistance. For example, Logeman et al., Bio/Technology 10:305–308 (1992), report that a RIP isolated from barley endosperm provided protection against fungal infection to transgenic tobacco plants. The combination of barley endosperm RIP and barley class-II chitinase has provided synergistic enhancement of resistance to *Rhizoctonia solani* in tobacco, both in vitro and in vivo. See, e.g., Lea et al., supra; Mauch et al., supra; Zhu et al., supra; and Jach et al., The Plant Journal 8:97–109 (1995). PAP, however, has not shown antifungal activity in vitro. See Chen et al., Plant Pathol. 40:612–620 (1991), which reports that PAP has no effect on the growth of the fungi *Phytophthora infestans, Colletotrichum coccodes, fusarium solani, fusarium sulphureum, Phoma foreata* and *Rhizoctonia solani* in vitro.

Hence, a need remains for a means by which to confer broad spectrum virus and/or fungus resistance to plants without causing cell death or sterility, and which requires a minimum number of transgenes.

BRIEF SUMMARY OF THE INVENTION

The present invention is directed to PAP mutants having reduced phytotoxicity, and which exhibit PAP biological activity in plants. By "PAP biological activity," it is meant PAP anti-viral activity and/or PAP anti-fungal activity. One preferred group of PAP mutants is characterized by at least one amino acid substitution in the N-terminus of mature PAP, such as a substitution for the Glycine 75 residue or the Glutamic acid 97 residue. Another group of PAP mutants is characterized by a truncation of as many as 38 amino acids at the N-terminus of mature PAP. Yet another preferred group of PAP mutants is characterized by mutations such as truncations in the C-terminal region of mature PAP. More preferred are PAP mutants truncated at their C-terminus by at least about 26 to about 76 mature PAP amino acids (not counting the 29-amino acid C-terminal extension of wild-type PAP). A further group of PAP mutants are enzymatically inactive and do not exhibit PAP anti-viral activity in vitro or in planta; yet, they exhibit PAP anti-fungal activity in plants. The PAP mutants of the present invention may also include the 22-amino acid N-terminal signal sequence and/or the C-terminal extension of wild-type PAP.

The present invention also provides DNA molecules encoding the PAP mutants, which may or may not also encode the 22-amino acid N-terminal signal sequence of mature PAP and/or the 29-amino acid C-terminal extension of wild-type PAP. The DNAs can be operably linked to a promoter functional in procaryotic cells (e.g., *E. coli*), or eukaryotic cells such as plants, and then stably transformed into a vector functional in said cells. Hosts, e.g., procaryotic or eukaryotic cells (e.g., yeast or plants), stably transformed with a mutant PAP-encoding DNA are also provided, as well as protoplasts stably transformed with the DNAs. Transgenic plants and seed containing the DNAs are also provided. Expression of the DNAs in the transgenic plants confers broad spectrum virus and/or fungus resistance upon the plants without being as phytotoxic to the plant as wild-type PAP. Plants included within the scope of the present invention are monocots, such as cereal crops, and dicot plants.

The present invention further provides a method for identifying a PAP mutant having reduced phytotoxicity and which exhibits PAP biological activity in plants. The method involves the steps of providing a transformed eukaryotic cell such as yeast containing a mature PAP-encoding DNA molecule operably linked to an inducible promoter functional in the eukaryotic cell. The PAP-encoding DNA is mutagenized prior to transformation, or the transformed cell is mutagenized (i.e., the mutagenesis is performed after the cell is transformed with the PAP construct). The thus-transformed cells are cultured in a suitable medium, and after a predetermined time, an inducer is added to the medium to cause expression of the DNA molecule. A determination is then made as to whether the survival of cultured cells is due to the expression of a mutant PAP. Such mutant PAPs which exhibit a substantial lack of toxicity to the host would be considered as PAP mutants which exhibit reduced phytotoxicity. The thus-identified PAP mutants which also exhibit broad spectrum virus and/or fungus resistance, as determined by in vitro (e.g., by exogenous application of the virus or fungus), or in vivo (e.g., by expression in transgenic plants); would also be considered as PAP mutants which retain PAP biological activity in plants. The present invention further provides isolated and purified PAP mutants identified by the aforesaid method.

DETAILED DESCRIPTION OF THE INVENTION

Transgenic plants expressing DNAs encoding the PAP mutants of the present invention exhibit reduced phytotoxicity compared to transgenic plants that produce mature, wild-type PAP, ("PAP"), or variant PAP, i.e. PAP-v, but also exhibit anti-viral and/or anti-fungal activities. By the term "reduced phytotoxicity," it is meant that a transgenic plant which expresses a mutant PAP-encoding DNA exhibits a normal and fertile phenotype and does not exhibit the stunted, mottled phenotype characteristic of transgenic plants that produce mature PAP (as disclosed in Lodge for example). By "wild-type PAP," it is meant the PAP amino acid sequence 1-262, the 22-amino acid N-terminal signal peptide ("the N-terminal signal sequence of wild-type PAP"), and the 29 amino acid C-terminal extension (amino acids enumerated 263-291), all illustrated in Table I below as SEQ ID NO:2. The corresponding nucleotide sequence is set forth as SEQ ID NO:1. Thus, by the terms "wild-type, mature PAP," or "mature PAP", it is meant the PAP amino acid sequence 1-262 shown in Table I.

TABLE I

```
5'CTATGAAGTCGGGTCAAAGCATATACAGGCTATGCATTGTTAGAAACATTGATGCCTCTGATCCC
GATAAACAATACAAATTAGACAATAAGATGACATACAAGTACCTAAACTGTGTATGGGGAGTGA
AACCTCAGCTGCTAAAAAAACGTTGTAAGAAAAAAAGAAAGTTGTGAGTTAACTACAGGGCGAAA
GTATTGGAACT
                        A
AGCTAGTAGGAAGGGAAG ATG AAG TCG ATG CTT GTG GTG ACA ATA TCA ATA
                   Met Lys Ser Met Leu Val Val Thr Ile Ser Ile
                                        (67)
TGG CTC ATT CTT GCA CCA ACT TCA ACT TGG GCT GTG AAT ACA ATC ATC TAC
Trp Leu Ile Leu Ala Pro Thr Ser Thr Trp Ala Val Asn Thr Ile Ile Tyr
                                         (1)
                   (100)                           G
AAT GTT GGA AGT ACC ACC ATT AGC AAA TAC GCC ACT TTT CTG AAT GAT CTT
Asn Val Gly Ser Thr Thr Ile Ser Lys Tyr Ala Thr Phe Leu Asn Asp Leu
             (10)                                (20)
CGT AAT GAA GCG AAA GAT CCA AGT TTA AAA TGC TAT GGA ATA CCA ATG CTG
```

TABLE I-continued

```
Arg Asn Glu Ala Lys Asp Pro Ser Leu Lys Cys Tyr Gly Ile Pro Met Leu
                     (30)                                 (40)
                            C
CCC AAT ACA AAT ACA AAT CCA AAG TAC GTG TTG GTT GAG CTC CAA GGT TCA
Pro Asn Thr Asn Thr Asn Pro Lys Tyr Val Leu Val Glu Leu Gln Gly Ser
                               (50)
AAT AAA AAA ACC ATC ACA CTA ATG CTG AGA CGA AAC AAT TTG TAT GTG ATG
Asn Lys Lys Thr Ile Thr Leu Met Leu Arg Arg Asn Asn Leu Tyr Val Met
        (60)                                   (70)
GGT TAT TCT GAT CCC TTT GAA ACC AAT AAA TGT CGT TAC CAT ATC TTT AAT
Gly Tyr Ser Asp Pro Phe Glu Thr Asn Lys Cys Arg Tyr His Ile Phe Asn
                  (80)                                (90)
GAT ATC TCA GGT ACT GAA CGC CAA GAT GTA GAG ACT ACT CTT TGC CCA AAT
Asp Ile Ser Gly Thr Glu Arg Gln Asp Val Glu Thr Thr Leu Cys Pro Asn
                            (100)
GCC AAT TCT CGT GTT AGT AAA AAC ATA AAC TTT GAT AGT CGA TAT CCA ACA
Ala Asn Ser Arg Val Ser Lys Asn Ile Asn Phe Asp Ser Arg Tyr Pro Thr
    (110)                                   (120)
TTG GAA TCA AAA GCG GGA GTA AAA TCA AGA AGT CAG GTC CAA CTG GGA ATT
Leu Glu Ser Lys Ala Gly Val Lys Ser Arg Ser Gln Val Gln Leu Gly Ile
               (130)                                 (140)
CAA ATA CTC GAC AGT AAT ATT GGA AAG ATT TCT GGA GTG ATG TCA TTC ACT
Gln Ile Leu Asp Ser Asn Ile Gly Lys Ile Ser Gly Val Met Ser Phe Thr
                         (150)
GAG AAA ACC GAA GCC GAA TTC CTA TTG GTA GCC ATA CAA ATG GTA TCA GAG
Glu Lys Thr Glu Ala Glu Phe Leu Leu Val Ala Ile Gln Met Val Ser Glu
(160)                               (170)
GCA GCA AGA TTC AAG TAC ATA GAG AAT CAG GTG AAA ACT AAT TTT AAC AGA
Ala Ala Arg Phe Lys Tyr Ile Glu Asn Gln Val Lys Thr Asn Phe Asn Arg
           (180)                               (190)
GCA TTC AAC CCT AAT CCC AAA GTA CTT AAT TTG CAA GAG ACA TGG GGT AAG
Ala Phe Asn Pro Asn Pro Lys Val Leu Asn Leu Gln Glu Thr Trp Gly Lys
                      (200)                            (210)
ATT TCA ACA GCA ATT CAT GAT GCC AAG AAT GGA GTT TTA CCC AAA CCT CTC
Ile Ser Thr Ala Ile His Asp Ala Lys Asn Gly Val Leu Pro Lys Pro Leu
                                (220)
GAG CTA GTG GAT GCC AGT GGT GCC AAG TGG ATA GTG TTG AGA GTG GAT GAA
Glu Leu Val Asp Ala Ser Gly Ala Lys Trp Ile Val Leu Arg Val Asp Glu
       (230)                                   (240)
ATC AAG CCT GAT GTA GCA CTC TTA AAC TAC GTT GGT GGG AGC TGT CAG ACA
Ile Lys Pro Asp Val Ala Leu Leu Asn Tyr Val Gly Gly Ser Cys Gln Thr
                   (250)                                (260)
ACT TAT AAC CAA AAT GCC ATG TTT CCT CAA CTT ATA ATG TCT ACT TAT TAT
Thr Tyr Asn Gln Asn Ala Met Phe Pro Gln Leu Ile Met Ser Thr Tyr Tyr
(262)                       (270)
AAT TAC ATG GTT AAT CTT GGT GAT CTA TTT GAA GGA TTC TGATCATAAACA
Asn Tyr Met Val Asn Leu Gly Asp Leu Phe Glu Gly Phe
   (280)                                    (290)
TAATAAGGAGTATATATATATTACTCCAACTATATTATAAAGCTTAAATAAGAGGCCGTGTTAATT
AGTACTTGTTGCTTTTGCTTTATGGTGTTGTTTATTATGCCTTGTATGCTTGTAATATTATCTAGAG
AACAAGATGTACTGTGTAATAGTCTTGTTTGAAATAAAACTTCCAATTATGATGCAAAAAAAAAA
AAAAA3'
```

Table I further shows PAP-v amino acids and corresponding nucleotides in proper alignment with wild-type PAP. Basically, the amino acid sequence of PAP-v differs from that of wild-type PAP in terms of a Leu20Arg (i.e., an arginine residue at position 20 of mature PAP as opposed to a leucine residue) and a Tyr49His substitution. The third change in the PAP-v nucleotide sequence (TCG→TCA codon for the first occurring Ser in the signal sequence) has no effect on the amino acid sequence. Table I also shows 5' and 3' non-coding, flanking sequences. Upon expression in eukaryotic cells, the N-terminal 22-amino acid sequence of wild-type PAP is co-translationally cleaved, yielding a polypeptide having a molecular weight of about 32 kD, which is then further processed by the cleavage of the C-terminal 29-amino acids ("the C-terminal extension of wild-type PAP" or "PAP (263-292)"), yielding mature, wild-type PAP (hereinafter "PAP (1-262)") (i.e., that which is isolated from *Phytolacca americana* leaves), having a molecular weight of about 29 kD. See Irvin et al., Pharmac. Ther. 55:279–302 (1992); Dore et al., Nuc. Acids Res. 21(18):4200–4205 (1993); Monzingo et al., J. Mol. Biol. 233:705–15 (1993); Turner et al., Proc. Natl. Acad. Sci. USA 92:8448–8452 (1995).

By the phrase "PAP anti-viral activity," it is meant that the expression of a mutant PAP of the present invention in a transgenic plant confers broad spectrum virus resistance, i.e., resistance to or the capability of suppressing infection by a number of unrelated viruses, including but not limited to RNA viruses e.g., potexviruses such as (PVX, potato virus X), potyvirus (PVY), cucumber mosaic virus (CMV), tobacco mosaic viruses (TMV), barley yellow dwarf virus (BYDV), wheat streak mosaic virus, potato leaf roll virus (PLRV), plumpox virus, watermelon mosaic virus, zucchini yellow mosaic virus, papaya ringspot virus, beet western yellow virus, soybean dwarf virus, carrot read leaf virus and DNA plant viruses such as tomato yellow leaf curl virus. See also Lodge, Tomlinson et al., J. Gen. Virol. 22:225–232 (1974); and Chen et al., Plant Pathol. 40:612–620 (1991).

By the phrase "PAP anti-fungal activity", it is meant that the mutant PAPs of the present invention confer broad spectrum fungal resistance to plants. The mutant PAPs of the present invention provide increased resistance to diseases caused by plant fungi, including those caused by Pythium (one of the causes of seed rot, seedling damping off and root rot), Phytophthora (the cause of late blight of potato and of root rots, and blights of many other plants), Bremia, Peronospora, Plasmopara, Pseudoperonospora and Sclerospora (causing downy mildews), *Erysiphe graminis* (causing powdery mildew of cereals and grasses), Verticillium (causing vascular wilts of vegetables, flowers, crop plants and trees), Rhizoctonia (causing damping off disease of many plants and brown patch disease of turfgrasses), Fusarium (causing root rot of bean, dry rot of potatoes), Cochliobolus (causing root and foot rot, and also blight of cereals and grasses), Giberella (causing seedling blight and foot or stalk rot of corn and small grains), Gaeumannomyces (causing the take-all and whiteheads disease of cereals), Schlerotinia (causing crown rots and blights of flowers and vegetables and dollar spot disease of turfgrasses), Puccinia (causing the stem rust of wheat and other small grains), Ustilago (causing corn smut), Magnaporthae (causing summer patch of turfgrasses), and Schlerotium (causing southern blight of turfgrasses). Other important fungal diseases include those caused by Cercospora, Septoria, Mycosphoerella, Glomerella, Colletotrichum, Helminthosporium, Alterneria, Botrytis, Cladosporium, and Aspergillus.

Applicant also believes that the mutant PAPs of the present invention confer increased resistance to insects, bacteria and nematodes in plants. Important bacterial diseases include those caused by Pseudomonas, Xanthomonas, Erwinia, Clavibacter and Streptomyces.

The PAP mutants of the present invention differ from wild-type PAP substantially as follows: (1) those which exhibit altered compartmentalization in vivo; (2) C-terminal mutants, including but not limited to deletion or frameshift mutants; (3) N-terminal mutants; and (4) active-site mutants. The first category of PAP mutants may have altered compartmentalization properties in vivo; that is, they may not be localized in the same subcellular compartment as wild-type PAP. While not intending to be bound to any particular theory of operation, Applicant believes that these PAP mutants are unable to undergo co-translational processing (to remove the 22 amino acid signal peptide) and/or post-translational processing (to remove the 29-amino acid C-terminal fragment) in yeast, which results in substantially diminished or negligible cytotoxicity. These mutants are also non-phytotoxic. What is particularly surprising or unexpected about the function of these mutant PAPs in vivo is that the mutations are located within the sequence encoding the mature PAP (1-262), and not within the N-terminal signal peptide or the 29-amino acid C-terminal extension. In addition, the mutant PAPs are enzymatically active in inhibiting translation in vitro, indicating that phytotoxicity is not solely a function of enzymatic activity. Preferred PAP mutants include a conservative point mutation such that wild-type PAP amino acid residue 75 glycine (Gly75) is changed to valine, alanine, isoleucine or leucine, or (2) a conservative or non-conservative point mutation at wild-type PAP amino acid residue 97 Glutamic acid (Glu97). More preferred PAP mutants are PAP (1-262, Gly75Val) and PAP (1-262, Glu97Lys), the respective DNAs of which can be prepared simply by changing the wild-type GGT codon for glycine75 to GTT (valine), and the GAA codon for glutamic acid 97 to AAA (lysine). Other PAP mutants having altered compartmentalization properties can be identified by the selection method described below. Dore et al., supra, disclose an Arg67Gly PAP mutant (numbered in Dore as Arg 68Gly due to the presence of an N-terminal methionine residue), but which is toxic to eukaryotic cells and non-toxic to procaryotic cells such as *E. coli*. This mutant is not included within the scope of the present invention.

The second category of PAP mutants of the present invention have deletions or amino acid substitutions in the C-terminal region of PAP. Applicant has unexpectedly discovered that these mutants are also non-toxic in vivo (i.e., non-phytotoxic) even though they inhibit translation in vitro. Preferred mutants have deletions of from about 26 to about 76 amino acids of mature PAP, and more preferred are the PAP mutants PAP (1-236)-PAP (1-184), inclusive. Thus, truncations beginning at about amino acid residue 237 of wild-type mature PAP, e.g., PAP (1-236), PAP (1-235), PAP (1-234), PAP (1-233), PAP (1-232), PAP (1-231), PAP (1-230), PAP (1-229), PAP (1-228), PAP (1-227), PAP (1-226), PAP (1-225), PAP (1-224), PAP (1-223), PAP (1-222), PAP (1-221), PAP (1-220), PAP (1-219), PAP (1-218), PAP (1-217), PAP (1-216), PAP (1-215), PAP (1-214), PAP (1-213), PAP (1-212), PAP (1-211), PAP (1-210), PAP (1-209), PAP (1-208), PAP (1-207), PAP (1-206), PAP (1-205), PAP (1-204), PAP (1-203), PAP (1-202), PAP (1-201), PAP (1-200), PAP (1-199), PAP (1-198), PAP (1-197), PAP (1-196), PAP (1-195), PAP (1-194), PAP (1-193), PAP (1-192), PAP (1-191), PAP (1-190), PAP (1-189), PAP (1-188), PAP (1-187), PAP (1-186), PAP (1-185), and PAP (1-184) are encompassed by the present invention. More preferred mutants include PAP (1-184Glu), PAP (1-188Lys), PAP (1-206Glu), PAP (1-209) and PAP (1-236Lys). Deletions shorter than about 26 (i.e., between 1 and 25 amino acids, inclusive) or longer than 76 mature PAP amino acids are included in the scope of the present invention provided that they are non-toxic to plant cells, which can be determined by the selection method described in detail below, and they confer fungus and/or virus resistance in planta. The latter properties can be determined in vitro, e.g., by inoculating plant parts, e.g. leaves, with the PAP mutant in the presence of a virus or fungus, or by separate in vivo assays wherein a transgenic plant transformed with a mutant PAP-encoding DNA is inoculated with a fungus or virus. A preferred C-terminal substitution mutant is PAP (1-262, Leu202Phe). Again, while not intending to be bound by any particular theory of operation, Applicant believes that the sequence of PAP amino acids 244Glu-259Cys (shown in Table I), which is homologous to the consensus sequence for the prokaryotic membrane lipoprotein lipid attachment site (Hayashi et al., J. Bioenerg. Biomem. 22:451–471 (1990)), and which is absent from each of the PAP mutants disclosed above, is involved in binding of PAP to phospholipids on endoplasmic reticulum (ER) membranes which facilitates the translocation of PAP into the cytosol of the cell where it inhibits protein synthesis. Disarming this function, e.g., by deletion or by frameshift mutation, results in PAP mutants having the instantly disclosed properties.

Dore also discloses the PAP mutant Phe195Tyr, Lys211Arg (which numbering is +1 out-of-phase with the numbering used herein due to the N-terminal Met residue required for expression in *E. coli*), which is toxic to eukaryotic cells (such as plants) but non-toxic to procaryotes such as *E. coli*. Accordingly, this PAP mutant disclosed in the Dore publication is not included within the scope of the present invention.

The third category of PAP mutants is characterized by truncations of from 1 to at least about 38 N-terminal amino acid residues of mature PAP. These mutants include PAP (2-262), PAP (3-262), PAP (4-262), PAP (5-262), PAP (6-262), PAP (7-262), PAP (8-262), PAP (9-262), PAP (10-262), PAP (11-262), PAP (12-262), PAP (13-262), PAP (14-262), PAP (15-262), PAP (16-262), PAP (17-262), PAP (18-262), PAP (19-262), PAP (20-262), PAP (21-262), PAP (22-262), PAP (23-262), PAP (24-262), PAP (25-262), PAP (26-262), PAP (27-262), PAP (28-262), PAP (29-262), PAP (30-262), PAP (31-262), PAP (32-262), PAP (33-262), PAP (34-262), PAP (35-262), PAP (36-262), PAP (37-262), PAP (38-262) and PAP (39-262). Truncations of greater than 38 N-terminal amino acid residues of mature PAP are included within the scope of the present invention to the extent that they exhibit PAP biological activity and reduced phytotoxicity in vivo. These properties may be determined in accordance with the procedures set forth in the working examples, below.

The fourth category of PAP mutants contain active-site mutations which render the PAP molecule enzymatically inactive (as measured by their lack of ability to inhibit translation in vitro and/or in eukaryotic ribosomes). Applicant has surprisingly and unexpectedly found that these mutants exhibit broad spectrum anti-fungal activity when expressed in plants, even though they exhibit negligible PAP anti-viral activity. The putative active site of PAP includes amino acid residues Tyr72, Tyr123, Glu176, Arg179 and Trp208. Accordingly, PAP active site mutants, e.g., which contain a conservative or even non-conservative substitution in the PAP active site or wherein at least one active site amino acid is deleted or replaced by another amino acid, wherein the PAP is rendered enzymatically inactive but retains anti-fungal activity, are encompassed within the present invention. PAP mutants can be tested for enzymatic and anti-fungal activities using the assay procedures described in the working examples, below. A preferred PAP active site mutant is PAP (1-262, Glu176Val).

In regard to the disclosed PAP mutants, the phrase "which differs from wild-type PAP substantially in that . . . " means that except for the amino acid changes (described above), that are necessary to confer reduced phytotoxicity and anti-viral and/or anti-fungal activity, the amino acid sequences of the mutant PAPs are substantially identical to that of mature PAP. By the term "substantially identical," it is meant that the PAP mutants of the present invention can be further modified by way of additional substitutions, additions or deletions provided that the resultant PAP mutant retains reduced phytotoxicity and PAP biological activity as defined herein. For example, the N-terminus of the mutant PAP may be changed to a methionine residue, either by substitution or addition, to allow for expression of a DNA encoding the mutant PAP in various host cells particularly *E. coli*. The PAP mutants of the present invention may further include the N-terminal 22-amino acid signal peptide of wild-type PAP and/or the 29-amino acid C-terminal extension, both of which are shown in Table I above.

DNAs encoding the mutant PAPs of the present invention can be prepared by manipulation of known PAP genes. See Ausubel et al. (eds.), Vol. 1, Chap. 8 in *Current Protocols in Molecular Biology*, Wiley, N.Y. (1990). The DNAs may also be prepared via PCR techniques. See *PCR Protocols*, Innis et al. (eds.), Academic Press, San Diego, Calif. (1990). The mutant PAP-encoding DNA (e.g., a cDNA) is preferably inserted into a plant transformation vector in the form of an expression cassette containing all of the necessary elements for transformation of plant cells. The expression cassette typically contains, in proper reading frame, a promoter functional in plant cells, a 5' non-translated leader sequence, the mutant PAP DNA, and a 3' non-translated region functional in plants to cause the addition of polyadenylated nucleotides to the 3' end of the RNA sequence. Promoters functional in plant cells may be obtained from a variety of sources such as plants or plant DNA viruses. The selection of a promoter used in expression cassettes will determine the spatial and temporal expression pattern of the construction in the transgenic plant. Selected promoters may have constitutive activity and these include the CaMV 35S promoter, the actin promoter (McElroy et al., Plant Cell 2:163–171 (1990); McElroy et al., Mol. Gen. Genet. 231:150–160 (1991); Chibbar et al., Plant Cell Rep. 12:506–509 (1993), and the ubiquitin promoter (Binet et al., Plant Science 79:87–94 (1991), Christensen et al., Plant Mol. Biol. 12:619–632 (1989); Taylor et al., Plant Cell Rep. 12:491495 (1993)). Alternatively, they may be wound-induced (Xu et al., Plant Mol. Biol 22:573–588 (1993), Logemann et al., Plant Cell 1:151–158 (1989), Rohrmeier and Lehle, Plant Mol. Bio. 22:783–792 (1993), Firek et al., Plant Mol. Biol. 22:129–142 (1993), Warener et al., Plant J. 3:191–201 (1993)) and thus drive the expression of the mutant PAP gene at the sites of wounding or pathogen infection. Other useful promoters are expressed in specific cell types (such as leaf epidermal cells, meosphyll cells, root cortex cells) or in specific tissues or organs (roots, leaves or flowers, for example). Patent Application WO 93/07278, for example, describes the isolation of the maize trpA gene which is preferentially expressed in pith cells. Hudspeth and Grula, Plant Mol. Biol. 12:579–589 (1989), have described a promoter derived from the maize gene encoding phosphoenolpyruvate carboxylase (PEPC) with directs expression in a leaf-specific manner. Alternatively, the selected promoter may drive expression of the gene under a light-induced or other temporally-regulated promoter. A further alternative is that the selected promoter be chemically regulated. The DNAs may also encode the N-terminal signal sequence and/or the C-terminal extension of wild-type PAP.

A variety of transcriptional cleavage and polyadenylation sites are available for use in expression cassettes. These are responsible for correct processing (formation) of the 3' end of mRNAs. Appropriate transcriptional cleavage and polyadenylation sites which are known to function in plants include the CaMV 35S cleavage and polyadenylation sites, the tml cleavage and polyadenylations sites, the nopaline synthase cleavage and polyadenylation sites, the pea rbcS E9 cleavage and polyadenylation sites. These can be used in both monocotyledons and dicotyledons.

Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous cells. For example, the introns of the maize Adhl gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop 1:1183–1200 (1987)). In the same experimental system, the intron from the maize bronze-l gene had a similar effect in enhancing expression (Callis et al., supra.). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic mottle Virus (MCMV), and Alfalfa Mosaic Virus (AMV) have been shown to be effective in enhancing expression (e.g. Gallie et al., Nucl. Acids Res. 15:8693–8711 (1987); Skuzeski et al., Plant Mol. Biol. 15:65–79 (1990)).

Numerous transformation vectors are available for plant transformation, and the genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformations include the nptII gene which confers resistance to kanamycin (Messing and Vierra, Gene 19:259–268 (1982); Bevan et al., Nature 304:184–187 (1983)), the bar gene which confers resistance to the herbicide phosphinothricin (White et al., Nucl. Acids Res. 18:1062 (1990); Spencer et al., Theor. Appl. Genet. 79:625–631 (1990)), the hph gene which confers resistance to the antibiotic hygromycin (Blochinger & Diggelmann, Mol. Cell Biol. 4:2929–2931 (1984)), and the dhfr gene, which confers resistance to methotrexate. Vectors suitable for Agrobacterium transformation typically carry at least one T-DNA border sequence. These include vectors such as pBIN19 (Bevan, Nucl. Acids Res. (1984) and pCIB200 (EP 0 332 104).

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on Agrobacterium include transformation via particle bombardment, protoplast uptake (e.g. PEG and electroporation) and microinjection. The choice of vector depends largely on the preferred selection for the species being transformed. For example, pCIB3064 is a pUC-derived vector suitable for the direct gene transfer technique in combination with selection by the herbicide basta (or phosphinothricin). It is described in WO 93/07278 and Koziel et al. (Biotechnology 11:194–200 (1993)).

An expression cassette containing the mutant PAP gene DNA containing the various elements described above may be inserted into a plant transformation vector by standard recombinant DNA methods. Alternatively, some or all of the elements of the expression cassette may be present in the vector, and any remaining elements may be added to the vector as necessary.

Transformation techniques for dicotyledons are well known in the art and include Agrobacterium-based techniques and techniques which do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described in Paszkowski et al., EMBO J 3:2717–2722 (1984), Potrykis et al., Mol. Gen. Genet. 199:169–177 (1985), Reich et al., Biotechnology 4:1001–1004 (1986), and Klein et al., Nature 327:70–73 (1987). In each case the transformed cells are regenerated to whole plants using standard techniques.

Agrobacterium-mediated transformation is a preferred technique for transformation of dicotyledons because of its high efficiency of transformation and its broad utility with many different species. The many crop species which are routinely transformable by Agrobacterium include tobacco, tomato, sunflower, cotton, oilseed rape, potato, soybean, alfalfa and poplar (EP 0 317 511 (cotton), EP 0 249 432 (tomato), WO 87/07299 (Brassica), U.S. Pat. No. 4,795,855 (poplar)). Agrobacterium transformation typically involves the transfer of the binary vector carrying the foreign DNA of interest (e.g. pCIB200 or pCIB2001) to an appropriate Agrobacterium strain which may depend on the complement of vir genes carried by the host Agrobacterium strain either on a co-resident plasmid or chromosomally (e.g. strain CIB542 for pCIB200 (Uknes et al. Plant Cell 5:159–169 (1993)). The transfer of the recombinant binary vector, to Agrobacterium is accomplished by a triparental mating procedure using *E. coli* carrying the recombinant binary vector, a helper *E. coli* strain which carries a plasmid such as pRK2013 which is able to mobilize the recombinant binary vector to the target Agrobacterium strain. Alternatively, the recombinant binary vector can be transferred to Agrobacterium by DNA transformation (Hofgen & Willmitzer, Nucl. Acids Res. 16:9877 (1988)).

Transformation of the target plant species by recombinant Agrobacterium usually involves co-cultivation of the Agrobacterium with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantages of avoiding complex vector construction and generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093–1096 (1986)).

Published European Patent Applications EP 0 292 435 and EP 0 392 225, and PCT application WO 93/07278 describe techniques for the preparation of callus and protoplasts of maize, transformation of protoplasts using PEG or electroporation, and the regeneration of maize plants from transformed protoplasts. Gordeon-Kamm et al., Plant Cell 2:603–618 (1990), and Fromm et al., Biotechnology 11:194–200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for Japonica-types and Indica-types (Zhange et al., Plant Cell Rep. 7:739–384 (1988); Shimamoto et al., Nature 338:274–277 (1989); Datta et al., Biotechnology 8:736–740 (1990)). Both types are also routinely transformable using particle bombardment (Christou et al., Biotechnology 9:957–962 (1991)).

Patent Application EP 0 332 581 described techniques for the generation, transformation and regeneration of Pooideae protoplasts. Furthermore wheat transformation has been described by Vasil et al. (Biotechnology 10:667–674 (1992)) using particle bombardment into cells of type C long-term regenerable callus, and also by Vasil et al. (Biotechnology 11:1553–1558 (1993)) and Weeks et al. (Plant Physiol.

102:1077–1084 (1993)) using particle bombardment of immature embryos and immature embryo-derived callus.

Transformation of monocot cells such as *Zea mays* can be achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. No. 5,240,855 (particle gun); U.S. Pat. No. 5,204,253 (cold gas shock accelerated microprojectiles); U.S. Pat. No. 5,179,022 (biolistic apparatus); U.S. Pat. Nos. 4,743,548 and 5,114,854 (microinjection); and U.S. Pat. Nos. 5,149,655 5,120,657 (accelerated particle mediated transformation); U.S. Pat. No. 5,066,587 (gas driven microprojectile accelerator); U.S. Pat. No. 5,015,580 (particle-mediated transformation of soy bean plants); U.S. Pat. No. 5,013,660 (laser beam-mediated transformation); and U.S. Pat. Nos. 4,849,355 and 4,663,292.

The thus-transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See, e.g., Newell et al., Plant Cell Rep. 10:30–34 (1991) (disclosing potato transformation by stem culture).

The mutant PAP encoding DNAs of the present invention confer broad spectrum fungus and virus resistance to any plant capable of expressing the DNAs, including monocots (e.g., cereal crops) and dicots. Specific examples include maize, tomato, turfgrass, asparagus, papaya, sunflower, rye, beans, ginger, lotus, bamboo, potato, rice, peanut, barley, malt, wheat, alfalfa, soybean, oat, eggplant, squash, onion, broccoli, sugarcane, sugar beet, beets, apples, oranges, grapefruit, pear, plum, peach, pineapple, grape, rose, carnation, daisy, tulip, Douglas fir, cedar, white pine, scotch pine, spruce, peas, cotton, flax and coffee.

PAP mutants other than those specifically described above can be identified by a selection system in eukaryotic cells. In a preferred embodiment, a PAP-encoding DNA molecule, operably linked to an inducible promoter functional in the eukaryotic cell, is randomly mutagenized in accordance with standard techniques. The cell is then transformed with the mutagenized PAP construct. The thus-transformed cell is then cultured in a suitable medium for a predetermined amount of time, e.g., sufficient to cause some growth of the cells, at which time an inducer is added to the medium to cause expression of the mutagenized DNA molecule. If the cultured cell survives the induction of the expression of the mutagenized PAP DNA molecule, which indicates that the mutagenesis resulted in the expression of a non-toxic PAP mutant, the PAP mutant can be then assayed in vitro or in vivo to determine whether it retains PAP biological activity. Preferred in vitro assays include eukaryotic translation systems such as reticulocyte lysate systems wherein the extent of the inhibition of protein synthesis in the system caused by the PAP mutant is determined. Preferred host cells are yeast cells such as *Saccharomyces cerevisiae*, as described in greater detail in Example 1, below. This method can also be conducted with a plurality of randomly mutagenized PAP-encoding DNA molecules. The PAP mutants identified as having reduced phytotoxicity and which retain PAP anti-viral and/or anti-fungal activity, as determined by subsequent assays, can then be isolated, purified and sequenced in accordance with standard techniques.

In another embodiment, the mutagenesis is performed after the transformation of the eukaryotic cell. The disadvantage with mutagenizing the DNA after transformation is that the chromosomal DNA of the host can also be mutagenized. To determine whether the mutations of the surviving cells are chromosomal or plasmid-borne in nature, this embodiment requires the step of replacing the transforming PAP-encoding DNA with wild-type PAP-encoding DNA under the control of an inducible promoter, and growing the cells in the presence of the inducer. Mutants which retain the ability to grow are chromosomal mutants, whereas mutants which fail to grow are plasmid-borne (i.e., PAP) mutants.

The invention will be further described by reference to the following detailed examples. These examples are provided for purposes of illustration only, and are not intended to be limiting unless otherwise specified.

EXAMPLE 1

Construction of yeast expression vectors and analysis of PAP expression in yeast. The full length cDNAs corresponding to PAP and PAP-v disclosed in Lodge, and shown in Table I, were cloned into yeast expression vectors, under the control of the galactose inducible promoter, GAL1. *S. cerevisiae* was chosen as the expression system because yeast has the advantage of supplying eukaryotic cell-specific post-translational modifications. Since yeast ribosomes are sensitive to PAP, a regulated promoter was used to drive the expression of PAP. The cDNAs encoding PAP and PAP-v were cloned into the yeast expression vector pAC55, containing the selectable marker, URA3, as BglII/SmaI fragments under the control of the galactose inducible promoter pGal1. The vectors containing PAP (NT123) and PAP-v (NT124) were transformed into the yeast strain W303 (Mat a, ade2-1 trp1-1 ura3-1 leu2-3,112 his3-11, 15can1-100 ) (Bossie et al., Mol. Biol. C 3:875–93 (1992)), according to the procedure described in Ito et al., J. Bacteriol. 153:163–68 (1983), and transformants were selected on uracil minus medium with glucose at 30° C.

Yeast cells containing either NT123 (wild-type PAP) or NT124 (PAP-v) were grown in uracil minus medium with 2% raffinose at 30° C. for 48 h to a density of $5\times10^7$ cells/ml. PAP protein expression was induced by the addition of 2% galactose to half of the culture, while the other half of the culture was used as an uninduced control. The cells were allowed to grow for an additional 4 h and then collected by centrifugation at 10,000 g for 5 min. The cells were resuspended in RIPA buffer 9150 mM NaCl, 1% NP-40, 0.5% sodium deoxycholate, 0.1% SDS, 50 mM Tris-HCl, pH8) with protease inhibitors (0.1 μg/ml each of antipain, aprotinin, chymostatin, leupeptin, pepstatin) and lysed using glass beads (0.5 mm). Extracts were loaded on a 10% SDS-PAGE gel in accordance with the procedures described in Tomlinson, J. Gen. Virol., supra. Immunoblot analysis was performed by the enhanced chemiluminescence (ECL) method (Amersham), using antibodies against purified PAP.

Both PAP and PAP-v were expressed in yeast after galactose induction. Based on comparison with PAP protein standards, yeast cells containing the PAP plasmid (NT123) expressed both the mature form of PAP and a larger form, while cells containing the PAP-v (NT124) expressed predominantly the larger form and very low levels of the mature form. PAP was not detected in the culture medium. While not intending to be bound by any particular theory of operation, Applicant believes that these results suggest the following: (1) PAP is expressed as a precursor and processed to the mature form in yeast; and (2) PAP undergoes further processing in addition to the co-translational cleavage of the amino acid N-terminal signal peptide (Lodge) because the size of the mature PAP and the PAP expressed in yeast was found to be smaller than the expected size after the removal of the signal sequence.

In vitro translation and processing of PAP and PAP-v. To examine the processing of PAP in vitro, both constructs described in Example 1A were transcribed and translated in vitro using the T7 coupled reticulocyte lysate translation system in the presence of 35S-methionine with or without canine microsomal membranes (Promega). PAP and PAP-v cDNAs were cloned into the pGem3Z vector (Promega) downstream of the T7 promoter. An equal amount of DNA (1 μg) from each construct was transcribed and translated in vitro in the presence $^{35}$S-methionine, using the T7 coupled reticulocyte lysate translation system (Promega) with or without canine pancreatic microsomal membranes (Promega). Translation products were incubated with 0.2 mg/ml proteinase K in the presence of 5 mM EDTA and 125 mM sucrose for 90 min. Proteinase K was inactivated by addition of 4 mM PMSF and incubation at room temperature for 2 hours. Translation products were then treated with Endo-H (endo-N-acetylglucosaminidase) (1 mU/10 μl) in the presence of 0.1% SDS and 0.1M sodium citrate pH 5.5, at 37° C. for 12 hours. Equal amounts of protein (3.5 μl) were analyzed on 10% SDS-PAGE in accordance with the procedure described in Laemmli et al., Nature (London) 227:680–685 (1970).

PAP and PAP-v encode precursor proteins of 33 and 34 kD, respectively, and both precursors are processed to a 32 kD form after incubation with membranes. The processed proteins are still larger than the mature form (29 kD), indicating that the PAP precursor undergoes further post-translational processing. PAP does not contain any N-linked glycosylation sites and the size of the in vitro translated proteins did not change after treatment with Endo-H, which removes carbohydrate. These results indicated that the PAP precursors contain an N-terminal signal sequence which is co-translationally processed, and another sequence, which is post-translationally removed. Further evidence for C-terminal processing was obtained from X-ray structure analysis, which showed that mature PAP is 29 amino acids shorter at its C-terminus than the sequence predicted from the cDNA. See Monzingo et al., J. Mol. Biol. 233:705–715 (1993).

Growth of transformed yeast: In the presence of 2% raffinose, a non-repressing, non-inducing carbon source relative to GAL gene expression, the growth of yeast transformants containing NT123 or NT124 was indistinguishable from the transformants containing the vector alone. Growth of transformed yeast containing NT123 was arrested upon addition of the inducer, galactose, to the medium. Cells containing NT123 or NT124 did not grow on plates containing galactose. In the liquid medium, however, the extent of inhibition was greater with NT123 than NT124, possibly due to lower levels of mature PAP produced in yeast containing NT124. PAP expression was detected within 2 h of galactose addition to the medium. Maximal levels were reached in 6 to 8 h. Immunoblot analysis using antibodies against PAP, detected a maximal PAP level of 1 μg/mg yeast protein in NT123 transformants and 250 ng/mg yeast protein in NT124 transformants. These results were consistent with production of active PAP in yeast.

Mutagenesis of PAP plasmids. To isolate PAP mutants nontoxic to yeast, the expression plasmids containing PAP (NT123) or PAP-v (NT124) were mutagenized using hydroxylamine, transformed into yeast and cells were plated on medium containing glucose and replica plated to galactose containing plates. About 10 μg of the purified plasmid DNA were added to 500 μl of freshly prepared hydroxylamine solution (0.35 g hydroxylamine-HCl and 0.09 g NaOH in 5 ml of water) and incubated at 37° C. for 20 h. To stop the mutagenesis, 10 μl of 5M NaCl, 50 μl of 1 mg/ml BSA and 1 ml of 100% ethanol were added and the mutagenized DNA was precipitated by incubation at −70° C. for 10 minutes. The DNA was resuspended in TE and precipitated again. The DNA was then transformed into yeast and plated on uracil minus medium containing 2% glucose and replica plated on medium containing 2% galactose. The colonies that grew on galactose were analyzed for PAP expression by ELISA described in Lodge and by immunoblot analysis to identify the mutants which expressed hydroxylamine generated mutant PAP.

Growth of mutant yeast: Growth of mutants derived from NT123 on galactose containing medium was indistinguishable from growth on raffinose containing medium. Similar results were obtained with mutants derived from NT124. Analysis of protein accumulation in yeast indicated that the expression of wild type PAP, but not the hydroxylamine generated mutant PAP, resulted in decreased protein accumulation in yeast (data not shown).

After mutagenesis, the colonies growing on uracil deficient galactose plates were analyzed for PAP expression by ELISA using PAP antibodies and the positives were further analyzed by immunoblot analysis. Of a total of 28 mutants from NT123 mutagenesis, six different isolates expressed proteins which cross-reacted with PAP antibodies. Out of 44 mutants isolated from NT124 mutagenesis, 24 different isolates produced proteins which cross-reacted with PAP antibodies. Four mutants (HMNT123-1, 124-6, 124-7, and 124-1) produced proteins which were larger than the mature form of PAP (29 kD), suggesting that the processing of PAP to the mature form is blocked in these mutants. Two mutants (HMNT123-2 and 123-3) produced proteins that co-migrated with the mature form of PAP, while several others (HMNT123-4, 123-5, 123-6, 124-2 and 124-3), produced smaller proteins. The protein expression levels in the mutants ranged from 0.005 to 0.08% of total soluble protein.

Nucleotide sequence analysis of PAP mutants: The positions of the amino acid alterations in the PAP mutants were identified by sequence analysis of the plasmids rescued from yeast. Plasmids were isolated from the mutants, transformed into *E. coli* according to the procedure set forth in Rose et al., supra, and sequenced using the Sequenase 2.0 DNA sequencing kit (ISB). See Robzyk et al., Nucl. Acids Res. 20, 3790 (1992). Sequence analysis of HMNT123-2 revealed that it contains a single point mutation, changing the glutamic acid at position 176 to valine(E176V) at the putative active site (Table II). HMNT123-2 produced a protein of the same size as the wild type PAP. Glutamic acid at position 176 (E176) is highly conserved among all RIPs sequenced to date and it is proposed to be at the active site cleft of PAP. See Stevens et al., Experientia 37:257–259 (1981). HMNT123-6, HMNT124-2 and HMNT124-3 all had a point mutation near the C-terminus which introduced a stop codon instead of a tryptophan at position 237 (W237) (Table II). As a result of this mutation, 26 amino acids were deleted from the C-terminus of the mutant PAP, and a truncated protein was produced. HMNT123-5 contained a frameshift mutation, which deleted two nucleotides (GA) at about the codon for Glu 184 (GAG), whereby the reading frame was altered and the Asn190 codon became TAA, because the reading frame shifted to the −1 position, resulting in expression of a truncated protein. A point mutation in HMNT124-1 changed the glutamic acid at position 97 to lysine (E97K) (Table I). HMNT123-1 also contained a single point mutation, at position 75, changing glycine to valine (G75V). Both of these mutants expressed a larger protein than purified mature PAP, suggesting that processing of PAP is inhibited in these mutants.

To confirm that the observed mutant phenotypes were due to the mutations identified in the PAP sequence, and not due to a chromosomal mutation, each mutant PAP plasmid was isolated and retransformed into the host strain, W303, and URA+transformants were selected. These transformants grew at wild type rates on galactose containing medium, indicating that the ability of the transformants to survive induction of PAP expression is plasmid-linked.

TABLE II

Mutations which abolish the toxicity of PAP to eukaryotic cells

| | |
|---|---|
| HMNT123-1 | Gly-75 (GGT) --> Val (GTT) |
| HMNT123-2 | Glu-176 (GAG) --> Val (GTG) |
| HMNT123-4 | Trp-208 (TGG) --> Stop (TAG) |
| HMNT123-5 | Glu-184 (GAG) --> Glu (GAA) |
| HMNT123-6 | Trp-237 (TGG) --> Stop (TAG) |
| HMNT124-1 | Glu-97 (GAA) --> Lys (AAA) |
| HMNT124-2 | Trp-237 (TGG) --> Stop (TAG) |
| HMNT124-3 | Trp-237 (TGG) --> Stop (TAG) |
| HMNT124-13 | Leu-202 (CTT) --> Phe (TTT) |

Enzymatic activity of PAP mutants: An in vitro translation assay was used to compare the enzymatic activity of PAP mutants. Brome mosaic virus (BMV) RNA was translated in the rabbit reticulocyte lysate system (Promega) in the presence of extracts from yeast containing different amounts of PAP, as described in Lodge. PAP levels in yeast were quantitated by ELISA (Lodge). The inhibition curves were linear in the range of 0.1 to 1 ng PAP/ml. Table III shows the results of the protein synthesis inhibition assay carried out in the presence of 0.2 ng/ml PAP from yeast. The amount of total protein and PAP were adjusted to 87 ng/ml and 0.2 ng/ml, respectively in each extract by adding either wild type yeast extract or RIPA buffer. In previous experiments, when in vitro translation was performed in the presence of 0.2 ng/ml BSA, no inhibition of translation was observed. When 0.2 ng/ml protein from nontransformed yeast (WT) were added, a slight inhibition of translation was observed. Translation was inhibited in the presence of 0.2 ng/ml of: (1) purified PAP added to wild type yeast extract (WT+PAP); (2) protein extracts from yeast containing NT123 or NT124; and (3) protein extracts from yeast containing the hydoxylamine generated mutants HMNT123-3, HMNT124-1, HMNT124-3 and HMNT124-13. In contrast, protein extracted from HMNT123-2 did not inhibit protein synthesis in the reticulocyte lysate system. Similar results were obtained when in vitro translation experiments were performed using 0.1 ng/ml PAP.

TABLE III

Inhibition of protein synthesis by PAP mutants

| Protein added to translation medium | Protein synthesis (cpm incorporated) |
|---|---|
| No RNA | 2,246 +/- 204 |
| BSA | 244,956 |
| WT | 176,723 ± 713 |
| PAP+WT | 146,660 ± 2474 |
| NT123 | 110007 ± 445 |
| HMNT123-2 | 213 952 ± 767 |
| HMNT123-3 | 134,202 ± 5522 |

TABLE III-continued

Inhibition of protein synthesis by PAP mutants

| Protein added to translation medium | Protein synthesis (cpm incorporated) |
|---|---|
| HMNT124 | 84,959 ± 661 |
| HMNT124-1 | 119529 ± 2094 |
| HMNT124-3 | 132,955 ± 3739 |
| HMNT124-13 | 145,899 ± 4457 |

EXAMPLE 2

Expression of PAP Mutants in Transgenic Tobacco

Mutant PAPs were engineered for constitutive expression in plants to determine if they would be non-toxic to plants, and if they could retain PAP antiviral properties.

In order to insert the PAP genes into the plant expression vectors, the plasmid DNA encoding the mutant PAPs was isolated from yeast, transformed into *E. coli* as described in the Example 1. The plasmid DNA encoding the mutant PAPs was isolated from *E. coli* digested with HindIII, the HindIII site was filled in with klenow DNA polymerase and the plasmid was digested with SacI to isolate the 772 bp SacI/HindIII fragment encoding the mutant PAP. The SacI/HindIII fragments encoding the mutant PAPs were cloned into pMON8443 (Lodge) after digestion with SacI and SmaI to remove the wild type PAP cDNA inserts. The SacI/HindIII fragment from HMNT123-2 was cloned into SacI/SmaI digested pMON8443 to generate NT144 and the SacI/HindIII fragment from HMNT124-3 was cloned into SacI/SmaI digested pMON8443 to generate NT145. NT146 and NT147 were generated by replacing the 772 bp SacI/HindIII fragment of the wild type PAP cDNA insert in pMON8443 with the 772 bp SacI/HindIII fragment of HMNT123-2 and HMNT124-3, respectively.

Plasmids NT144, NT145, NT146 and NT147 were mobilized into the ABI strain of *Agrobacterium tumefaciens* for transformation into tobacco and potato (Lodge). For transformation of *N. tabacum*, young leaves from one month-old tobacco plants were covered with water for 20–30 min. The water was drained off and the leaves were covered with 10% chlorox and 0.04% Tween 20 for 15 minutes and then rinsed three times with water. Leaf disks were cut with an autoclaved single hole punch and placed upside down on MS104 medium (4.4g/l MS salts, 30 g/l sucrose, B5 vitamins, 0.1 mg/l NAA and 1.0 mb/l BA) for 1 day for preculture. The precultured disks were placed in a 50 ml tube and inoculated with an overnight culture of Agrobacterium that was diluted 1:5. The tube was inverted several times. The disks were then taken out and blotted on sterile filter paper and placed upside down on MS104 feeder plates with a filter disk to co-culture for 2 days. Leaf disks were then transferred to MS104 media with selection (100 μg/ml kanamycin and 300 μg/ml cefataxime) and placed in an incubator. Calli and shoots appeared in about three weeks. Shoots were transferred to plantcons with MSO media (4.4 g/l MS salts, 30 g/l sucrose and B5 vitamins) with selection. Roots formed in two weeks, rooted shoots were then transferred to soil and kept in a high humidity environment. The regenerated plants were then screened by ELISA for the presence of neomycin phosphotransferase (NPTII) to identify the expressors.

Transformation frequencies of *N. tabacum* cv Samsun typically range between 10 to 12% (number of transgenic plants obtained per leaf disk). As previously reported the transformation frequency of *N. tabacum* was significantly reduced when vectors containing the wild type PAP (pMON8443) or the variant PAP (pMON8442) were used in transformation (Lodge). In contrast, as shown below in Table IV, no decrease in transformation frequency was observed when vectors containing the nontoxic mutant PAPs were used in the transformation.

TABLE IV

| Plasmid | Frequency of transformation |
|---|---|
| NT144 | 13% |
| NT145 | 11% |
| NT147 | 12% |

As previously reported, the transgenic plants expressing wild type PAP or the variant PAP showed growth reduction, chlorosis and mottling on their leaves (Lodge). In contrast, the transgenic plants expressing the mutant PAPs were phenotypically normal. They grew at the same rate as the wild type plants and showed no chlorosis or mottling on their leaves, indicating that the expression of the mutant PAPs is not toxic to transgenic plants. The mutant PAPs were also expressed in *E. coli* and their expression did not affect the growth rate of *E. coli* cells, indicating that they are not toxic to *E. coli.*

EXAMPLE 3

Antiviral Activity of Mutant PAP Expressed in Transgenic Tobacco

Transgenic tobacco (*N. tabacum* cv Samsun) plants were assayed by ELISA (Lodge) to determine the level of expression of the mutant PAPs. In Table V, the level of expression of the mutant PAP is compared with the level of expression of the variant PAP (pMON8442) (Lodge) expressed in transgenic plants.

TABLE V

Level of PAP expression in transgenic tobacco

| Plant number | Level of expression |
|---|---|
| NT144-12 | 1.5 μg/mg |
| NT144-13 | 0.9 μg/mg |
| NT145-13 | 4.4 ng/mg |
| pMON8442(26139-11) | 9.6 ng/mg |

As shown in Table V, the transgenic plant containing the C-terminal deletion mutant (NT145-13) expressed similar levels of mutant PAP as the plant expressing the PAP variant (pMON8442) (Lodge). In contrast, transgenic plants containing the active site mutant (NT144) expressed significantly higher levels of the mutant PAP.

To test if the PAP mutants (the NT144 and NT145 constructs) had antiviral activity in vitro, wild type tobacco plants were inoculated with potato virus X (PVX) in the presence of protein extracts from plants expressing the mutant PAP, the PAP-v (pMON8442) and nontransformed (wild type) tobacco. PAP levels in the transgenic plants were quantitated by ELISA. The level of PAP expression in line 145-13 was 4.4 ng/mg and the level of PAP expression in line 144-12 was 1.5 μg/mg. Plants were inoculated with extracts from transgenic plants containing 5 ng PAP per leaf and 1.1 mg total protein. Protein extract was prepared from nontransformed tobacco leaves (WT). Fifty μl of 1 g/ml PVX was inoculated onto tobacco leaves in the presence of different amounts of total protein from nontransformed tobacco, ranging from 6.7 μg to 1.1 mg. Twenty tobacco plants were inoculated with 50 μl of 1 μg/ml PVX in the presence of 6.7 μg–1.1 mg of total protein from nontransformed plants. As shown in Table VI, all WT plants became infected with PVX and showed local lesions, systemic symptoms and virus accumulation in the leaves above the inoculated leaves (systemic leaves). These results demonstrate that protein extracts from nontransformed tobacco plants do not have any effect on PVX infection. When protein extract from nontransformed tobacco plants was used in the presence of 5 and 10 ng purified PAP (WT+PAP), lower numbers of PVX lesions were observed on inoculated leaves, indicating that tobacco plants were protected from PVX infection in the presence of purified PAP. However, although fewer lesions were obtained on the inoculated leaves of these plants, they showed systemic symptoms and similar levels of PVX antigen as the plants inoculated with PVX in the presence of extracts from nontransformed tobacco plants (WT).

TABLE VI

Effects of PAP mutants on PVX infection of tobacco leaves[1].

| Plant Extract[a] level (ng/mg)[c] | PAP ng/(leaf) | mean no. of lesions[b] | PVX antigen |
|---|---|---|---|
| WT[d] | 0 | 66.6 ± 10.1 | 4.4 ± 1.4 |
| WT + PAP[e] | 5 | 9.0 ± 2.0 | 3.1 ± 1.9 |
| | 10 | 1.5 ± 2.0 | 2.8 ± 2.6 |
| 26139 | 5 | 1.8 ± 2.9 | NA |
| 145-13 | 5 | 12.5 ± 7.4 | 0.2 ± 0.3 |
| 144-12 | 5 | 57.8 ± 7.4 | 3.2 ± 2.5 |
| | 10 | 56.1 ± 4.9 | 2.5 ± 1.4 |
| | 20 | 55.5 ± 13.8 | 4.3 ± 1.4 |
| | 50 | 53.3 ± 14.9 | 2.8 ± 0.3 |
| | 100 | 68.0 ± 11.7 | 3.0 ± 0.9 |

[a]Plant extract was prepared from either non-transformed or transformed tobacco leaves with plant expression vector (pMON8442, NT145, and NT144).
[b]The number of lesions were counted at 9 days post-inoculation.
[c]Three leaf discs in a tube were taken from 1st, 2nd and 3rd systemic leaves at 12 days post inoculation and then homogenized in ELISA buffer. The average levels of PVX antigen were quantified by ELISA. The amount of total proteins in each extract were quantified by BCA reagent (Pierce).
[d]Protein extract was made from non-transformed tobacco leaves.
[e]PAP (Calbiochem) was added to a protein extract from non-transformed tobacco leaves.
[1]Twenty plants for wild-type(wt), ten plants for wt + PAP and five plants for each transgenic protein extract were used. Two leaves from each plant were inoculated with 50 μl of PVX (1 μg/ml) in the presence of different amount of PAP or PAP mutants.

When PVX was inoculated in the presence of 5 ng protein from the transgenic plant (26139) expressing the variant PAP (pMON8442), significantly lower numbers of lesions were observed on the inoculated leaves and these plants escaped systemic infection. Similarly, when PVX was inoculated in the presence of 5 ng protein from transgenic plant (145-13) expressing the C-terminal deletion mutant, significantly fewer lesions were obtained. These plants did not show systemic symptoms and the PVX antigen levels were significantly reduced on the inoculated leaves. In contrast, when PVX was inoculated in the presence of 5 to 100 ng protein from transgenic plant expressing the active site mutant (144-12), the numbers of lesions observed on the inoculated leaves was similar to the numbers of lesions observed on plants inoculated in the presence of protein from nontransformed tobacco plants (WT). Systemic symptoms were observed on these plants and PVX antigen levels in the systemic leaves were comparable to the antigen levels in plants inoculated with PVX in the presence of extracts from nontransformed tobacco plants. These results demonstrate that the C-terminal deletion mutant which is enzymatically active in vitro retains its antiviral activity in vitro. In contrast, the active site mutant which is enzymatically inactive in vitro, does not retain its antiviral activity in vitro, suggesting that the enzymatic activity of PAP is critical for antiviral activity in vitro.

EXAMPLE 4

Expression of PAP Mutants in Transgenic Potato

Potato stems were cut into 3 mm pieces and placed in sterile water. Agrobacterium containing NT144, Nt145, NT146 and NT147 was grown overnight. Cells were spun down and resuspended in 10 ml of water. Agrobacterium was diluted again 1:10 in water. Water was removed from potato stem explants and the diluted Agrobacterium was added. The stem explants were incubated with Agrobacterium for 15 min. The bacteria were removed and the explants were placed on 1/10 MSO plates that had been covered with sterile Whatman #1 filters. MSO contains 4.4 g MS salts, 30 g sucrose and 1 ml B5 vitamin (500×) in a 1 liter volume, pH 5.7. After a two day co-culture period in the dark, the explants were placed on PC media, containing MSO plus 0.5 mg/l zeatin riboside (ZR), 5 mg/l $AgNO_3$ and 0.1 mg/l NAA (naphthaleneacetic acid) 100 mg kanamycin and 300 mg cefataxime per liter, for four weeks. After 4 weeks, the explants were placed on PS media which contains MSO plus 5 mg/l ZR, 0.3 mg/l giberellic acid, 100 mg kanamycin and 300 mg cefataxime per liter. Shoots began to appear in four to eight weeks. Shoots were then removed and placed in plantcons containing PM media (4.4 g MS salts, 30 g sucrose, 0.17 g $NaH_2PO_4H_2O$, 1 ml thiamine HCl and 0.1 g inositol in a 1 liter volume, pH 6.0 and 0.2% gelrite agar). Plants were then placed in soil, hardened off and analyzed by NPTII ELISA to identify the transgenic plants. Transgenic potato plants were then analyzed by ELISA for PAP expression. Transgenic potato plants expressing NT144, NT145 and NT146 were identified by ELISA. The transformation frequencies were not affected when constructs containing mutant PAPs were used and the transgenic plants expressing mutant PAPs were phenotypically normal, indicating that the expression of the mutant PAPs is not toxic to potato.

EXAMPLE 5

Expression of PAP Mutants in Transgenic Turfgrass

Mutant PAPs were engineered for constitutive expression in monocots. Creeping bentgrass (*Agrostis palustris*, Huds.), which is a turfgrass used in golf courses, fairways, tees and lawns, was used as the monocot species for transformation. In order to construct an expression vector for monocots, NT168 was created by cloning the promoter and the first intron of the maize ubiquitin gene (Toki et al., Plant Physiol. 100:1503–1507 (1992)) into pMON969. pMON969 was digested with HindIII and BglII to remove the CaMV 35S promoter region. The plasmid pAHC20, containing the ubiquitin promoter and the first intron (Toki) was digested with HindIII and BamHI to isolate the 2016 bp HindIII/BamHI fragment which was ligated to HindIII/BglII fragment of pMON969 to generate NT168. The cDNA fragments encoding the mutant PAPs were isolated by digesting NT144 and NT145 with BglII and BamHI and cloned into the BamHI site of NT168. The monocot expression vectors containing the mutant PAP cDNAs were then used in transformation along with pSL12011, which contains the selectable marker, the bar gene (Hartmann et al., Biotechnology 12:919–923 (1994). Turfgrass transformation was carried out using two different methods, biolistic transformation using the particle gun and by protoplast transformation as described below.

Embryogenic callus cultures were initiated from surface sterilized seeds of 7 creeping bentgrass cultivars: 'Cobra', 'Emerald', 'PennLinks', 'Providence', 'Putter', 'Southshore', and 'SR1020' and used in biolistic transformation, as described in Hartmann. Callus initiation media were MS basal medium and MS vitamins, supplemented with 100 mg $L^{-1}$ myo-inositol, 3% sucrose, and either 150 mg $l^{-1}$ asparagine and 2 mg $L^{-1}$ 2,4-D for MSA2D, Or 500 mg $L^{-1}$ casein hydrolysate, 6.6 mg $L^{-1}$ dicamba, and 0.5 mg $L^{-1}$ 6-BA for MMS. Media were solidified with 0.2% Phytagel® (Sigma). After 4 to 6 weeks in the dark at 25° C., embryogenic callus lines were selected and transferred to fresh medium. Suspensions were established from embryogenic callus cultures by adding 1 to 2 g callus to 250 ml flasks with 50 ml liquid media, incubate in the dark at 25° C. with shaking at 120 rpm and subcultured twice a week.

Plates were prepared for particle bombardment by placing 1 ml of suspension cells on 5.5 cm filter disks in plates containing MSA2D media with the addition of 0.4 M mannitol. Plates were prepared 20 h prior to bombardment and kept in the dark. Gold particles were prepared by heating at 95° C. in 100% ethanol for 30 min, centrifuged briefly and resuspended in fresh ethanol. The particles were sonicated for 10–30 min in a water bath, washed 3 times in sterile, distilled water, and resuspended in water. DNA samples consisting of 50 µl (5 mg) gold suspensions, 10 µg target DNA, 50 µl 2.5M $CaCl_2$, and 20 µl 0.1 M spermidine, were vortexed, centrifuged, and resuspended in ethanol. The ethanol wash was repeated for a total of 3 times. The final pellet was resuspended in 30 µl ethanol, and 5 µl of DNA solution were used per shot. Bombardment was carried out using the Bio-Rad PDS-1000, He Biolistic Delivery System at 1100 psi. Calli from the bombardment experiments were plated out on MSA2D medium containing 2 or 4 mg/l of bialaphos for selection 34 days after bombardment and continued for 8 wks without transfer. After 8 wks on plate selection, calli were transferred to MS media without hormones for regeneration. Regenerates appeared within 2–8 wks. Shoots were transferred to Plantcons containing MS medium and roots appeared within 24 wks.

For protoplast transformation, protoplast isolation was performed four days after subculture. Cells were incubated with filter-sterilized enzyme solution containing 1% (w/v) Cellulase Onozuka RA (Yakult Pharmaceutical Co. LTD), 0.1% Pectolyase Y-23 (Seishin Pharmaceutical Co. LTD), and 0.1% MES (2-[N-morpholino]ethane-sulfonic acid) (Sigma) in culture media (MSA2D or MMS with 5% mannitol) for 4 hours at 28° C. with shaking at 50 rpm. About 1 g fresh weight of suspension cultures was treated with 10 ml of enzyme solution. Protoplasts were filtered through Miracloth and washed twice with culture medium containing 5% mannitol. Mannitol was used as an osmotic stabilizing agent. Protoplasts were cultured using a feeder layer system). The washed, filtered protoplasts were pipetted onto a black nitrocellulose membrane placed over a feeder layer of suspension cells which had been spread on 5% mannitol culture medium. One week later, the membranes with protoplasts were transferred to a fresh feeder layer on 3% mannitol culture plates. Protoplasts were removed from the feeder layer 2 weeks after isolation. Plating efficiency was determined by dividing the number of visible colonies 3 weeks after isolation by the total number of protoplasts plated. Plants were regenerated by placing protoplast derived calli on MS medium without hormone or with 1 mg $L^{-1}$ 6-BA or kinetin. After 4 to 5 weeks shoots were transferred to Plantcon® 4 with MS medium containing no hormone for rooting. Protoplasts were transformed using either PEG or electroporation at 170 volts $cm^{-1}$ using a Gene-Pulster (Bio-Rad). In PEG experiments, freshly isolated protoplasts were resuspended at a density of $1\times10^7$ protoplasts per ml in 5% mannitol containing 15 mM $MgCl_2$ and 0.1% MES. Approximately 0.3 ml protoplasts were incubated with 20 to 40 µg plasmid DNA and 13% PEG for 10 to 15 min., diluted stepwise and resuspended in culture medium with 5% mannitol (pH 5.8) after centrifugation. In electroporation experiments, protoplasts were resuspended at a density of $5\times10^6$ protoplasts per ml in cold filter sterilized electroporation buffer containing 5.2 g $L^{-1}$ KCl, 0.835 g $L^{-1}$ $CaCl_2$, 0.976 g $L^{-1}$ MES and 5% mannitol at pH5.8. About 0.8 ml protoplasts were mixed with 20 µg DNA by inversion, electroporated at 170 volts $cm^{-1}$ and placed on ice for 15 min., then diluted to a total of 3 ml with culture medium containing 5% mannitol. Selection with 4 mg $L^{-1}$ of bialaphos was initiated 16 days after protoplast isolation and transformation. Resistant colonies were selected on MS medium without hormone, with 6-BA or kinetin as described above. Shoots were transferred to Plantcons® for rooting. A commercial formulation of bialaphos under the trade name Herbiace® (Meiji Seika Kaishya, LTD.) was used in greenhouse herbicide tests. Herbicide rates for Herbiace® were established using control plants, and were based on the commercial rate of 0.75 lb AI/acre (1× the field rate). The herbicide was applied to all the tillers above ground with an artist's paint brush at the rat of 120 ml per flat. Dimension of the flat is 0.1431 $m^2$ and it holds 96 or 24 plants.

EXAMPLE 6

Expression of the Mutants in Transgenic Tobacco Plants and Resistance to Viral Infection A. Expression of PAP Mutants in Transgenic Tobacco To determine if enzymatic activity of PAP is required for its antiviral activity, the cDNA encoding the active-site mutant NT123-2 was cloned into the plant expression vector pMON8443 after removing the wild type PAP insert, to generate NT144, as described in Example 2. Similarly, the cDNA encoding the C-terminal deletion mutant, NT124-3 was cloned into pMON8443 to generate NT145 and NT147, as described in Example 2. Expression of the mutant PAPs was driven by the enhanced CaMV3SS promoter. NT144, NT145 and NT147 were mobilized into *Agrobacterium tumefaciens* for transformation into tobacco. Transformation frequencies of *Nicotiana tabacum* cv Samsun typically range between 10 to 12% based on the number of transgenic plants obtained per leaf disk (Lodge). The transformation frequency was 13% using NT144 and 11% using NT145. The transgenic plants expressing the active-site mutant or the C-terminal deletion mutant were phenotypically normal. They grew at the same rate as wild type plants and did not show chlorosis or mottling in their leaves, indicating that the expression of the mutant PAPs was not toxic to transgenic tobacco. These results are in contrast to the previously reported results (Lodge) in which the transformation frequencies of *N. tabacum* were reduced to 0.7% when using a vector containing PAP (pMON8443), and to 3.7% when using a vector containing PAP-v (pMON8442), both of which are enzymatically active (Lodge). Lodge did not recover any transgenic plants expressing high levels of PAP, and the transgenic plants expressing high levels of PAP-v showed growth reduction, chlorosis, and mottling in their leaves.

Regenerated transgenic plants were first analyzed for expression of neomycin phosphotransferase (NPTII) by ELISA. The NPTII positive plants were then analyzed for PAP expression by ELISA and immunoblot analysis. Eleven different transgenic plants expressed detectable levels of the active-site mutant by ELISA. Plants expressing the active-site mutant PAP produced a 29 kDa protein which comigrated with mature PAP, indicating that the active-site mutant PAP is fully processed to the mature form in transgenic plants (data not shown). Transgenic plants expressed significantly higher levels of the active-site mutant than the plants expressing PAP or PAP-v. No bands corresponding to PAP were detected in wild type tobacco or in transgenic tobacco expressing β-glucuronidase. The C-terminal deletion mutant was expressed at significantly lower levels than the active-site mutant.

B. Antiviral Activity of the Active-site Mutant in Transgenic Tobacco

In order to determine if transgenic lines expressing the active-site mutant PAP are resistant to virus infection, progeny of transformed plant lines were inoculated with PVX. Self-fertilized progeny were screened for the presence of PAP by ELISA. PAP levels in the progeny of the transgenic lines varied depending on the age of plants and growth conditions. The degree of variability in PAP levels was similar to that previously reported for transgenic lines expressing PAP or PAP-v (Lodge). Ten progeny from each transgenic line expressing the active-site mutant PAP (144-1 and 144-7), PAP-v (26139-19), PAP (33617-11) and 10 nontransformed tobacco plants were inoculated with 1 µg/ml PVX. Symptom development on both inoculated and systemic leaves was monitored visually each day up to 21 days post-inoculation. In addition, disks from the inoculated leaves and from the first, second and third systemic leaves of each plant were sampled at 12 days post-inoculation in order to quantitate virus replication and spread.

As shown in Table VII, transgenic plants expressing PAP-v or the wild type PAP did not develop any lesions on the inoculated leaves at nine days post-inoculation. In contrast transgenic plants expressing the active-site mutant had as many lesions on their inoculated leaves as the control plants. ELISA analysis of systemic leaves showed that 90% of wild type tobacco plants were systemically infected by PVX at 12 days post-inoculation, while only 30 and 40% of the transgenic plants expressing PAP and PAP-v, respectively, showed systemic PVX infection. In contrast, 100% of the plants expressing the active-site mutant were infected with PVX (Table VII). Similar results were obtained when plants were scored again at 21 days post inoculation.

TABLE VII

| Plant Line | PAP expressed | Level of PAP (ng/mg)[a] | Number of lesions[b] | % of plants showing systemic infection[c] |
|---|---|---|---|---|
| WT | | 0 | 77 +/− 12 | 90 |
| 26139-19 | PAP-v | 5.6 +/− 2.6 | 0** | 30** |
| 33617-11 | PAP | 0.6 +/− 0.02 | 0** | 40* |
| 144-1 | E176V | 43.8 +/− 4.8 | 78 +/− 16 | 100 |
| 144-7 | E176V | 46.2 +/− 5.6 | 72 +/− 11 | 100 |

[a]PAP levels were quantitated by ELISA after taking four leaf disks from twenty plants per line. Mean values +/− SD are shown.
[b]Ten plants from each line were inoculated with 50 µl of 1 µg/ml PVX on two leaves per plant. The number of lesions were counted 9 days post inoculation. Mean values +/− SD are shown.
[c]Three leaf disks were taken from 1st, 2nd and 3rd systemically infected leaves at 12 days post inoculation and viral antigen levels were quantitated by ELISA. The amount of total protein in each extract was quantitated using the BCA kit (Pierce).
**Significantly different from wild type at 1% level
*Significantly different from wild type at 5% level To determine if transgenic plants expressing higher levels of the active-site mutant are also susceptible to PVX infection, homozygous progeny (R2 generation) of transgenic link 144-12, which expressed the highest levels of the active-site mutant PAP were inoculated with 0.5 μg/ml PVX. As shown in Table VIII below, transgenic lines producing high levels of the active-site mutant had the same numbers of lesions as the wild type tobacco plants in their inoculated leaves, while progeny of transgenic plants which expressed PAP-v or PAP had significantly lower numbers of lesions. ELISA analysis of the systemic leaves demonstrated that by 21 days post inoculation, 90% of wild type tobacco plants and 100% of the transgenic plants expressing the active site mutant were infected with PVX. In contrast, plants expressing PAP or PAP-v had fewer lesions on the inoculated leaves and lower percentages of these plants became systemically infected with PVX.

In additional experiments, progeny of seven different transgenic lines expressing the active-site mutant were analyzed for their susceptibility to PVX infection; none of these lines showed resistance to PVX (data not shown).

TABLE VIII

Susceptibility of transgenic tobacco plants expressing the C-terminal deletion mutant (W237Stop) to PVX infection

| Plant Line | PAP expressed | Level of PAP (ng/mg)[a] | Number of lesions[b] | % of plants showing systemic infection[c] 12 dpi | 21 dpi |
|---|---|---|---|---|---|
| WT | | 0 | 24 +/− 15 | 90 | 90 |
| 26139-19 | PAP-v | 9.6 | 1 +/− 2** | 10** | 30** |
| 33617-11 | PAP | 1.6 | 11 +/− 4** | 10* | 40* |
| 144-12 | E176V | 1500 | 23 +/− 13 | 100 | 100 |
| 147-19 | W237Stop | 4.5 | 12 +/− 10** | 20** | 60 |
| 145-13 | W237Stop | 4.4 | 6 +/− 4** | 30** | 60 |

[a]PAP levels were quantitated by ELISA in the primary transgenic plants.
[b]Eight to ten plants from the homozygous progeny (R generation) of each transgenic line were inoculated with 50 μl of 0.5 μg/ml PVX on two leaves per plant. The number of lesions were counted 12 days post inoculation. Mean values +/− SD are shown.
[c]Two leaf disks were taken from first and second systemically infected leaf from each plant at 12 days post-inoculation and two leaf disks were taken from third and fourth systemically infected leaf at 21 days post-inoculation. Viral antigen levels were quantitated by ELISA. The amount of total protein in each extract was quantitated using the BCA kit (Pierce).
**Significantly different from wild type at 1% level
*Significantly different from wild type at 5% level C. Antiviral Activity of C-terminal Deletion Mutant in Transgenic Tobacco In order to determine if transgenic lines expressing the C-terminal deletion mutant are resistant to virus infection, homozygous progeny (R2 generation) from transgenic lines 145-13 and 147-19 expressing the C-terminal deletion mutant (W237Stop) were inoculated with 0.5 μg/ml PVX and the numbers of lesions were counted at 12 days post-inoculation. As shown in Table VIII above, plants from transgenic lines 145-13 and 147-19 had significantly lower numbers of lesions on their inoculated leaves compared to the wild-type plants. At 12 days post inoculation, only 20 and 30% of the plants from the transgenic lines 147-19 and 145-13, respectively, showed systemic symptoms and contained PVX antigen by ELISA, while 90% of the control plants were infected with PVX. By 21 days post-inoculation, there was an increase in the percentage of plants from lines 147-19 And 145-13 that showed systemic symptoms. As observed in previous tests, progeny of transgenic lines expressing PAP-v and PAP were protected from PVX infection. Infected plants expressing the C-terminal deletion mutant (W237Stop), PAP or PAP-v showed milder symptoms compared to the infected wild-type plants or transgenic plants expressing the active-site mutant (E176V). ELISA analysis was used to quantitate viral antigen levels in transgenic plants and wild-type plants at 21 days post-inoculation. PVX antigen levels were lower in plants from lines 147-19, 145-13, and 33617-11 compared to the antigen levels wild type plants. The percentages of infected plants did not change when they were scored again at 4 weeks post inoculation.

In additional experiments, a total of six different transgenic lines expressing the C-terminal deletion mutant were analyzed for their susceptibility to PVX infection and four of these lines showed resistance to PVX infection (data not shown).

EXAMPLE 7

Analysis of Fungal Resistance in Transgenic Plants Expressing PAP and PAP Mutants Seedlings of transgenic tobacco lines expressing PAP, PAP mutants and wild-type tobacco seedlings were used. Four weeks after germination seedlings were transferred into growth chamber and were grown in the sterile soil at 25° C., 80% relative humidity, and 16-hour photoperiod. Recombinant constructs with chimeric PAP genes were introduced into *Agrobacterium tumefaciens* via triparental mating. Agrobacterium containing the modified PAP genes were used to transform *Nicotiana tabacum* cv. Samsun. Kanamycin resistant $R_2$ transgenic plants were self-pollinated, and $R_3$ seedlings were used in the experiments. Transgenic plants from lines 33617 (expressing wild type PAP), NT144 (expressing active-site mutant PAP), NT145, and NT147 (both expressing C-terminal deletion mutant PAP) were used.

Four week-old transgenic and control seedlings were transplanted into sterile soil and inoculated with soil-borne fungal pathogen *Rhizoctonia solani*. Development of disease symptoms was observed for two weeks and the seedling mortality rates were calculated. Plants that survived the fungal infection were transplanted into individual pots and samples of tissue were taken for further analysis.

Following inoculation with *R. solani*, control tobacco seedlings were very quickly overcome by fungal pathogen. The disease progressed rapidly, affecting more than 30% of control seedlings in six days post-inoculation. In contrast, the transgenic lines susceptibility to infection was significantly lower. Six days post-inoculation, only 9.5% of the seedlings from the lines with wild-type PAP, about 20% of seedlings from the C-terminal truncated PAP line, and 23% of the seedlings from the active-site mutant line were affected. The number of seedlings that survived at different time points is shown in Table IX below. All transgenic lines exhibited a delay in appearance of disease symptoms and a lower mortality rate.

TABLE IX

Progression of disease in transgenic tobacco PAP lines infected with *Rhizoctonia solani.*

| Tobacco line | Number of seedlings survived post-inoculation | | | |
|---|---|---|---|---|
| | 0 days (%) | 6 days (%) | 10 days (%) | 14 days (%) |
| wild type | 40 (100) | 27 (67.5) | 25 (62.5) | 25 (62.5) |
| 33617-11 | 42 (100) | 38 (90.5) | 35 (83.3) | 34 (81.0) |
| 145-15-3 | 37 (100) | 29 (78.4) | 26 (70.3) | 23 (62.2) |
| 147-19-25 | 39 (100) | 32 (82.1) | 29 (74.4) | 28 (71.8) |
| 144-12-3 | 39 (100) | 30 (76.9) | 29 (74.4) | 29 (74.4) |

In a separate experiment, with a different strain of *Rhizoctonia solani*, the disease progressed very rapidly, essentially killing the majority of seedlings in five days. Seedling survival after two weeks of growth in the infected soil is shown in Table X below. Noticeably, control plants, although not dead at the scoring time point, were extremely stunted, and exhibited very severe disease symptoms. In contrast, seedlings in transgenic lines with truncated PAP showed much less tissue damage.

TABLE X

Survival of transgenic tobacco lines with different PAP genes in *Rhizoctonia solani* resistance test

| Tobacco line (Samsun) | Number of seedlings planted | Number of seedlings survived 14 days postinoculation | % seedlings survived 14 days postinoculation |
|---|---|---|---|
| control (n) | 20 | 2 | 10 |
| control (N) | 20 | 0 | 0 |
| 33617-11 | 20 | 8 | 40 |
| 144-12 | 20 | 5 | 25 |
| 145-15 | 20 | 1 | 5 |
| 147-19 | 20 | 5 | 25 |

Analysis of Surviving Plants

Analysis of the total cellular protein from transgenic lines was performed by separating protein samples on 10% SDS-PAGE using a Mini-PROTEAN II electrophoresis cell (Bio-Rad) and proteins were transferred onto nitrocellulose membrane using Bio-Rad Trans-Blot semi-dry electrophoretic transfer apparatus according to manufacturer's instructions. Western blot analysis was performed using PAP IgG or PR1a monoclonal antibodies. Detection was by enhanced chemiluminescence using DuPont Renaissance kit.

Western blot analysis of cellular extracts from transgenic plants showed that the PAP gene is expressed in all plants that survived the fungal infection. The amount of PAP produced differed among individual plants. In addition, apoplastic fluid was isolated from the same plants and extracellular proteins were analyzed by staining the native gel with silver nitrate. Expression of pathogenesis-related proteins (PR) was detected in plants expressing pokeweed antiviral protein gene. Western blot analysis also showed elevated levels of PR1a in surviving plants.

Significant reduction of fungal disease symptoms in transgenic tobacco lines expressing pokeweed antiviral protein was observed. As shown in Tables IX and X, transgenic lines with PAP exhibited greater percentage of seedling survival after infection by *R. solani*. In addition, the disease progression, represented by the rate of seedling mortality, was also slower in transgenic PAP lines. Transgenic line 33617, which expressed the wild type PAP, as well as transgenic tobacco lines that contained mutant forms of PAP, NT144-12 (which expresses the active site mutant PAP), NT145-15 and NT147-19 (which expressed a truncated form of PAP, lacking 25 C-terminal amino acids) showed resistance to fungal infection.

Expression of the mutant PAP genes in tobacco proved to have absolutely no detectable phenotypic effect but surprisingly led to the constitutive expression of several pathogenesis-related proteins. Some of the genes induced are known for their anti-fungal activity. In the light of this observation, and while not intending to be limited to any particular theory of operation, Applicant believes that the resistance to *Rhizoctonia solani* infection by tobacco lines expressing mutant PAP genes of the present invention may be explained by the action of the host defense genes, and that resistance to fungus infection in plants expressing PAP may be conferred by dual action of PAP transgene and a number of host genes, constitutively expressed in transgenic tobacco. Applicant further believes that the induction of these plant defense genes further serves to protect transgenic plants against other pathogens such as bacterial pathogens.

EXAMPLE 8

Isolation of New PAP Mutants by Chromosomal Mutagenesis and Selection in Yeast A. Isolation of PAP Mutants Chromosomal mutagenesis and selection were used to isolate yeast mutants which permit cells to grow in the presence of PAP. Constitutive expression of PAP in *S. cerevisiae* is normally lethal. Therefore, the PAP gene was placed under the control of the galactose inducible GAL1 promoter. This enables cells carrying the plasmid with the PAP gene to grow normally on glucose when PAP expression is repressed, but kills cells grown on galactose when PAP is expressed. We have taken advantage of having an inducible PAP expression system and the toxicity of PAP to normal yeast cells, to isolate mutants which can grow in the presence of PAP. Yeast cells carrying a plasmid with the wild-type PAP gene (NT123) were grown to early log phase, pH 7.0, at a density of $1\times10^8$ cells/ml. Three 1 ml aliquots were removed and used for the mutagenesis. Mutagenesis was performed using either 5 μl or 25 μl of ethyl methanesulfonate (EMS). An unmutagenized aliquot was kept as the control to examine the frequency of spontaneous mutants. Following the addition of EMS, the cells were incubated at 30° C. for 1 hour, with gentle shaking. The mutagenesis was terminated by the addition of 5% sodium thiosulfate. The cells were then plated on uracil deficient plates with 2% glucose and incubated at 30° C. Based on the number of colonies which arose on the plates from the mutagenized cells versus the unmutagenized control, 35% and 98% of the cells were killed with 5 μl and 25 μl of EMS, respectively. These colonies were replica plated to uracil deficient media with 2% galactose and screened for clonies capable of growing in the presence of PAP. Approximately 13,500 colonies were screened, and 9 colonies were obtained which were able to grow on galactose.

The mutants were tested to see if the mutations were chromosomal or plasmid linked. Plasmid segregation was performed on the mutants by growing the cells for approximately 50 generations in non-selective media (YEPD), plating them out on YEPD, followed by replica plating the colonies which, having lost the plasmid, can no longer grow on uracil deficient media. The plasmid segregated cells were transformed with fresh NT123 plasmid and examined for their ability to grow on uracil deficient media with 2% galactose. Mutants which retained the ability to grow on galactose are chromosomal mutants, while mutants which failed to grow on galactose carry plasmid borne mutations.

The plasmid borne mutants were further characterized by performing immunoblot analysis on whole cell extracts from the cells expressing these plasmids. This analysis revealed that 2 of the 7 plasmid mutants were expressing a truncated form of PAP. The other 5 mutants were not expressing any PAP protein. The 2 mutants which were expressing truncated PAP were examined by sequence analysis to determine the sites of the mutations. One mutant, NT185, had a point mutation at the C-terminus, changing Lys210 (AAG) to a stop codon (TAG), resulting in a deletion of approximately 3.5 kDa. The other mutant, NT187 had a change in the N-terminus, changing Try16 (TAC) to a stop codon (TAA) and then was able to restart at Met39, resulting in a 24.8 kDa protein.

B. Construction of *E. Coli* Expression Vector

To express the N-terminal deleted mature PAP in *E. coli* cells, NT187 plasmid DNA was digested with BstYI and HindIII restriction enzymes and the fragment around 830 bp was purified using the Gene Clean kit (Bio 101). The purified fragment was ligated to the *E. coli* expression vector, pQE31 (QIAGEN Inc.), which was digested with BamHI and HindIII and then treated with alkaline phosphatase. The resulting plasmid, NT190, contains the N-terminal deletion mutant PAP in the *E. coli* expression vector pQE31.

C. Expression of PAP Mutants in *E. Coli.*

NT190 was isolated from *E. coli* DH5α cells and transformed into the expression host, *E. coli* M15 (pREP4). M15 cells containing NT190 were cultured on 50 ml of LB medium containing 2% glucose, 100 μg/ml ampicillin, and 50 μg/ml kanamycin at 37° C. overnight with vigorous shaking. The following day, a large culture (500 ml of LB medium, containing 2% glucose, 100 μg/ml ampicillin, and 50 μg/ml kanamycin) was inoculated and grown at 37° C. with vigorous shaking until $A_{600}$ reached 0.9. IPTG was added to a final concentration of 2 mM, and the culture was incubated at 37° C. for 5 hours. Cells were harvested by centrifugation at 4,000×g for 10 min and stored at −70° C.

D. Purification of N-Terminal Deleted PAP

One gram of *E. coli* cells was thawed and resuspended in 5 ml of buffer A (6M guanidinium hydrochloride, 0.1M sodium phosphate, and 0.01 M Tris-HCl, pH 8.0) and stirred for 1 hr at room temperature. *E. coli* lysate was centrifuged at 10,000×g for 15 min at 4° C. and supernatant was collected. Two ml of a 50% slurry of Ni-agarose resin (QIAGEN Inc.), previously equilibrated in buffer A, were added. After stirring at room temperature for 45 min, the resin was carefully loaded into a poly-prep chromatography column (Bio-Rad). The column was washed with 20 column volumes of buffer A, and 10 column volumes of buffer B (8M urea, 0.1 M sodium phosphate, and 0.01 M Tris-HCl, pH 8.0). Proteins which did not bind the resin were washed with 20 column volumes of buffer C (8M urea, 0.1M sodium phosphate, and 0.01M Tri-HCl, pH 6.3). Finally, the bound protein was eluted with 50 ml of buffer C containing 250 mM imidazole and analyzed by SDS-PAGE and western blot analysis.

E. Antiviral Activity of N-Terminal Deleted PAP

To determine if N-terminal deleted PAP had anti-viral activity, wild-type tobacco plants were inoculated with 1 μg/ml PVX in the presence or absence of N-terminal deletion mutant purified from *E. coli.* PAP concentration was determined by ELISA and by SDS-PAGE. Fifteen ng/μl and 1.5 ng/μl mutant PAP were applied to tobacco leaves in the presence or absence of 1 μg/ml PVX. As shown in Table XI, tobacco plants inoculated with PVX in the presence of 1.5 or 15 ng/μl N-terminal deleted PAP showed fewer lesions on their inoculated leaves compared to plants inoculated with PVX in the absence of mutant PAP. Furthermore, as shown in Table XII, none of the plants inoculated with PVX in the presence of 15 ng/μl mutant PAP, and only 13% of plants inoculated with PVX in the presence of 1.5 ng/μl mutant PAP showed systemic PVX symptoms, while 100% of the plants inoculated with PVX in the presence of buffer alone showed systemic PVX symptoms. These results indicate that exogenously applied N-terminal deleted PAP protects tobacco against PVX infection and is thus anti-viral.

TABLE XI

Susceptibility of tobacco plants to PVX in the presence of exogenously applied N-terminal deleted PAP

| Protein applied[a] (ng/μl) | PVX (μg/ml) | Mean # of lesions[b] |
|---|---|---|
| none | 1 | 20 +/− 16 |
| PAP (1.5) | 1 | 2 +/− 2 |
| PAP (15) | 1 | 2 +/− 2 |

[a]Two leaves from each plant were inoculated with 50 μl of PVX (1 μg/ml) in the presence of 1.5 or 15 ng/μl N-terminal deleted PAP. Twelve plants were inoculated with PVX in the presence of buffer alone ("none") and 8 plants were inoculated with PVX in the presence of 50 μl of 1.5 or 15 ng/μl of mutant PAP.
[b]The number of lesions were counted at 7 days post-inoculation. Mean values +/− SD are shown.

TABLE XII

Percentage of plants showing systemic symptoms in the presence of exogenously applied N-terminally deleted PAP

| Protein applied[a] | PVX (μg/ml) | % plants showing systemic (ng/μl) symptoms[b] |
|---|---|---|
| none | 1 | 100 |
| PAP (1.5) | 1 | 13 |
| PAP (15) | 1 | 0 |

[a]Two leaves from each plant were inoculated with 50 μl of PVX (1 μg/ml) in the presence of 1.5 or 15 ng/μl N-terminal deleted PAP. Twelve plants were inoculated with PVX in the presence of buffer alone ("none") and 8 plants were inoculated with PVX in the presence of 50 μl of 1.5 or 15 ng/μl of mutant PAP.
[b]Systemic symptoms were scored 11 days post inoculation.

Applicant's patent application Ser. Nos. 08/500,611 and 500,694, filed Jul. 11, 1995 and PCT Application No. PCT/US96/11546, now U.S. Pat. Nos. 5,756,322 and 5,880,329 are herein incorporated by reference in their entireties.

All publications and patent applications mentioned in this specification are indicative of the level of skill of those skilled in the art to which this invention pertains. All these publications and patent applications are herein incorporated by reference to the same extent as if each individual publication or patent application was specifically and individually indicated to be incorporated by reference.

Various modifications of the invention described herein will become apparent to those skilled in the art. Such modifications are intended to fall within the scope of the appending claims.

What is claimed is:

1. A pokeweed antiviral protein (PAP) mutant having reduced phytotoxicity compared to mature, wild-type PAP or PAP-v (Leu20Arg, Tyr49His), said PAP mutant containing intact catalytic active site amino acid residues (Glu176, Arg179) but differing from wild-type PAP substantially in that it is truncated at its N-terminus from 1 to about 38 amino acid residues, wherein the PAP mutant exhibits anti-viral or anti-fungal activity in plants.

2. The PAP mutant of claim 1, which is selected from the group of PAP mutants consisting of PAP (2-262), PAP (3-262), PAP (4-262), PAP (5-262), PAP (6-262), PAP (7-262), PAP (8-262), PAP (9-262), PAP (10-262), PAP (11-262), PAP (12-262), PAP (13-262), PAP (14-262), PAP (15-262), PAP (16-262), PAP (17-262), PAP (18-262), PAP (19-262), PAP (20-262), PAP (21-262), PAP (22-262), PAP (23-262), PAP (24-262), PAP (25-262), PAP (26-262), PAP (27-262), PAP (28-262), PAP (29-262), PAP (30-262), PAP (31-262), PAP (32-262), PAP (33-262), PAP (34-262), PAP (35-262), PAP (36-262), PAP (37-262), PAP (38-262) and PAP (39-262).

3. The PAP mutant of claim 1, further comprising the N-terminal signal sequence of wild-type PAP.

4. The PAP mutant of claim 1, further comprising the C-terminal extension of wild-type PAP.

5. A method of identifying a PAP mutant having reduced phytotoxicity, comprising:

(a) providing a eukaryotic cell stably transformed with a mutagenized PAP-encoding DNA molecule operably linked to an inducible promoter functional in eukaryotic cells, or with a non-mutagenized PAP-encoding DNA molecule followed by the step of mutagenizing the thus-transformed cell;

(b) culturing said transformed cell in suitable medium;

(c) adding an inducer to the medium to cause expression of the DNA molecule; and (d) determining whether said cultured cell survives the induction of expression of said PAP-encoding DNA molecule so that the biological activity of the PAP encoded by the mutagenized DNA molecule can then be determined.

6. The method of claim 5, wherein said providing comprises transforming a plurality of eukaryotic cells with randomly mutagenized PAP-encoding DNA molecules, and said step of determining comprises determining which transformed cells survive the induction of expression of said DNA molecules so that the biological activity of each of the PAPs encoded by the DNA molecule can then be determined.

7. The method of claim 5, further comprising assaying the PAP encoded by the DNA molecule to determine whether it retains PAP anti-fungal or anti-viral activity.

8. The method of claim 7, wherein said assaying comprises translating viral nucleic acid in an eukaryotic translation system in the presence of predetermined amounts of the PAP encoded by the DNA molecule.

9. The method of claim 8, wherein said translation system comprises a reticulocyte lysate system.

10. The method of claim 9, wherein said translation system comprises a rabbit reticulocyte lysate system.

11. The method of claim 5, wherein said eukaryotic cell is a yeast cell.

12. The method of claim 11, wherein said yeast is *Saccharomyces cerevisiae*.

13. An isolated and purified PAP mutant identified by the process of claim 5.

14. The PAP mutant of claim 1, which is PAP(2 262).

15. The PAP mutant of claim 1, which is PAP(3-262).

16. The PAP mutant of claim 1, which is PAP(4-262).

17. The PAP mutant of claim 1, which is PAP(5-262).

18. The PAP mutant of claim 1, which is PAP(6-262).

19. The PAP mutant of claim 1, which is PAP(7-262).

20. The PAP mutant of claim 1, which is PAP(8-262).

21. The PAP mutant of claim 1, which is PAP(9-262).

22. The PAP mutant of claim 1, which is PAP(10-262).

23. The PAP mutant of claim 1, which is PAP(11-262).

24. The PAP mutant of claim 1, which is PAP(12-262).

25. The PAP mutant of claim 1, which is PAP(13-262).

26. The PAP mutant of claim 1, which is PAP(14-262).

27. The PAP mutant of claim 1, which is PAP(15-262).

28. The PAP mutant of claim 1, which is PAP(16-262).

29. The PAP mutant of claim 1, which is PAP(17-262).

30. The PAP mutant of claim 1, which is PAP(18-262).

31. The PAP mutant of claim 1, which is PAP(19-262).

32. The PAP mutant of claim 1, which is PAP(20-262).

33. The PAP mutant of claim 1, which is PAP(21-262).

34. The PAP mutant of claim 1, which is PAP(22-262).

35. The PAP mutant of claim 1, which is PAP(23-262).

36. The PAP mutant of claim 1, which is PAP(24-262).

37. The PAP mutant of claim 1, which is PAP(25-262).

38. The PAP mutant of claim 1, which is PAP(26-262).

39. The PAP mutant of claim 1, which is PAP(27-262).

40. The PAP mutant of claim 1, which is PAP(28-262).

41. The PAP mutant of claim 1, which is PAP(29-262).

42. The PAP mutant of claim 1, which is PAP(30-262).

43. The PAP mutant of claim 1, which is PAP(31-262).

44. The PAP mutant of claim 1, which is PAP(32-262).

45. The PAP mutant of claim 1, which is PAP(33-262).

46. The PAP mutant of claim 1, which is PAP(34-262).

47. The PAP mutant of claim 1, which is PAP(35-262).

48. The PAP mutant of claim 1, which is PAP(36-262).

49. The PAP mutant of claim 1, which is PAP(37-262).

50. The PAP mutant of claim 1, which is PAP(38-262).

51. The PAP mutant of claim 1, which is PAP(39-262).

* * * * *

UNITED STATES PATENT AND TRADEMARK OFFICE

CERTIFICATE OF CORRECTION

PATENT NO. : 6,627,736 B1
APPLICATION NO. : 09/639456
DATED : September 30, 2003
INVENTOR(S) : Nilgun E. Tumer et al.

It is certified that error appears in the above-identified patent and that said Letters Patent is hereby corrected as shown below:

This certificate supersedes Certificate of Correction issued October 10, 2006, the certificate is to be vacated since no request for reprinted patent was requested by applicant. The patent is to be returned to its original state.

Signed and Sealed this

Twentieth Day of March, 2007

JON W. DUDAS

*Director of the United States Patent and Trademark Office*